United States Patent
Sahin et al.

(10) Patent No.: US 10,844,133 B2
(45) Date of Patent: *Nov. 24, 2020

(54) CANCER THERAPY USING CLDN6 TARGET-DIRECTED ANTIBODIES IN VIVO

(71) Applicants: Ganymed Pharmaceuticals AG, Mainz (DE); Johannes Gutenberg-Universitat Mainz, Mainz (DE)

(72) Inventors: Ugur Sahin, Mainz (DE); Ozlem Tureci, Mainz (DE); Michael Koslowski, Oberschleissheim (DE); Korden Walter, Wiesbaden (DE); Maria Kreuzberg, Mainz (DE); Sylvia Luxen, Mannheim (DE)

(73) Assignees: Ganymed Pharmaceuticals GmbH, Mainz (DE); Johannes Gutenberg-Universitat Mainz, Mainz (DE)

(*) Notice: Subject to any disclaimer, the term of this patent is extended or adjusted under 35 U.S.C. 154(b) by 298 days.

This patent is subject to a terminal disclaimer.

(21) Appl. No.: 15/866,139

(22) Filed: Jan. 9, 2018

(65) Prior Publication Data

US 2018/0142033 A1 May 24, 2018

Related U.S. Application Data

(60) Continuation of application No. 15/206,039, filed on Jul. 8, 2016, now Pat. No. 9,902,778, which is a division of application No. 13/808,423, filed as application No. PCT/EP2011/003312 on Jul. 4, 2011, now Pat. No. 9,718,886.

(60) Provisional application No. 61/361,632, filed on Jul. 6, 2010.

(30) Foreign Application Priority Data

Jul. 6, 2010 (EP) ..................... 10006957

(51) Int. Cl.
| C07K 16/30 | (2006.01) |
| C07K 16/28 | (2006.01) |
| A61K 39/00 | (2006.01) |

(52) U.S. Cl.
CPC ............ *C07K 16/30* (2013.01); *C07K 16/28* (2013.01); *C07K 16/3015* (2013.01); *C07K 16/3023* (2013.01); *C07K 16/3038* (2013.01); *C07K 16/3046* (2013.01); *C07K 16/3053* (2013.01); *C07K 16/3069* (2013.01); *A61K 2039/505* (2013.01); *C07K 2317/24* (2013.01); *C07K 2317/732* (2013.01); *C07K 2317/734* (2013.01); *C07K 2317/92* (2013.01)

(58) Field of Classification Search
CPC ..... C07K 16/30; C07K 16/28; C07K 2317/24
USPC ..................................................... 424/133.1
See application file for complete search history.

(56) References Cited

U.S. PATENT DOCUMENTS

| 4,946,778 A | 8/1990 | Ladner et al. |
| 5,624,821 A | 4/1997 | Winter et al. |
| 5,648,260 A | 7/1997 | Winter et al. |
| 6,121,022 A | 9/2000 | Presta et al. |
| 6,194,551 B1 | 2/2001 | Idusogie et al. |
| 6,277,375 B1 | 8/2001 | Ward |
| 6,830,894 B1 | 12/2004 | Blaschuk et al. |
| 7,431,927 B2 | 10/2008 | Couto et al. |
| 9,321,842 B2 | 4/2016 | Sahin et al. |
| 9,487,584 B2 | 11/2016 | Sahin et al. |
| 9,718,886 B2 | 8/2017 | Sahin et al. |
| 9,902,778 B2 | 2/2018 | Sahin et al. |
| 2002/0086356 A1 | 7/2002 | Tuschl et al. |
| 2002/0127584 A1 | 9/2002 | Baker et al. |
| 2003/0017534 A1 | 1/2003 | Buelow et al. |
| 2003/0118592 A1 | 6/2003 | Ledbetter et al. |
| 2003/0133939 A1 | 7/2003 | Ledbetter et al. |
| 2007/0082345 A1 | 4/2007 | Ota et al. |
| 2011/0059469 A1 | 3/2011 | Aburatani et al. |
| 2011/0300144 A1 | 12/2011 | Sahin et al. |
| 2012/0308478 A1 | 12/2012 | Sahin et al. |
| 2013/0183305 A1 | 7/2013 | Sahin et al. |
| 2014/0127219 A1 | 5/2014 | Sahin et al. |
| 2016/0159901 A1 | 6/2016 | Sahin et al. |

(Continued)

FOREIGN PATENT DOCUMENTS

| CA | 2379661 A1 | 9/2003 |
| CN | 101212989 A | 7/2008 |

(Continued)

OTHER PUBLICATIONS

Stadler et al., OncoImmunology, vol. 5(3): e1091555 (12 pages) (Mar. 3, 2016).*

"Bunshi Saibo Seibutsugaku Jiten" (Molecular Cell Biology Dictionary), 1st Ed., 2002, Tokyo Kagaku Dojin Co., Ltd., p. 282, definition of antigen binding site.

(Continued)

Primary Examiner — Lynn A Bristol
(74) Attorney, Agent, or Firm — Neal, Gerber & Eisenberg LLP; Kevin A. O'Connor

(57) ABSTRACT

The invention relates to the treatment and/or prevention of tumor diseases associated with cells expressing CLDN6, in particular cancer and cancer metastasis using antibodies which bind to CLDN6. The present application demonstrates that the binding of antibodies to CLDN6 on the surface of tumor cells is sufficient to inhibit growth of the tumor and to prolong survival and extend the lifespan of tumor patients. Furthermore, binding of antibodies to CLDN6 is efficient in inhibiting growth of CLDN6 positive germ cell tumors such as teratocarcinomas or embryonal carcinomas, in particular germ cell tumors of the testis.

20 Claims, 18 Drawing Sheets
Specification includes a Sequence Listing.

(56) References Cited

U.S. PATENT DOCUMENTS

| | | | |
|---|---|---|---|
| 2016/0222125 A1 | 8/2016 | Sahin et al. | |
| 2016/0264677 A1 | 9/2016 | Sahin et al. | |
| 2016/0355604 A1 | 12/2016 | Sahin et al. | |

FOREIGN PATENT DOCUMENTS

| | | |
|---|---|---|
| CN | 101687929 A | 3/2010 |
| EP | 338841 A1 | 10/1989 |
| EP | 1067182 A2 | 1/2001 |
| EP | 2011886 A2 | 1/2009 |
| EP | 2241578 A1 | 10/2010 |
| EP | 2322555 A1 | 5/2011 |
| JP | H-111999503014 A1 | 3/1999 |
| JP | 2001506275 A | 5/2001 |
| JP | 2002536995 A | 11/2002 |
| JP | 2004537534 A | 12/2004 |
| JP | 2006526641 A | 11/2006 |
| JP | 2007529416 A | 10/2007 |
| JP | 2011501758 A | 1/2011 |
| JP | 2011516580 A | 5/2011 |
| JP | 2012512778 A | 6/2012 |
| JP | 2012518608 A | 8/2012 |
| JP | 2012518609 A | 8/2012 |
| JP | 2013533247 A | 8/2013 |
| WO | WO 8704462 A1 | 7/1987 |
| WO | WO 8901036 A1 | 2/1989 |
| WO | WO 9204381 A1 | 3/1992 |
| WO | WO 9633265 A1 | 10/1996 |
| WO | WO 9633739 A1 | 10/1996 |
| WO | WO 9924463 A2 | 5/1999 |
| WO | WO 9945962 A1 | 9/1999 |
| WO | WO 0012708 A2 | 3/2000 |
| WO | WO 0026360 A1 | 5/2000 |
| WO | WO 0035937 A1 | 6/2000 |
| WO | WO 0073348 A2 | 12/2000 |
| WO | WO 0078961 A1 | 12/2000 |
| WO | WO 0151513 A2 | 7/2001 |
| WO | WO 0153312 A1 | 7/2001 |
| WO | WO 0193983 A1 | 12/2001 |
| WO | WO 0200690 A2 | 1/2002 |
| WO | WO 0208284 A2 | 1/2002 |
| WO | WO 0208288 A2 | 1/2002 |
| WO | WO 0243478 A2 | 6/2002 |
| WO | WO 03088808 A2 | 10/2003 |
| WO | WO 2004030615 A2 | 4/2004 |
| WO | WO 2004035607 A2 | 4/2004 |
| WO | WO 2004060270 A2 | 7/2004 |
| WO | WO2004110363 A2 | 12/2004 |
| WO | WO 2005005601 A2 | 1/2005 |
| WO | WO 2006033664 A1 | 3/2006 |
| WO | WO 2009025759 A1 | 2/2009 |
| WO | WO 2009028663 A1 | 3/2009 |
| WO | WO 2010043650 A2 | 4/2010 |
| WO | WO 2008114733 A1 | 7/2010 |
| WO | WO 2010094499 A1 | 8/2010 |
| WO | WO 2009087978 A1 | 5/2011 |
| WO | WO 2011057788 A1 | 5/2011 |
| WO | WO 2012003956 A1 | 1/2012 |
| WO | WO 2013087929 A2 | 6/2013 |
| WO | WO 2014015148 A1 | 1/2014 |

OTHER PUBLICATIONS

"Menekigaku Jiten" (Dictionary of Immunology), 2nd Ed., 2001, Tokyo Kagaku Dojin Co., Ltd., p. 501, definition of humanized antibody.
Adams, G.P. et al., Cancer Res., (2001), vol. 61, pp. 4750-4755.
Allard et al., Clin Cancer Res 10:6897-904,2004.
Altman et al., Science 274:94-96, 1996.
Anderson et al., J. Immunol. 143: 1899-1904, 1989.
Anonymous: "Tumor Marker—National Cancer Institute", Dec. 7, 2011 (Dec. 7, 2011), Retrieved from the Internet: URL:http://www.cancer.gov/cancertopics/diagnosis-staging/diagnosis/tumor—markers-fact-sheet [retrieved on Mar. 20, 2015].
Arabzadeh et al., "Changes in the distribution pattern of Caludin tight junction proteins during the progression of mouse skin tumorigenesis.", BMC Cancer, vol. 7, Oct. 18, 2007, p. 196, XP021034484.
Amon et al. Monoclonal Antibodies for Immunotargeting of Drugs in Cancer Therapy Resifeld et al. (eds.), pp. 243-256 (Alan R. Liss, Inc. 1985).
Babcook et al., Proc. Natl. Acad. Sci, USA, vol. 93, pp. 7843-7848, Jul. 1996; A novel strategy for generating monoclonal antibodies from single, isolated lymphocytes producing antibodies of defined strategy.
Beadling et al., Nature Medicine 12:1208 (2006).
Benny K.C. Lo Antibody Engineering ISBN: 1-58829-092-1, 2004.
Berge, S.M., et al. (1977) J. Pharm. Sci. 66:12-19.
Berzofsky et al., "Antibody-Antigen Interactions" In Fundamental Immunology, Paul, W. E., Ed., Raven Press New York, NY (1984), Kuby, Janis Immunology, W. H. Freeman and Company New York, N Y (1992).
Bird et al. (1988) Science 242: 423-426.
Brown, et al., "Tolerance to Single, but not Multiple, Amino Acid Replacements in Antibody VH CDR2," J. Immunol. May 1996; 156 (9):3285-91.
Casset et al. (Biochemical and Biophysical Research Communications, 2003, 307:198-205).
Chen et al. (Journal of Molecular Biology, 1999, 293:865-881).
Clark, W.R. (1986), The Experimental Foundations of Modern Immunology.
Cristofanilli et al, N Eng.J Med 351: 781-91, 2004.
Cunningham-Rundles C, Zhuo Z, Griffith B, Keenan J. (1992) Biological activities of polyethylene-glycol immunoglobulin conjugates. Resistance to enzymatic degradation. 1. Immunol. Methods, 152: 177-190.
David U., et al., "Immunoligic and Chemical Targeting of the Tight-Junction Protein Claudin-6 Eliminates Tumorigenic Human Pluripotent Stem Cells," Natural Communications 2013, vol. 4, Jun. 18, 2013, XP008168176, p. 1992.
Documentation of Affymetrix probe set "75948_AT", Feb. 2009.
Dormeyer, W. et al., "Plasma Membrane Proteomics of Human Embryonic Stem Cells and Human Embroyonal Carcinoma Cells," Journal of Proteome Research, American Chemical Society, Washington, DC., US, vol. 7, XP002599270, Jul. 3, 2008, pp. 2936-2951.
Dowd KA et al., Genotypic differences in dengue virus neutralization are explained by a single amino acid mutation that modulates virus breathing. mBio 6(6):e01559-15, Nov./Dec. 2015.
Dunbar et al., Curro Biol. 8:413-416, 1998.
European Search Report corresponding to European Patent Application Serial No. 09014136.7 dated Mar. 23, 2010.
Extended European Search Report for European Patent Application No. 09002452.2-1212, dated Oct. 22, 2009.
Extended European Search Report for European Patent Application No. 10006957.4-2406, dated Nov. 10, 2010.
Fischer, R., et al. (1999) Biol. Chem. 380: 825-839.
Gardsvoll, J. Immunol. Methods 234: 107-116, 2000.
GenBank. *Homo sapiens* claudin 6 (CLDN6), mRNA NCB I Reference Sequence: NM_021195.4, 2014.
Goodman and Gilman, "The Pharmacological Basis of Therapeutics", 8th Edition, 1990, McGraw-Hill, Inc., in particular Chapter 52 Antineoplastic Agents Paul Calabresi and Bruce A. Chabner.
Hall (1995) Science 268: 1432-1434.
Harlow et al. Antibodies: A Laboratory Manual ISBN: 0879693142, 1988.
Harlow et al. Using Antibodies: A Laboratory Manual: Portable Protocol NO ISBN 0879695447, 1998.
Hellstrom et al., "Antibodies for Drug Delivery" in Controlled Drug Delivery (2nd Ed.), Robinson et al. (eds.), pp. 323-653 (Marcel Dekker, Inc. 1987).
Hewitt et al., "The claudin gene family: expression in normal and neoplastic tissues." BMC Cancer, Biomed Central, vol. 6, No. 1, Jul. 12, 2006. XP021016181.
Holliger, P., et al. (1993) Proc. Natl. Acad. Sci. USA 90: 6444-6448.
Hong Yeon-Hee et al., "Up-regulation of the claudin-6 gene in adipongenesis." Bioscience Biotechnology, and Biochemistry, Nov. 2005, vol. 69, No. 11, pp. 2117-2121, XP002547908.

(56) References Cited

OTHER PUBLICATIONS

Huang Yu-Hung et al., "Claudin-3 gene silencing with siRNA suppresses ovarian tumor growth and metastasis." Proceedings of the National Academy of Sciences of the United States of America 3, Mar. 2009, vol. 106, No. 9, Feb. 10, 2009, pp. 3426-3430, XP002547909.
Huston et al. (1988) Proc. Natl. Acad. Sci. USA 85: 5879-5883.
Iacobuzio-Donahue et al. Amer. Journ. Pathology, vol. 160, No. 4 pp. 1239-1249, Apr. 2002.
International Preliminary Report on Patentability for Patent Application No. PCT/EP2011/003312, dated Jan. 8, 2013.
International Search Report and Written Opinion for International Patent Application No. PCT/EP2011/003312, dated Oct. 5, 2011.
IPRP for PCT/EP2010/001062, dated Sep. 1, 2011.
IPRP for PCT/EP2010/006888 dated May 15, 2012.
IPRP for PCT/EP2012/001721 dated Nov. 19, 2013.
ISR & WO for PCT/EP2010/006888, dated Feb. 4, 2011.
ISR for PCT/EP2012/001721 dated Jul. 25, 2012.
U.S. Appl. No. 13/201,702, US 2011/0300144 A1, U.S. Pat. No. 9,809,815.
U.S. Appl. No. 15/726,063.
U.S. Appl. No. 13/503,461, US 2012/0308478 A1, U.S. Pat. No. 9,487,584.
U.S. Appl. No. 15/133,783, US 2016/0222125 A1, U.S. Pat. No. 9,932,401.
U.S. Appl. No. 15/885,454.
U.S. Appl. No. 13/808,423, US 2013/0183305 A1, U.S. Pat. No. 9,718,886.
U.S. Appl. No. 15/206,039, US 2016/0355604 A1, U.S. Pat. No. 9,902,778.
U.S. Appl. No. 14/117,118, US 2014/0127219 A1, U.S. Pat. No. 9,321,842.
U.S. Appl. No. 15/076,536, US 2016/0264677 A1.
U.S. Appl. No. 14/904,011, US 2016/0159901 A1.
ISR for PCT/EP2014/066330 dated Nov. 17, 2014.
Jones, P. et al. (1986) Nature 321: 522-525.
K. Fujimori et al., J. Nucl. Med., 31: 1191-1198, 1990.
Kessels et al., Nat Immunol. 2:957-61, 2001.
Kohler and Milstein, Nature 256: 495 (1975).
Koslowski et al, 2006.
Koslowski et al, 2007, Cancer Research 67(19): 9528-9534, 2007.
Kozak, 1991, J. Biol. Chem. 266: 19867-19870.
Kraeft et al, Clin Cancer Res 10: 3020-8, 2004.
Kraus et al., in Methods in Molecular Biology series, Recombinant antibodies for cancer therapy ISBN-0-89603-918-8, 2002.
Krieg et al., 1995, Nature 374: 546-549.
Kwon, M., "Emerging Roles of Claudins in Human Cancer," International Journal of Molecular Science, Fol. 14, No. 9, Sep. 4, 2013, XP055107170, pp. 18148-18180.
Lamminmaki et al. (Journal of Biological Chemistry, 2001, 276:36687-36694.
Landor M. (1995) Maternal-fetal transfer of immunoglobulins, Ann. Allergy Asthma Immunol. 74: 279-283.
Lu et al (2004) Clinical Cancer Research vol. 10: 3291-3300.
Maloy et al., Proc Natl Acad Sci USA 98:3299-303, 2001.
Matz et al. (Nucleic Acids research, 1999 vol. 27, No. 6 1558-60.
Merrifield, R.B. Solid-Phase Peptide Synthesis. III. An Improved Synthesis of Bradykinin, Biochemistry, 3:1385-90 (1964).
Ming-Ming Tsai: "Potential prognostic, diagnostic and therapeutic markers for human gastric cancer", World Journal of Gastroenterology, vol. 20, No. 38, Oct. 14, 2014 (Oct. 14, 2014), p. 13791.
Monteiro, R. C. et al. (1992) J. Immunol. 148: 1764).
Morita et al., "Endothelial claudin: Claudin-5/TMVCF constitutes tight junction strands in endothelial cells." The Journal of Cell Biology, vol. 147, No. 1, Oct. 4, 1999, pp. 185-194, XP002239048.
Morris, Glenn E. Epitope Mapping Protocols (Methods in Molecular Biology) ISBN-089603-375-9 (1996).
Morrison, S. (1985) Science 229: 1202.
Morton, H.C. et al. (1996) Critical Reviews in Immunology 16: 423-440).
Neddleman and Wunsch, 1970, J. Mol. Biol. 48, 443.
Neefjes et al., Nature Reviews, Immunology, vol. 11, pp. 823-836 (Dec. 2011).
Order, Stanley, pp. 303-316 (1985) Baldwin et al. (eds.); "Analysis, Results, and Future Prospective of the Therapeutic Use of Radiolabeled Antibody in Cancer Therapy", in Monoclonal Antibodies for Cancer Detection and Therapy.
Osanai Makoto et al., "Epigenetic silencing of claudin-6 promotes anchorage-independent growth of breast carcinoma cells." Cancer Science Oct. 2007, vol. 98, No. 10, pp. 1557-1562, XP002547907.
Ossendorp et al., Immunol Lett. 74:75-9, 2000.
Ossendorp et al., J. Exp. Med. 187:693-702, 1998.
Padlan et al. (Proceedings of the National Academy of Sciences, 1989, 86:5938-5942).
Pakula A. A. et al., Genetic analysis of protein stability and function. Annu. Rev. Genet., 1989 No. 23, pp. 289-310.
Pascalis et al. (The Journal of Immunology, 2002, 169, 2076-3084).
Pearson and Lipman, 1988, Proc. Natl Acad. Sci. USA 85, 2444.
Poljak, R. J., et al. (1994) Structure 2: 1121-1123.
Pollock, et al. (1999) J. Immunol. Meth. 231: 147-157.
Prat, A., et al., "Phenotypic and Molecular Characterization of the Claudin-Low Intrinsic Subtype of Breast Cancer," Breast Cancer Research, Current Science, London, GB, vol. 12, No. 5, Sep. 2, 2010, XP021085380, p. R68.
Queen, C. et aL (1989) Proc. NatL Acad. Sci. U. S. A. 86: 10029-10033.
Reddehase et al., Nature vol. 337, pp. 651-653 (Feb. 1989).
Remington: The Science and Practice of Pharmacy, 19th Edition, Gennaro, Ed., Mack Publishing Co., Easton, PA, 1995.
Riechmann, L. et al (1998) Nature 332: 323-327.
Robinson, J.R., ed. Sustained and Controlled Release Drug Delivery Systems, Marcel Dekker, Inc., New York, 1978.
Roitt, I. (1991), Essential Immunology, 7th Edition, Blackwell Scientific Publications, Oxford.
Rossi et al., Am. J. Clin. Pathol. 124: 295 (2005).
Rudikoff et al. (Proceedings of the National Academy of Science USA, 1982, 79:1979).
Sambrook et al., Molecular Cloning: A Laboratory Manual, 1. Editors, 2nd Edition, Cold Spring Harbor Laboratory Press, Cold Spring Harbor, New York, 1989 Ausubel et al., Current Protocols in Molecular Biology, Editors, John Wiley & Sons, Inc., New York.
Satohisa et al. (Experimental Cell Research, 2005: 310:66-78).
Scatchard et al., Ann N.Y. Acad. ScL, 51:660 (1949).
Science 268: 1432-1434, 1995.
Sharon, J., Proc. Natl. Acad. Sci. USA, (1990), vol. 87, pp. 4814-4817.
Shepherd et al. Monoclonal Antibodies: A Practical Approach ISBN 0-19-963722-9, 2000.
Shields et al. (2002) JBC, 277: 26733.
Smirnov et al, Cancer Res 65: 4993-7, 2005.
Smith and Waterman, 1981, Ads App. Math. 2, 482.
So et al., 1997, Mol. Cells 7: 178-186.
Soares et al., Correlation between conformation and antibody binding: NMR structure of cross-reactive peptides from T. cruzi, human and L. braziliensis. FEBS Letters 560: 134-140, 2004.
Spieker-Polet et al. Proc. Natl. Acad. Sci. U.S.A. 92:9348 (1995).
Stanislawski et al., Nat Immunol. 2:962-70, 2001.
Strejan et al. (1984) J. Neuroimmunol. 7: 27.
Thorpe et al., "The Preparation and Cytotoxic Properties of Antibody-Toxin Conjugates" Immunol. Rev., 62: 119-58 (1982).
Thorpe, "Antibody Carriers of Cytotoxic Agents in Cancer Therapy: A Review" in Monoclonal Antibodies '84: Biological and Clinical Applications, Pinchera et al. (eds. ), pp. 475-506 (1985).
Trail, P., "Antibody Drug Conjugates as Cancer Therapeutics," Antibodies, M D P I AG, CH, vol. 2, No. 1, Feb. 27, 2013, XP002725437, pp. 113-129.
Turksen, K., "Claudins and Cancer Stem Cells," Stem Cell Reviews and Reports, Humana Press Inc., New York, vol. 7, No. 4, Apr. 28, 2011, XP019985913, pp. 797-798.
Tuschl T. et al., "The siRNA User Guide", revised Oct. 11, 2002.
Ushiku T. et al., "Distinct Expression Pattern of Claudin-6, a Primitive Phenotypic Tight Junction Molecule, in Germ Cell Tumours

(56) References Cited

OTHER PUBLICATIONS and Visceral Carcinomas," Histopatology, vol. 61, No. 6, Jul. 17, 2012, XP055107355, pp. 1043-1056.
Vajdos F. F. et al., Comprehensive Functional Maps of the Antigenbinding Site of an Anti-ErbB2 Antibody Obtained with Shotgun Scanning Mutagenesis, J. Mol. Biol., 2002, vol. 320, pp. 415-428.
Vare, et al., "Twist is inversely associated with claudins in germ cell tumors of the testis," APMIS 118: 640-647, published online Jun. 11, 2010.
Verma, R., et al. (1998) J. Immunol. Meth. 216: 165-181.
Wang, L., et al., "Claudin 6: A Novel Surface Marker for Characterizing Mouse Pluripotent Stem Cells," Cell Research, vol. 22, No. 6, May 8, 2012, XP055107350, pp. 1082-1085.
Ward et al., (1989) Nature 341: 544-546.
Westwood, et al. "Epitope Mapping: A Practical Approach" Practical Approach Series, 248, 2008.
Yuan et al. (Cytotherapy 8:498, 2006).
International Application No. PCT JP2009000082, Anti-CLDN6 antibody, english translation, 30 pages, published Jul. 16, 2009.
International Application No. PCT JP2009000082, Anti-CLDN6 antibody, sequence listing, 4 pages, published Jul. 16, 2009.

\* cited by examiner

SEQUENCE LISTING

```
<160> NUMBER OF SEQ ID NOS: 13

<210> SEQ ID NO 1
<211> LENGTH: 1369
<212> TYPE: DNA
<213> ORGANISM: Homo sapiens

<400> SEQUENCE: 1
cgacactcgg cctaggaatt tcccttatct ccttcgcagt gcagctcctt caacctcgcc      60
atggcctctg ccggaatgca gatcctggga gtcgtcctga cactgctggg ctgggtgaat     120
ggcctggtct cctgtgccct gcccatgtgg aaggtgaccg ctttcatcgg caacagcatc     180
gtggtggccc aggtggtgtg ggagggcctg tggatgtcct gcgtggtgca gagcaccggc     240
cagatgcagt gcaaggtgta cgactcactg ctggcgctgc cacaggacct gcaggctgca     300
cgtgccctct gtgtcatcgc cctccttgtg gccctgttcg gcttgctggt ctaccttgct     360
ggggccaagt gtaccacctg tgtggaggag aaggattcca aggcccgcct ggtgctcacc     420
tctgggattg tctttgtcat ctcaggggtc ctgacgctaa tccccgtgtg ctggacgcg      480 catgccatca tccgggactt ctataacccc ctggtggctg aggcccaaaa gcgggagctg     540
ggggcctccc tctacttggg ctgggcgcc tcaggccttt tgttgctggg tggggggttg     600
ctgtgctgca cttgcccctc ggggggtcc cagggcccca gccattacat ggcccgctac     660
```

-continued

```
tcaacatctg cccctgccat ctctcggggg ccctctgagt accctaccaa gaattacgtc    720
tgacgtggag gggaatgggg gctccgctgg cgctagagcc atccagaagt ggcagtgccc    780
aacagctttg gatgggttc gtacctttg tttctgcctc ctgctatttt tcttttgact     840
gaggatattt aaaattcatt tgaaaactga gccaaggtgt tgactcagac tctcacttag    900
gctctgctgt ttctcaccct tggatgatgg agccaaagag gggatgcttt gagattctgg    960
atcttgacat gcccatctta gaagccagtc aagctatgga actaatgcgg aggctgcttg   1020
ctgtgctggc tttgcaacaa gacagactgt ccccaagagt tcctgctgct gctgggggct   1080
gggcttccct agatgtcact ggacagctgc cccccatcct actcaggtct ctggagctcc   1140
tctcttcacc cctggaaaaa caaatgatct gttaacaaag gactgcccac ctccggaact   1200
tctgacctct gtttcctccg tcctgataag acgtccaccc cccagggcca ggtcccagct   1260
atgtagaccc ccgcccccac ctccaacact gcaccttct gccctgcccc cctcgtctca    1320
ccccctttac actcacattt ttatcaaata aagcatgttt tgttagtgc               1369
```

<210> SEQ ID NO 2
<211> LENGTH: 220
<212> TYPE: PRT
<213> ORGANISM: Homo sapiens

<400> SEQUENCE: 2

```
Met Ala Ser Ala Gly Met Gln Ile Leu Gly Val Val Leu Thr Leu Leu
1               5                   10                  15

Gly Trp Val Asn Gly Leu Val Ser Cys Ala Leu Pro Met Trp Lys Val
            20                  25                  30

Thr Ala Phe Ile Gly Asn Ser Ile Val Val Ala Gln Val Val Trp Glu
        35                  40                  45

Gly Leu Trp Met Ser Cys Val Val Gln Ser Thr Gly Gln Met Gln Cys
    50                  55                  60

Lys Val Tyr Asp Ser Leu Leu Ala Leu Pro Gln Asp Leu Gln Ala Ala
65                  70                  75                  80

Arg Ala Leu Cys Val Ile Ala Leu Leu Val Ala Leu Phe Gly Leu Leu
                85                  90                  95

Val Tyr Leu Ala Gly Ala Lys Cys Thr Thr Cys Val Glu Glu Lys Asp
            100                 105                 110

Ser Lys Ala Arg Leu Val Leu Thr Ser Gly Ile Val Phe Val Ile Ser
        115                 120                 125

Gly Val Leu Thr Leu Ile Pro Val Cys Trp Thr Ala His Ala Ile Ile
    130                 135                 140

Arg Asp Phe Tyr Asn Pro Leu Val Ala Glu Ala Gln Lys Arg Glu Leu
145                 150                 155                 160

Gly Ala Ser Leu Tyr Leu Gly Trp Ala Ala Ser Gly Leu Leu Leu Leu
                165                 170                 175

Gly Gly Gly Leu Leu Cys Cys Thr Cys Pro Ser Gly Ser Gln Gly
            180                 185                 190

Pro Ser His Tyr Met Ala Arg Tyr Ser Thr Ser Ala Pro Ala Ile Ser
        195                 200                 205

Arg Gly Pro Ser Glu Tyr Pro Thr Lys Asn Tyr Val
    210                 215                 220
```

<210> SEQ ID NO 3
<211> LENGTH: 53
<212> TYPE: PRT

<213> ORGANISM: Homo sapiens

<400> SEQUENCE: 3

Pro Met Trp Lys Val Thr Ala Phe Ile Gly Asn Ser Ile Val Val Ala
1               5                   10                  15

Gln Val Val Trp Glu Gly Leu Trp Met Ser Cys Val Val Gln Ser Thr
            20                  25                  30

Gly Gln Met Gln Cys Lys Val Tyr Asp Ser Leu Leu Ala Leu Pro Gln
        35                  40                  45

Asp Leu Gln Ala Ala
    50

<210> SEQ ID NO 4
<211> LENGTH: 33
<212> TYPE: PRT
<213> ORGANISM: Homo sapiens

<400> SEQUENCE: 4

Glu Gly Leu Trp Met Ser Cys Val Val Gln Ser Thr Gly Gln Met Gln
1               5                   10                  15

Cys Lys Val Tyr Asp Ser Leu Leu Ala Leu Pro Gln Asp Leu Gln Ala
            20                  25                  30

Ala

<210> SEQ ID NO 5
<211> LENGTH: 13
<212> TYPE: PRT
<213> ORGANISM: Homo sapiens

<400> SEQUENCE: 5

Arg Asp Phe Tyr Asn Pro Leu Val Ala Glu Ala Gln Lys
1               5                   10

<210> SEQ ID NO 6
<211> LENGTH: 220
<212> TYPE: PRT
<213> ORGANISM: Homo sapiens

<400> SEQUENCE: 6

Met Ala Ser Ala Gly Met Gln Ile Leu Gly Val Val Leu Thr Leu Leu
1               5                   10                  15

Gly Trp Val Asn Gly Leu Val Ser Cys Ala Leu Pro Met Trp Lys Val
            20                  25                  30

Thr Ala Phe Ile Gly Asn Ser Ile Val Val Ala Gln Val Val Trp Glu
        35                  40                  45

Gly Leu Trp Met Ser Cys Val Val Gln Ser Thr Gly Gln Met Gln Cys
    50                  55                  60

Lys Val Tyr Asp Ser Leu Leu Ala Leu Pro Gln Asp Leu Gln Ala Ala
65                  70                  75                  80

Arg Ala Leu Cys Val Ile Ala Leu Leu Val Ala Leu Phe Gly Leu Leu
                85                  90                  95

Val Tyr Leu Ala Gly Ala Lys Cys Thr Thr Cys Val Glu Glu Lys Asp
            100                 105                 110

Ser Lys Ala Arg Leu Val Leu Thr Ser Gly Ile Val Phe Val Ile Ser
        115                 120                 125

Gly Val Leu Thr Leu Ile Pro Val Cys Trp Thr Ala His Ala Val Ile
    130                 135                 140

Arg Asp Phe Tyr Asn Pro Leu Val Ala Glu Ala Gln Lys Arg Glu Leu

```
                145                 150                 155                 160
Gly Ala Ser Leu Tyr Leu Gly Trp Ala Ala Ser Gly Leu Leu Leu
                165                 170                 175

Gly Gly Gly Leu Leu Cys Cys Thr Cys Pro Ser Gly Ser Gln Gly
                180                 185                 190

Pro Ser His Tyr Met Ala Arg Tyr Ser Thr Ser Ala Pro Ala Ile Ser
                195                 200                 205

Arg Gly Pro Ser Glu Tyr Pro Thr Lys Asn Tyr Val
    210                 215                 220

<210> SEQ ID NO 7
<211> LENGTH: 217
<212> TYPE: PRT
<213> ORGANISM: Homo sapiens

<400> SEQUENCE: 7

Met Ala Ser Thr Gly Leu Glu Leu Leu Gly Met Thr Leu Ala Val Leu
1               5                   10                  15

Gly Trp Leu Gly Thr Leu Val Ser Cys Ala Leu Pro Leu Trp Lys Val
                20                  25                  30

Thr Ala Phe Ile Gly Asn Ser Ile Val Val Ala Gln Val Val Trp Glu
            35                  40                  45

Gly Leu Trp Met Ser Cys Val Val Gln Ser Thr Gly Gln Met Gln Cys
        50                  55                  60

Lys Val Tyr Asp Ser Leu Leu Ala Leu Pro Gln Asp Leu Gln Ala Ala
65                  70                  75                  80

Arg Ala Leu Cys Val Ile Ala Leu Leu Leu Ala Leu Leu Gly Leu Leu
                85                  90                  95

Val Ala Ile Thr Gly Ala Gln Cys Thr Thr Cys Val Glu Asp Glu Gly
                100                 105                 110

Ala Lys Ala Arg Ile Val Leu Thr Ala Gly Val Ile Leu Leu Leu Ala
                115                 120                 125

Gly Ile Leu Val Leu Ile Pro Val Cys Trp Thr Ala His Ala Ile Ile
                130                 135                 140

Gln Asp Phe Tyr Asn Pro Leu Val Ala Glu Ala Leu Lys Arg Glu Leu
145                 150                 155                 160

Gly Ala Ser Leu Tyr Leu Gly Trp Ala Ala Ala Leu Leu Met Leu
                165                 170                 175

Gly Gly Gly Leu Leu Cys Cys Thr Cys Pro Pro Pro Gln Val Glu Arg
                180                 185                 190

Pro Arg Gly Pro Arg Leu Gly Tyr Ser Ile Pro Ser Arg Ser Gly Ala
                195                 200                 205

Ser Gly Leu Asp Lys Arg Asp Tyr Val
    210                 215

<210> SEQ ID NO 8
<211> LENGTH: 209
<212> TYPE: PRT
<213> ORGANISM: Homo sapiens

<400> SEQUENCE: 8

Met Ala Ser Met Gly Leu Gln Val Met Gly Ile Ala Leu Ala Val Leu
1               5                   10                  15

Gly Trp Leu Ala Val Met Leu Cys Cys Ala Leu Pro Met Trp Arg Val
                20                  25                  30

Thr Ala Phe Ile Gly Ser Asn Ile Val Thr Ser Gln Thr Ile Trp Glu
```

```
            35                  40                  45
Gly Leu Trp Met Asn Cys Val Val Gln Ser Thr Gly Gln Met Gln Cys
 50                  55                  60
Lys Val Tyr Asp Ser Leu Leu Ala Leu Pro Gln Asp Leu Gln Ala Ala
 65                  70                  75                  80
Arg Ala Leu Val Ile Ser Ile Ile Val Ala Ala Leu Gly Val Leu
                 85                  90                  95
Leu Ser Val Val Gly Gly Lys Cys Thr Asn Cys Leu Glu Asp Glu Ser
                100                 105                 110
Ala Lys Ala Lys Thr Met Ile Val Ala Gly Val Val Phe Leu Leu Ala
                115                 120                 125
Gly Leu Met Val Ile Val Pro Val Ser Trp Thr Ala His Asn Ile Ile
                130                 135                 140
Gln Asp Phe Tyr Asn Pro Leu Val Ala Ser Gly Gln Lys Arg Glu Met
145                 150                 155                 160
Gly Ala Ser Leu Tyr Val Gly Trp Ala Ala Ser Gly Leu Leu Leu Leu
                165                 170                 175
Gly Gly Gly Leu Leu Cys Cys Asn Cys Pro Pro Arg Thr Asp Lys Pro
                180                 185                 190
Tyr Ser Ala Lys Tyr Ser Ala Ala Arg Ser Ala Ala Ala Ser Asn Tyr
                195                 200                 205
Val

<210> SEQ ID NO 9
<211> LENGTH: 220
<212> TYPE: PRT
<213> ORGANISM: Homo sapiens

<400> SEQUENCE: 9

Met Ser Met Gly Leu Glu Ile Thr Gly Thr Ala Leu Ala Val Leu Gly
 1                   5                  10                  15
Trp Leu Gly Thr Ile Val Cys Cys Ala Leu Pro Met Trp Arg Val Ser
                 20                  25                  30
Ala Phe Ile Gly Ser Asn Ile Ile Thr Ser Gln Asn Ile Trp Glu Gly
                 35                  40                  45
Leu Trp Met Asn Cys Val Val Gln Ser Thr Gly Gln Met Gln Cys Lys
 50                  55                  60
Val Tyr Asp Ser Leu Leu Ala Leu Pro Gln Asp Leu Gln Ala Ala Arg
 65                  70                  75                  80
Ala Leu Ile Val Val Ala Ile Leu Leu Ala Ala Phe Gly Leu Leu Val
                 85                  90                  95
Ala Leu Val Gly Ala Gln Cys Thr Asn Cys Val Gln Asp Asp Thr Ala
                100                 105                 110
Lys Ala Lys Ile Thr Ile Val Ala Gly Val Leu Phe Leu Leu Ala Ala
                115                 120                 125
Leu Leu Thr Leu Val Pro Val Ser Trp Ser Ala Asn Thr Ile Ile Arg
                130                 135                 140
Asp Phe Tyr Asn Pro Val Val Pro Glu Ala Gln Lys Arg Glu Met Gly
145                 150                 155                 160
Ala Gly Leu Tyr Val Gly Trp Ala Ala Ala Leu Gln Leu Leu Gly
                165                 170                 175
Gly Ala Leu Leu Cys Cys Ser Cys Pro Pro Arg Glu Lys Lys Tyr Thr
                180                 185                 190
Ala Thr Lys Val Val Tyr Ser Ala Pro Arg Ser Thr Gly Pro Gly Ala
```

```
               195                 200                 205
Ser Leu Gly Thr Gly Tyr Asp Arg Lys Asp Tyr Val
    210                 215                 220
```

<210> SEQ ID NO 10
<211> LENGTH: 780
<212> TYPE: DNA
<213> ORGANISM: Artificial
<220> FEATURE:
<223> OTHER INFORMATION: synthetic nucleic acid

<400> SEQUENCE: 10

```
caagcgcgtc aattaaccct cactaaaggg aacaaaagct gttaattaac taaggtacca       60
agcttgccac catggccagc gccggcatgc agatcctggg agtggtgctg accctgctgg      120
gctgggtgaa cggcctggtg tcctgcgccc tgcccatgtg gaaagtgacc gccttcatcg      180
gcaacagcat cgtggtggcc caggtcgtgt gggagggcct gtggatgagc tgtgtggtgc      240
agagcaccgg ccagatgcag tgcaaggtgt acgacagcct gctggccctg cctcaggatc      300
tgcaggccgc cagagccctg tgtgtgatcg ccctgctggt cgcctgttc ggcctgctgg      360
tgtacctcgc tggcgccaag tgcaccacct gtgtggagga aaaggacagc aaggcccggc      420
tggtcctgac aagcggcatc gtgttcgtga tcagcggcgt gctgacactg atccccgtgt      480
gctggaccgc ccacgccatc atccgggact ctacaaccc tctggtggcc gaggcccaga      540
agagagagct gggcgccagc ctgtatctgg gatgggccgc ctcaggactg ctgctgctgg      600
gcggaggcct gctgtgctgt acatgtccta gcggcggctc ccagggccct agccactaca      660
tggcccggta cagcaccagc gcccctgcca tcagcagagg cccagcgag taccccacca      720
agaactacgt gtgataggaa ttcgagctct tatggcgcgc caattcgcc ctatagtgag      780
```

<210> SEQ ID NO 11
<211> LENGTH: 165
<212> TYPE: DNA
<213> ORGANISM: Artificial
<220> FEATURE:
<223> OTHER INFORMATION: synthetic nucleic acid

<400> SEQUENCE: 11

```
ggcgcgccaa ggtaccaagc ttgccaccat ggaaaccgac accctgctgc tgtgggtgct       60
gctcctgtgg gtcccaggct ctacaggcga cgccgcccag cccagagact tctacaaccc      120
cctggtggcc gaggcccaga agctcgagtc tagagggtta attaa                      165
```

<210> SEQ ID NO 12
<211> LENGTH: 38
<212> TYPE: PRT
<213> ORGANISM: Artificial
<220> FEATURE:
<223> OTHER INFORMATION: synthetic peptide

<400> SEQUENCE: 12

```
Met Glu Thr Asp Thr Leu Leu Leu Trp Val Leu Leu Leu Trp Val Pro
1               5                   10                  15
Gly Ser Thr Gly Asp Ala Ala Gln Pro Arg Asp Phe Tyr Asn Pro Leu
            20                  25                  30
Val Ala Glu Ala Gln Lys
        35
```

<210> SEQ ID NO 13
<211> LENGTH: 20

```
<212> TYPE: DNA
<213> ORGANISM: Artificial
<220> FEATURE:
<223> OTHER INFORMATION: Oligonucleotide

<400> SEQUENCE: 13
tccatgacgt tcctgacgtt                                              20
```

CANCER THERAPY USING CLDN6 TARGET-DIRECTED ANTIBODIES IN VIVO

This application is a continuation of U.S. patent application Ser. No. 15/206,039, now U.S. Pat. No. 9,902,778, which was filed on Jul. 8, 2016 as a divisional of U.S. patent application Ser. No. 13/808,423, now U.S. Pat. No. 9,718,886, which was filed on Mar. 18, 2013 as a National Stage Entry of PCT/EP2011/003312, which was filed on Jul. 4, 2011 and claimed priority to European Patent Application Number 10006957.4 and U.S. Patent Application Ser. No. 61/361,632, which were filed on Jul. 6, 2010. The contents of each of the aforementioned applications are incorporated herein by reference in their entireties.

Cancer is a significant health problem throughout the world and is still among the leading causes of death. Cancer cells biologically differ substantially from their nonmalignant cells of origin. These differences are due to genetic alterations acquired during cancer development and result, inter alia, also in the formation of qualitatively or quantitatively altered molecular structures in the cancer cells. Cancer-associated structures of this kind are, in particular, genetic products the expression of which is induced or enhanced during the course of malignant transformation.

The immune system has the ability to recognize and destroy cells via two separate modalities: innate and adaptive immunity. The innate component consists of macrophages, natural killer (NK) cells, monocytes, and granulocytes. These cells identify molecular patterns involved in cellular transformation and release various cytokines and inflammatory mediators. The innate response lacks the memory capability for foreign antigens, a feature present in adaptive immune response. This latter component of the immune system also features specificity for foreign antigens, imparted by the presence of receptors on lymphocytes. Antigen presenting cells (APCs) also play a role in the adaptive response—they engulf foreign antigens and present them to the lymphocytes in the context of major histocompatibility complex. CD4+ T cells bear receptors that recognize antigens in the context of MHC class II molecules, which then enables them to release cytokines and further activate CD8+ lymphocytes (cytotoxic T lymphocytes; CTLs) or B cells. CTLs are part of cell-mediated immunity and are capable of eliminating cells presented in the context of MHC class I molecules, via apoptosis or perforin-mediated cell lysis. It is widely accepted that T-cell mediated immunity plays a vital role in an anti-tumor response. B cells are involved in release of immunoglobulins and as such are part of the humoral immune system.

If properly aimed and enhanced, immune functions can be therapeutically exploited to control and even eradicate malignant lesions. Genetic and epigenetic changes involved in carcinogenesis generate antigens that are recognized by the immune system in analogous fashion to microbial antigens.

Antibodies have been successfully introduced into the clinic for use in cancer therapy and have emerged as the most promising therapeutics in oncology over the last decade. Antibody-based therapies for cancer have the potential of higher specificity and lower side effect profile as compared to conventional drugs. The reason is a precise distinction between normal and neoplastic cells by antibodies and the fact that their mode of action relies on less toxic immunological anti-tumor mechanisms, such as complement activation and recruitment of cytotoxic immune cells.

Claudins are integral membrane proteins located within the tight junctions of epithelia and endothelia. Claudins are predicted to have four transmembrance segments with two extracellular loops, and N- and C-termini located in the cytoplasm. The claudin (CLDN) family of transmembrane proteins plays a critical role in the maintenance of epithelial and endothelial tight junctions and might also play a role in the maintenance of the cytoskeleton and in cell signaling.

We have found that CLDN6 is expressed in tissues of various cancers while expression in normal non-cancer tissues is limited to placenta. Such cancers include ovarian cancer, in particular ovarian adenocarcinoma and ovarian teratocarcinoma, lung cancer, including small cell lung cancer (SCLC) and non-small cell lung cancer (NSCLC), in particular squamous cell lung carcinoma and adenocarcinoma, gastric cancer, breast cancer, hepatic cancer, pancreatic cancer, skin cancer, in particular basal cell carcinoma and squamous cell carcinoma, malignant melanoma, head and neck cancer, in particular malignant pleomorphic adenoma, sarcoma, in particular synovial sarcoma and carcinosarcoma, bile duct cancer, cancer of the urinary bladder, in particular transitional cell carcinoma and papillary carcinoma, kidney cancer, in particular renal cell carcinoma including clear cell renal cell carcinoma and papillary renal cell carcinoma, colon cancer, small bowel cancer, including cancer of the ileum, in particular small bowel adenocarcinoma and adenocarcinoma of the ileum, testicular embryonal carcinoma, placental choriocarcinoma, cervical cancer, testicular cancer, in particular testicular seminoma, testicular teratoma and embryonic testicular cancer, and uterine cancer, and the metastatic forms thereof.

Furthermore, we were able to produce antibodies capable of specifically binding to CLDN6 on the surface of intact cells expressing CLDN6. No binding to cells expressing claudin proteins other than CLDN6, in particular, CLDN3, CLDN4 and CLDN9, or cells not expressing any of these CLDN proteins was observed for these antibodies.

Here, we extend those observations by demonstrating that antibody binding to CLDN6 on the surface of tumor cells is sufficient in conferring a significant tumor growth inhibition. In vivo assessment of tumor growth of tumor cells transfected with CLDN6 and non-transfected xenografts showed the specific inhibition of tumor growth of CLDN6-transfected cells mediated by antibody binding to CLDN6. Furthermore, it was demonstrated that antibody binding to CLDN6 is sufficient in inhibiting tumor growth in vivo of endogenously CLDN6 expressing tumor cells. This establishes the proof-of-principle that antibody binding to CLDN6 is effective in inhibiting tumor growth, and provides evidence that CLDN6 is an attractive target for therapeutic antibodies designed to inhibit tumor growth by targeting CLDN6.

Furthermore, it was demonstrated that antibody binding to CLDN6 is efficient in inhibiting tumor growth of a human CLDN6 positive germ cell tumor cell line in vivo demonstrating the usefulness of antibodies binding to CLDN6 as selective therapeutic agents to target and induce the killing of germ cell tumors such as testicular germ cell tumors.

Thus, we provide the first direct evidence that antibody binding to CLDN6 on the surface of tumor cells in vivo results in tumor growth attenuation and provide the demonstration that specific binding to CLDN6 results in a therapeutic intervention by which tumor growth is attenuated. Furthermore, we provide evidence that antibody binding to CLDN6 on the surface of tumor cells in vivo results in the prolongation of survival and extending the lifespan of tumor patients.

Accordingly, the invention relates to the treatment and/or prevention of tumor diseases associated with cells expressing CLDN6, in particular cancer and cancer metastasis using antibodies which bind to CLDN6. The present application demonstrates that the binding of antibodies to CLDN6 on the surface of tumor cells is sufficient to inhibit growth of the tumor and to prolong survival and extend the lifespan of tumor patients. Furthermore, binding of antibodies to CLDN6 is efficient in inhibiting growth of CLDN6 positive germ cell tumors such as teratocarcinomas or embryonal carcinomas, in particular germ cell tumors of the testis.

BRIEF SUMMARY OF THE INVENTION

In one aspect, the invention relates to an antibody which inhibits growth of a tumor in vivo, wherein the cells of the tumor express claudin 6 (CLDN6) and wherein the antibody is capable of binding to CLDN6. In one embodiment, the antibody inhibits growth of the tumor by binding to CLDN6. In one embodiment, the antibody is specific for CLDN6. In one embodiment, the antibody is a monoclonal, chimeric, human or humanized antibody, or is a fragment of an antibody or a synthetic antibody. The tumor may be selected from the group consisting of ovarian cancer, in particular ovarian adenocarcinoma and ovarian teratocarcinoma, lung cancer, including small cell lung cancer (SCLC) and non-small cell lung cancer (NSCLC), in particular squamous cell lung carcinoma and adenocarcinoma, gastric cancer, breast cancer, hepatic cancer, pancreatic cancer, skin cancer, in particular basal cell carcinoma and squamous cell carcinoma, malignant melanoma, head and neck cancer, in particular malignant pleomorphic adenoma, sarcoma, in particular synovial sarcoma and carcinosarcoma, bile duct cancer, cancer of the urinary bladder, in particular transitional cell carcinoma and papillary carcinoma, kidney cancer, in particular renal cell carcinoma including clear cell renal cell carcinoma and papillary renal cell carcinoma, colon cancer, small bowel cancer, including cancer of the ileum, in particular small bowel adenocarcinoma and adenocarcinoma of the ileum, testicular embryonal carcinoma, placental choriocarcinoma, cervical cancer, testicular cancer, in particular testicular seminoma, testicular teratoma and embryonic testicular cancer, and uterine cancer, and the metastatic forms thereof. The tumor may be a germ cell tumor such as a teratocarcinoma or an embryonal carcinoma. The germ cell tumor may be a germ cell tumor of the testis.

In a further aspect, the invention relates to an antibody selected from the group consisting of (i) an antibody produced by or obtainable from a clone deposited under the accession no. DSM ACC3059 (GT512muMAB 36A), DSM ACC3058 (GT512muMAB 27A), or DSM ACC3057 (GT512muMAB 5F2D2), (ii) an antibody which is a chimerized or humanized form of the antibody under (i), (iii) an antibody which has the specificity of the antibody under (i), and (iv) an antibody comprising the antigen binding portion or antigen binding site of the antibody under (i). The antigen binding portion or antigen binding site of the antibody under (i) may comprise the variable region of the antibody under (i).

The antibody according to any of the above aspects may be attached to at least one therapeutic effector moiety such as a radiolabel, cytotoxin or cytotoxic enzyme.

In a further aspect, the invention relates to a hybridoma capable of producing the antibody according to any of the above aspects.

In a further aspect, the invention relates to a hybridoma deposited under the accession no. DSM ACC3059 (GT512muMAB 36A), DSM ACC3058 (GT512muMAB 27A), or DSM ACC3057 (GT512muMAB 5F2D2).

In a further aspect, the invention relates to a pharmaceutical composition comprising the antibody according to any of the above aspects. The pharmaceutical composition may in the form of a therapeutic or prophylactic tumor vaccine. In one embodiment, the pharmaceutical composition is for use in treating or preventing a tumor disease.

In a further aspect, the invention relates to a method of treating a patient having a tumor disease or being at risk of developing a tumor disease, wherein the cells of the tumor express claudin 6 (CLDN6) and wherein the method comprises the administration of an antibody capable of binding to CLDN6. In one embodiment, the antibody when administered to the patient inhibits growth of the tumor in the patient by binding to CLDN6. In one embodiment, the antibody is attached to at least one therapeutic effector moiety such as a radiolabel, cytotoxin or cytotoxic enzyme. The antibody may be specific for CLDN6. The antibody may be a monoclonal, chimeric, human or humanized antibody, or a fragment of an antibody or a synthetic antibody. In one embodiment the method comprises the administration of a pharmaceutical composition according to any of the above aspects.

In any of the above aspects, the tumor disease may be selected from the group consisting of ovarian cancer, in particular ovarian adenocarcinoma and ovarian teratocarcinoma, lung cancer, including small cell lung cancer (SCLC) and non-small cell lung cancer (NSCLC), in particular squamous cell lung carcinoma and adenocarcinoma, gastric cancer, breast cancer, hepatic cancer, pancreatic cancer, skin cancer, in particular basal cell carcinoma and squamous cell carcinoma, malignant melanoma, head and neck cancer, in particular malignant pleomorphic adenoma, sarcoma, in particular synovial sarcoma and carcinosarcoma, bile duct cancer, cancer of the urinary bladder, in particular transitional cell carcinoma and papillary carcinoma, kidney cancer, in particular renal cell carcinoma including clear cell renal cell carcinoma and papillary renal cell carcinoma, colon cancer, small bowel cancer, including cancer of the ileum, in particular small bowel adenocarcinoma and adenocarcinoma of the ileum, testicular embryonal carcinoma, placental choriocarcinoma, cervical cancer, testicular cancer, in particular testicular seminoma, testicular teratoma and embryonic testicular cancer, and uterine cancer, and the metastatic forms thereof.

In any of the above aspects, the tumor disease may be a germ cell tumor disease such as a disease characterized by a teratocarcinoma or an embryonal carcinoma. The germ cell tumor disease may be a germ cell tumor disease of the testis.

In any of the above aspects, the CLDN6 may comprise an amino acid sequence encoded by a nucleic acid which comprises the nucleic acid sequence according to SEQ ID NO: 1 of the sequence listing or a variant of said nucleic acid sequence and/or may comprises the amino acid sequence according to SEQ ID NO: 2 of the sequence listing or a variant of said amino acid sequence.

An antibody described herein is capable of binding to CLDN6 and is preferably capable of binding to CLDN6 associated with the surface of a cell that expresses CLDN6. Preferably, the antibody is not substantially capable of binding to CLDN3, in particular when associated with the surface of a cell that expresses CLDN3, and/or is not substantially capable of binding to CLDN4, in particular when associated with the surface of a cell that expresses CLDN4. Preferably, the antibody is not substantially capable of binding to CLDN9, in particular when associated with the surface of a cell that expresses CLDN9. Most preferably, the antibody is not substantially capable of binding to a CLDN protein other than CLDN6, in particular when associated with the surface of a cell that expresses said CLDN protein, and is specific for CLDN6. Preferably, said cell expressing said CLDN protein is an intact cell, in particular a non-permeabilized cell, and said CLDN protein associated with the surface of a cell has a native, i.e. non-denatured, conformation. Preferably, the antibody is capable of binding to one or more epitopes of CLDN6 in their native conformation.

In particular preferred embodiments, an antibody described herein binds to native epitopes of CLDN6 present on the surface of living cells such as those of SEQ ID NO: 3, SEQ ID NO: 4 or SEQ ID NO: 5. In further preferred embodiments, the antibody is specific for CLDN6-expressing tumor cells and does not bind to tumor cells not expressing CLDN6. Preferably, an antibody described herein specifically binds to CLDN6.

In one embodiment, an antibody described herein is capable of binding to an epitope located within an extracellular portion of CLDN6, wherein said extracellular portion of CLDN6 preferably comprises the amino acid sequence of SEQ ID NO: 3, SEQ ID NO: 4 or SEQ ID NO: 5, more preferably the amino acid sequence of SEQ ID NO: 5. Preferably, the antibody is capable of binding to an epitope located within the amino acid sequence of SEQ ID NO: 5.

In one embodiment, the antibody is obtainable by a method comprising the step of immunizing an animal with a peptide having the amino acid sequence of SEQ ID NO: 3, SEQ ID NO: 4 or SEQ ID NO: 5, more preferably the amino acid sequence of SEQ ID NO: 5 or an immunologically equivalent peptide, or a nucleic acid or host cell expressing said peptide.

In different embodiments, the CLDN6 to which the antibody is capable of binding has the amino acid sequence of SEQ ID NO: 2 or the amino acid sequence of SEQ ID NO: 6. It is particularly preferred that the antibody is capable of binding to CLDN6 having the amino acid sequence of SEQ ID NO: 2 and capable of binding to CLDN6 having the amino acid sequence of SEQ ID NO: 6.

In preferred embodiments, an antibody described herein has one or more of the following activities: (i) killing of a cell expressing CLDN6, (ii) inhibition of proliferation of a cell expressing CLDN6, (iii) inhibition of colony formation of a cell expressing CLDN6, and (iv) inhibition of metastasis of a cell expressing CLDN6. Killing of cells, inhibition of proliferation of cells and/or inhibition of colony formation of cells can be utilized therapeutically for inhibiting tumor growth which includes stopping and/or preventing tumor growth, retarding tumor growth and/or reducing the size of an existing tumor and thus, can be utilized therapeutically for treating or preventing cancer, cancer metastasis and/or the metastatic spread of cancer cells.

Preferably an antibody described herein mediates killing of cells by inducing complement dependent cytotoxicity (CDC) mediated lysis, antibody dependent cellular cytotoxicity (ADCC) mediated lysis, apoptosis, homotypic adhesion, and/or phagocytosis, preferably by inducing CDC mediated lysis and/or ADCC mediated lysis.

Preferably, ADCC mediated lysis of cells takes place in the presence of effector cells, which in particular embodiments are selected from the group consisting of monocytes, mononuclear cells, NK cells and PMNs, and phagocytosis is by macrophages.

The activity of inhibiting or reducing proliferation of cells expressing CLDN6, preferably cancer cells, can be measured in vitro by determining proliferation of CLDN6-expressing cancer cells in an assay using bromodeoxyuridine (5-bromo-2-deoxyuridine, BrdU). BrdU is a synthetic nucleoside which is an analogue of thymidine and can be incorporated into the newly synthesized DNA of replicating cells (during the S phase of the cell cycle), substituting for thymidine during DNA replication. Detecting the incorporated chemical using, for example, antibodies specific for BrdU indicates cells that were actively replicating their DNA.

The activity of inhibiting or reducing colony formation of cells expressing CLDN6, preferably cancer cells, can be measured in vitro in a clonogenic assay. A clonogenic assay is a microbiology technique for studying the effectiveness of specific agents on the survival and proliferation of cells. It is frequently used in cancer research laboratories to determine the effect of drugs or radiation on proliferating tumor cells. The experiment involves three major steps: (i) applying a treatment to a sample of cells, in particular cancer cells, (ii) plating the cells in a tissue culture vessel and (iii) allowing the cells to grow. The colonies produced are fixed, stained, and counted. Colony formation is of importance with respect to the formation of metastases if individual tumor cells colonize organs. The inhibitory activity of the antibodies indicates their potential in suppressing the formation of metastases. Antibodies having the activity of inhibiting or reducing colony formation in a clonogenic assay are particularly useful for treating or preventing metastasis and the metastatic spread of cancer cells, in particular of the cancer types mentioned herein.

In preferred embodiments, an antibody described herein exhibits one or more immune effector functions against a cell carrying CLDN6 in its native conformation, wherein the one or more immune effector functions are preferably selected from the group consisting of complement dependent cytotoxicity (CDC), antibody-dependent cell-mediated cytotoxicity (ADCC), induction of apoptosis, and inhibition of proliferation, preferably the effector functions are ADCC and/or CDC.

Preferably tumor growth inhibition or immune effector functions exerted by an antibody described herein are induced by binding of said antibody to CLDN6, preferably to an epitope located within an extracellular portion of CLDN6, wherein said extracellular portion of CLDN6 preferably comprises the amino acid sequence of SEQ ID NO: 3, SEQ ID NO: 4 or SEQ ID NO: 5, more preferably the amino acid sequence of SEQ ID NO: 5.

According to the invention, a cell expressing CLDN6 is preferably characterized by association of CLDN6 with its cell surface. A cell expressing CLDN6 or a cell characterized by association of CLDN6 with its cell surface or carrying CLDN6 in its native conformation preferably is a tumor cell, such as a cancer cell, preferably a cancer cell from a cancer described herein.

An antibody described herein may be attached to one or more therapeutic effector moieties, e.g., radiolabels, cytotoxins, therapeutic enzymes, agents that induce apoptosis, and the like in order to provide for targeted cytotoxicity, i.e., killing of tumor cells.

In one embodiment an antibody described herein (i) binds to cells expressing CLDN6, and (ii) does not bind to cells not expressing CLDN6. An antibody described herein preferably (i) mediates killing and/or inhibits proliferation of cells expressing CLDN6, and (ii) does not mediate killing and/or does not inhibit proliferation of cells not expressing CLDN6.

In one embodiment, an antibody described herein can be characterized by one or more of the following properties:
a) specificity for CLDN6;
b) a binding affinity to CLDN6 of about 100 nM or less, preferably, about 5-10 nM or less and, more preferably, about 1-3 nM or less;
c) the ability to deplete tumor cells which express CLDN6;
d) the ability to stop or retard proliferation of tumor cells which express CLDN6;
e) the ability to prolong survival of a subject having tumor cells which express CLDN6.

In one embodiment, an antibody described herein reduces tumor cell growth and/or induces tumor cell death and thus, has a tumor-inhibiting or tumor-destroying effect.

A preferred antibody described herein is an antibody produced by or obtainable from a hybridoma cell deposited at the DSMZ (Inhoffenstr. 7B, 38124 Braunschweig, Germany) and having one of the following designations and accession numbers:
1. GT512muMAB 36A, accession no. DSM ACC3059, deposited on Apr. 13, 2010;
2. GT512muMAB 27A, accession no. DSM ACC3058, deposited on Apr. 13, 2010; or
3. GT512muMAB 5F2D2, accession no. DSM ACC3057, deposited on Apr. 13, 2010.

Antibodies of the invention are designated herein by referring to the designation of the antibody and/or by referring to the clone producing the antibody, e.g. muMAB 36A.

Further preferred antibodies are those having the specificity of the antibodies produced by and obtainable from the above-described hybridomas and, in particular, those comprising an antigen binding portion or antigen binding site, in particular a variable region, identical or highly homologous to that of the antibodies produced by and obtainable from the above-described hybridomas. It is contemplated that preferred antibodies are those having CDR regions either identical or highly homologous to the regions of antibodies produced by and obtainable from the above-described hybridomas. By "highly homologous" it is contemplated that from 1 to 5, preferably from 1 to 4, such as 1 to 3 or 1 or 2 substitutions may be made. Particularly preferred antibodies are the chimerized and humanized forms of the antibodies produced by and obtainable from the above-described hybridomas.

The present invention also relates to a cell such as a hybridoma cell producing an antibody as described herein.

Preferred hybridoma cells are those deposited at the DSMZ (Inhoffenstr. 7B, 38124 Braunschweig, Germany) and having one of the following designations and accession numbers:
1. GT512muMAB 36A, accession no. DSM ACC3059, deposited on Apr. 13, 2010;
2. GT512muMAB 27A, accession no. DSM ACC3058, deposited on Apr. 13, 2010; or
3. GT512muMAB 5F2D2, accession no. DSM ACC3057, deposited on Apr. 13, 2010.

The present invention also relates to nucleic acids comprising genes or nucleic acid sequences encoding antibodies or parts thereof, e.g. an antibody chain, as described herein. The nucleic acids may be comprised in a vector, e.g., a plasmid, cosmid, virus, bacteriophage or another vector used e.g. conventionally in genetic engineering. The vector may comprise further genes such as marker genes which allow for the selection of the vector in a suitable host cell and under suitable conditions. Furthermore, the vector may comprise expression control elements allowing proper expression of the coding regions in suitable hosts. Such control elements are known to the artisan and may include a promoter, a splice cassette, and a translation initiation codon.

Preferably, the nucleic acid of the invention is operatively attached to expression control elements allowing expression in eukaryotic or prokaryotic cells. Control elements ensuring expression in eukaryotic or prokaryotic cells are well known to those skilled in the art.

Methods for construction of nucleic acid molecules, for construction of vectors comprising nucleic acid molecules, for introduction of vectors into appropriately chosen host cells, or for causing or achieving expression of nucleic acid molecules are well-known in the art.

A further aspect of the present invention relates to a host cell comprising a nucleic acid or vector as disclosed herein.

In one aspect, the invention provides compositions, e.g., pharmaceutical and diagnostic compositions/kits, comprising an antibody or a combination of antibodies described herein. A pharmaceutical composition of the invention may comprise a pharmaceutically acceptable carrier and may optionally comprise one or more adjuvants, stabilizers etc. In a particular embodiment, the composition includes a combination of antibodies which bind to distinct epitopes or which possess distinct functional characteristics, such as inducing CDC and/or ADCC.

In one embodiment, the pharmaceutical composition of the present invention is a therapeutic or prophylactic anti-tumor vaccine.

In one aspect, the invention provides therapeutic and prophylactic methods of treating a patient having a tumor disease or being at risk of developing a tumor disease. In one aspect, the invention provides methods for inhibiting tumor growth. In one aspect, the invention provides methods for inducing tumor cell death. These aspects may involve the administration of the antibodies or compositions described herein to a patient.

The present invention also includes the simultaneous or sequential administration of two or more anti-CLDN6 antibodies, wherein preferably at least one of said antibodies is a chimeric anti-CLDN6 antibody and at least one further antibody is a human anti-CLDN6 antibody, the antibodies binding to the same or different epitopes of CLDN6. Preferably, a chimeric CLDN6 antibody of the invention is administered first followed by the administration of a human anti-CLDN6 antibody, wherein the human anti-CLDN6 antibody is preferably administered for an extended period of time, i.e. as maintenance therapy.

An antibody or a composition described herein can be used in a variety of methods for inhibiting growth of tumor cells expressing CLDN6 and/or selectively killing tumor cells expressing CLDN6 and thus inhibiting tumor growth by contacting the cells with an effective amount of the antibody or composition, such that the growth of the cell is inhibited and/or the cell is killed. In one embodiment, the method includes killing of the tumor cell expressing CLDN6, optionally in the presence of effector cells, for example, by CDC, apoptosis, ADCC, phagocytosis, or by a combination of two or more of these mechanisms.

An antibody or a composition described herein can be used to treat and/or prevent tumor diseases involving cells expressing CLDN6 by administering the antibody or composition to patients suffering from or being at risk of developing such diseases.

The invention may involve a prophylactic and/or therapeutic treatment of tumor diseases, i.e. for treating a patient having a tumor disease or being at risk of developing a tumor disease. In one aspect, the invention provides methods for inhibiting tumor growth comprising the administration of one or more of the antibodies and compositions described herein.

Preferably, the antibodies and compositions described herein are administered in a way such that the therapeutically active substance, in particular the antibody, is not delivered or not substantially delivered to a tissue or organ wherein the cells when the tissue or organ is free of tumors express CLDN6 such as placenta tissue or placenta. To this end, the agents and compositions described herein can be administered locally.

In one aspect, the invention provides an antibody as described herein for use in the methods of treatment described herein. In one embodiment, the invention provides a pharmaceutical composition as described herein for use in the methods of treatment described herein.

The treatments described herein can be combined with surgical resection and/or radiation and/or traditional chemotherapy.

Other features and advantages of the instant invention will be apparent from the following detailed description and claims.

MuMAB 27A exhibits dose-dependent CDC activity whereas muMAB 36A is not able to induce CDC in vitro.

Figure 8:
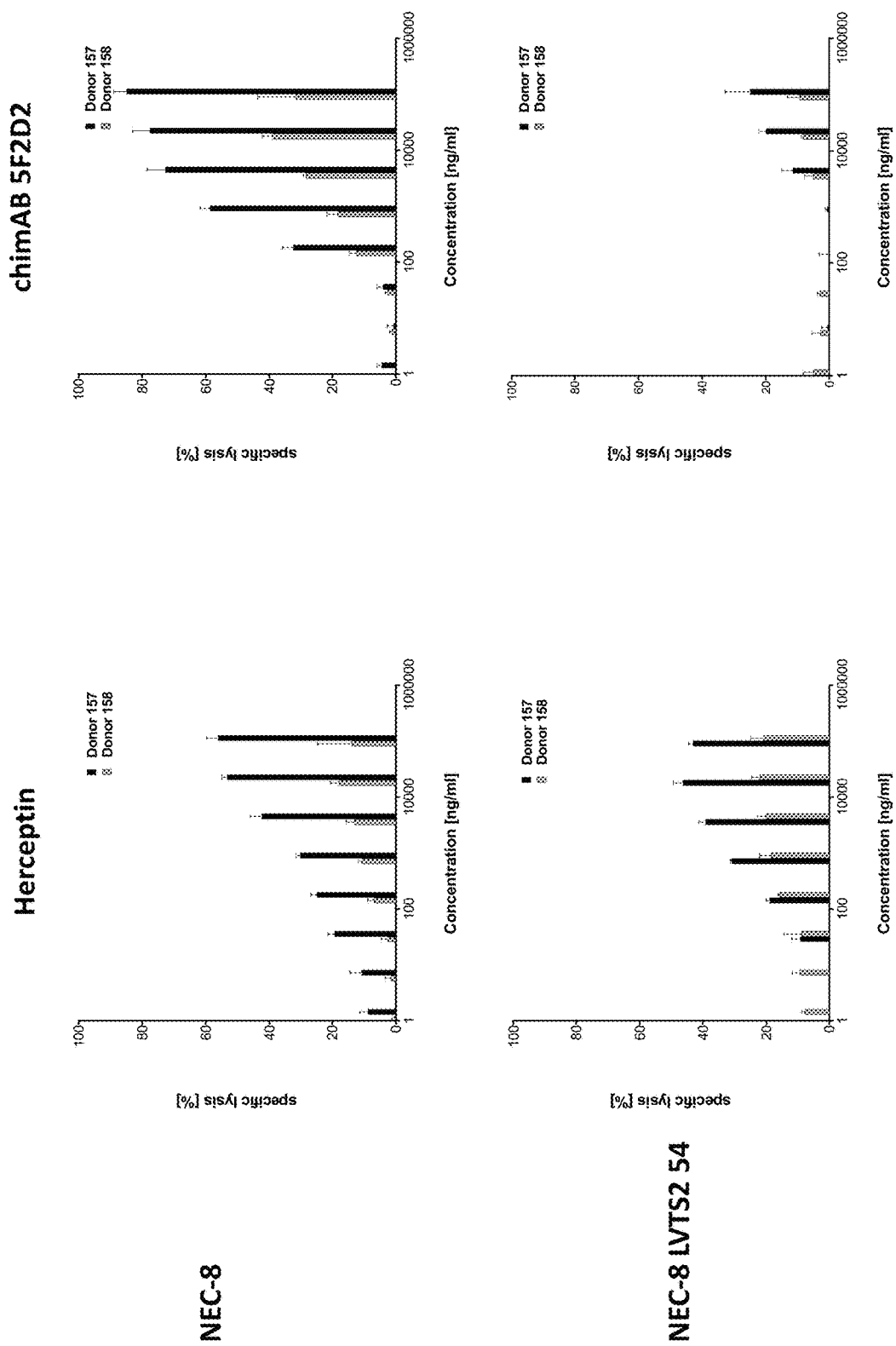

FIG. 8:
Induction of antibody-dependent cell-mediated cytotoxicity (ADCC) by the chimeric anti-CLDN6 antibody chimAB 5F2D2 on endogenously CLDN6 expressing NEC8 and NEC8 LVTS2 54 (CLDN6 knock-down).
The chimeric anti-CLDN6 antibody chimAB 5F2D2 induces ADCC on NEC8 cells with effector cells of two different donors in a dose dependent manner. The efficiency to induce ADCC on NEC8 LVTS2 54 cells (CLDN6 knock-down) is strongly decreased with chimAB 5F2D2.

Figure 9:
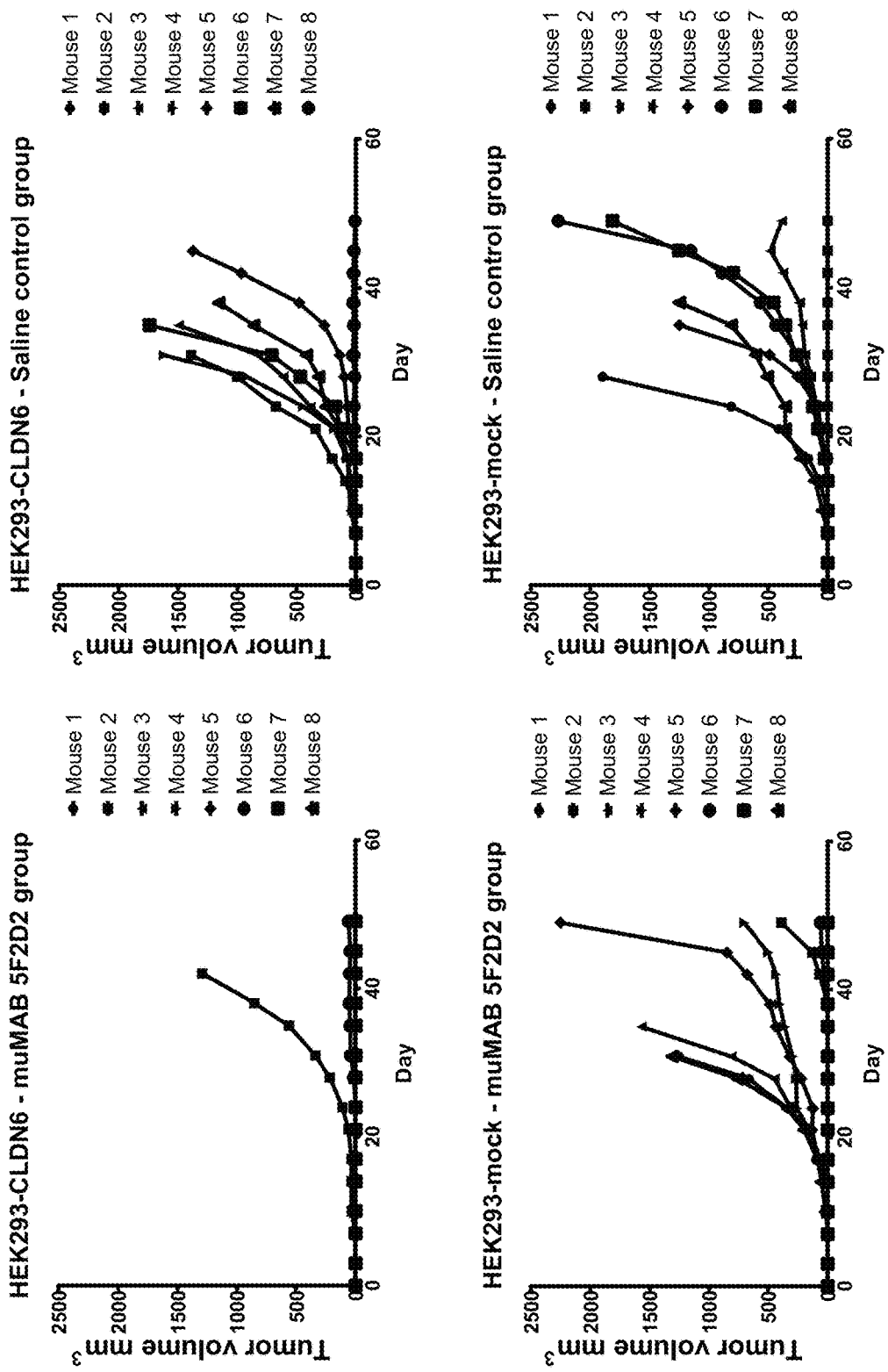

FIG. 9:
Therapeutic effect of muMAB 5F2D2 in an early treatment xenograft model.
MuMAB 5F2D2 shows specific and strong tumor growth inhibition in mice engrafted with HEK293 cells stably expressing human CLDN6.

Figure 10:
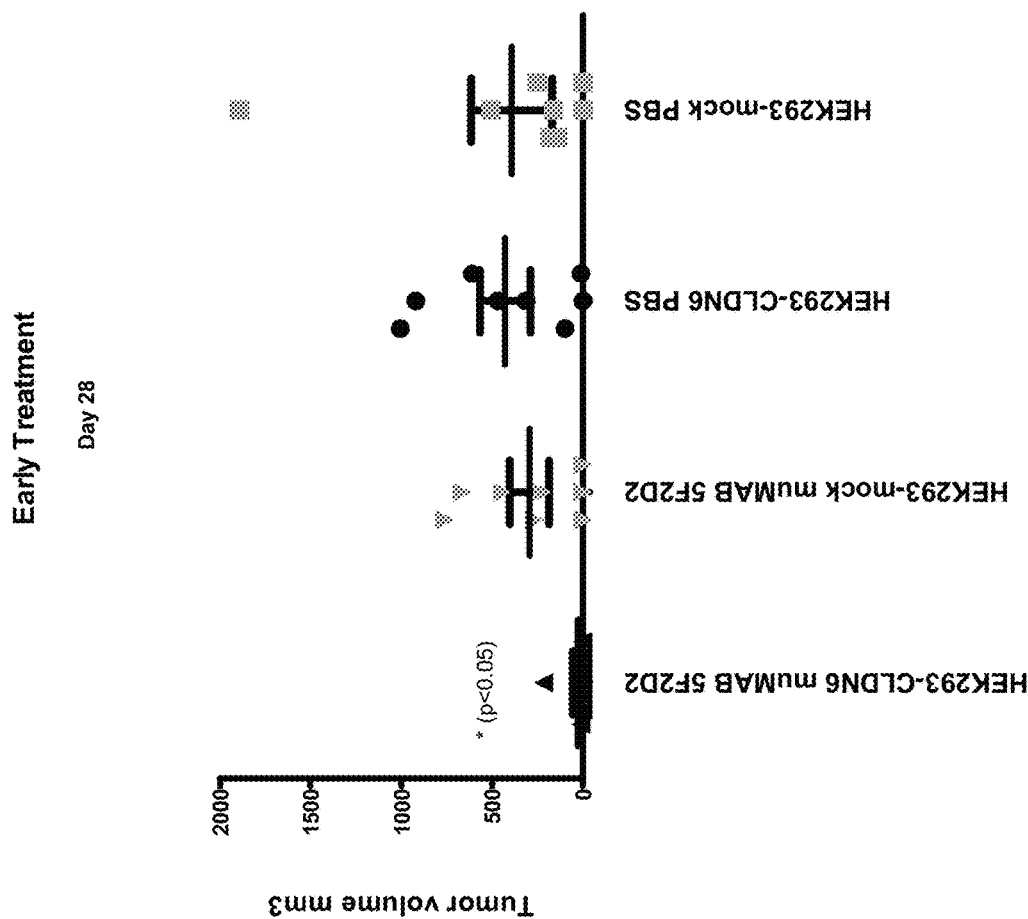

FIG. 10:
Therapeutic effect of muMAB 5F2D2 in an early treatment xenograft model.
Tumor volumes are significantly reduced at day 28 (and thereafter) after treatment with muMAB 5F2D2 in a Kruskal-Wallis test.

Figure 11:
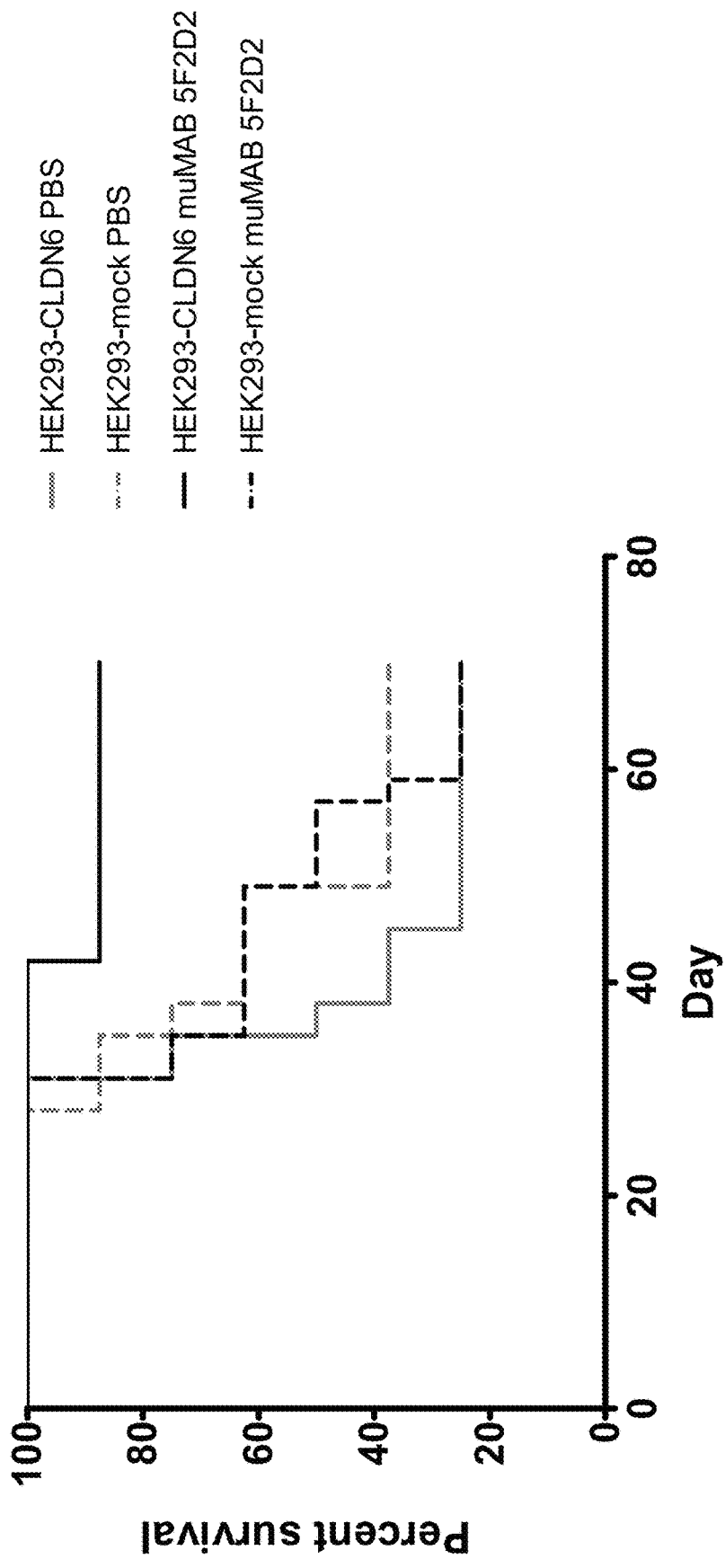

FIG. 11:
Therapeutic effect of muMAB 5F2D2 in an early treatment xenograft model.
Mice treated with the monoclonal murine anti-CLDN6 antibody muMAB 5F2D2 show prolonged survival compared to PBS control groups.

Figure 12:
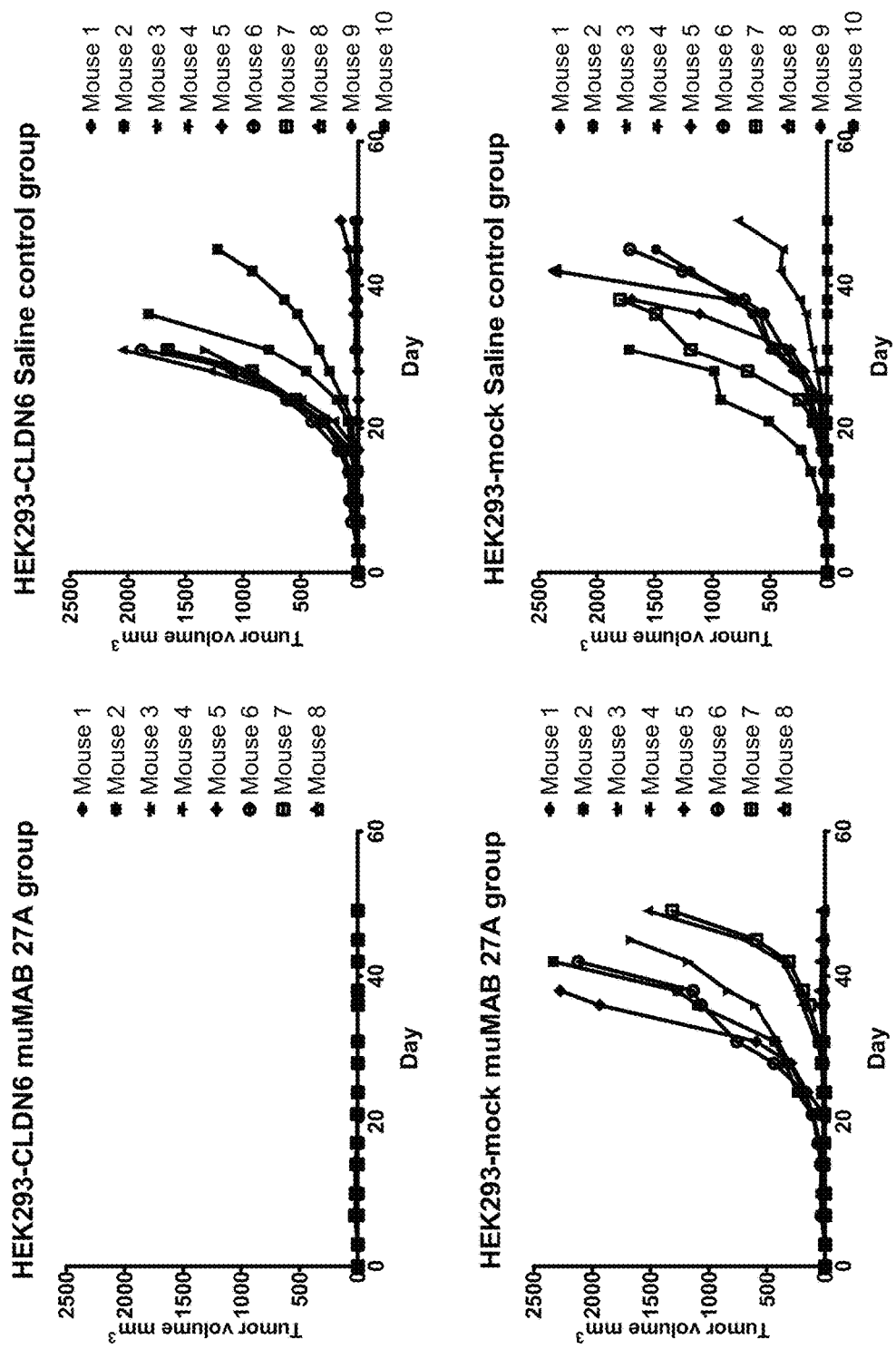

FIG. 12:
Therapeutic effect of muMAB 27A in an early treatment xenograft model.
MuMAB 27A shows specific and strong tumor growth inhibition in mice engrafted with HEK293 cells stably expressing human CLDN6.

Figure 13:
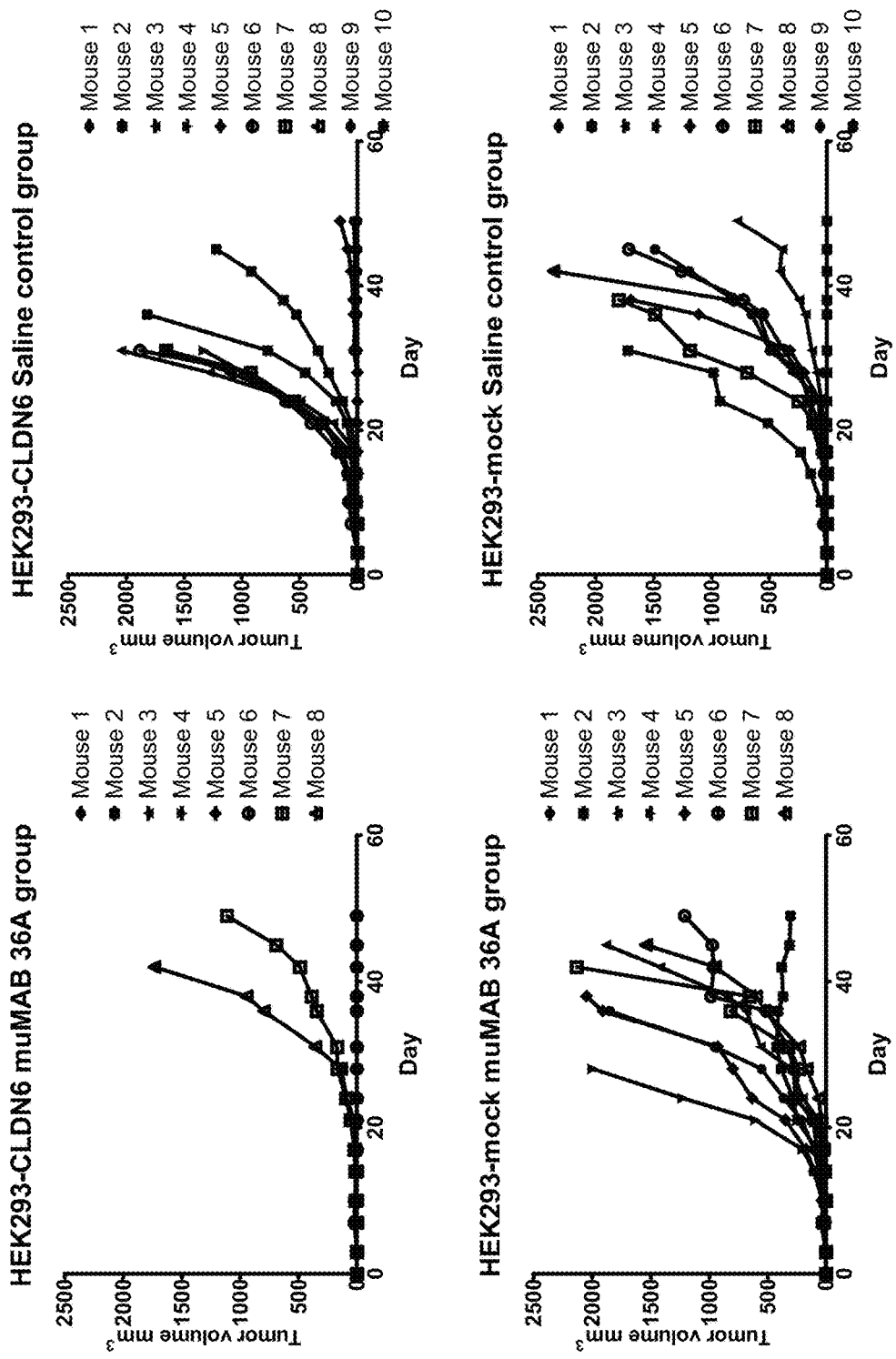

FIG. 13:
Therapeutic effect of muMAB 36A in an early treatment xenograft model.
MuMAB 36A shows specific and strong tumor growth inhibition in mice engrafted with HEK293 cells stably expressing human CLDN6.

Figure 14:
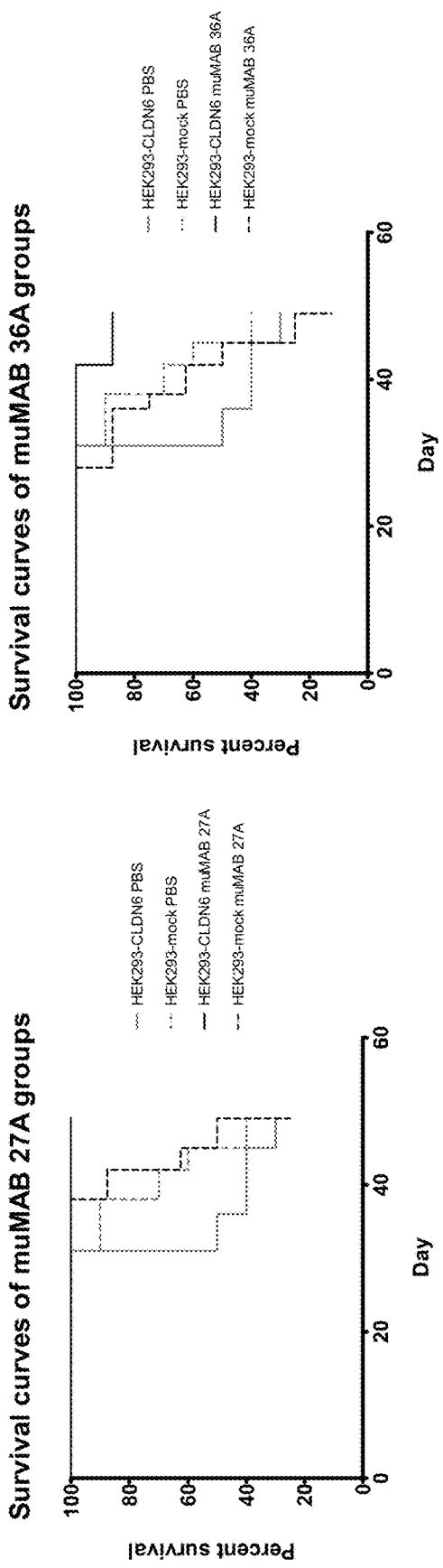

FIG. 14:
Therapeutic effect of muMAB 27A and 36A in an early treatment xenograft model.
Mice treated with the monoclonal murine anti-CLDN6 antibodies muMAB 27A and 36A show prolonged survival.

Figure 15:
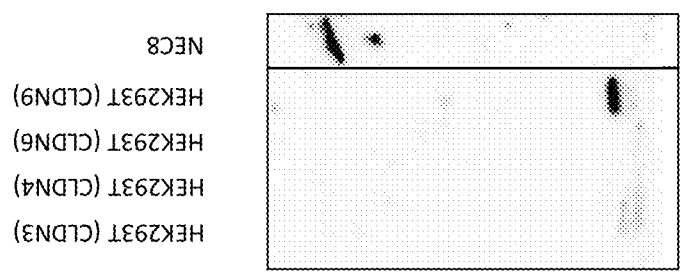
Figure 15:
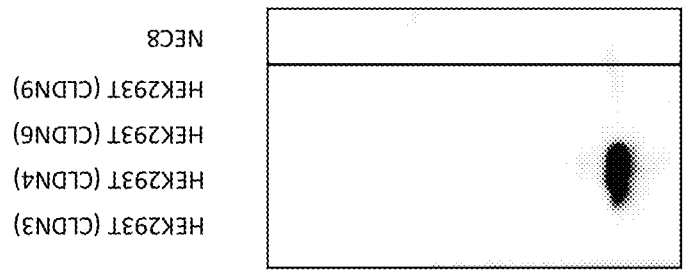
Figure 15:
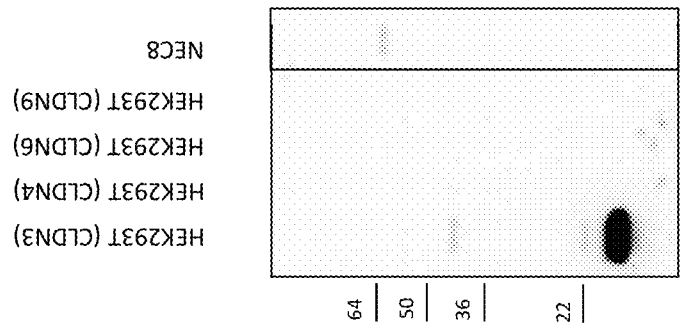
Figure 15:
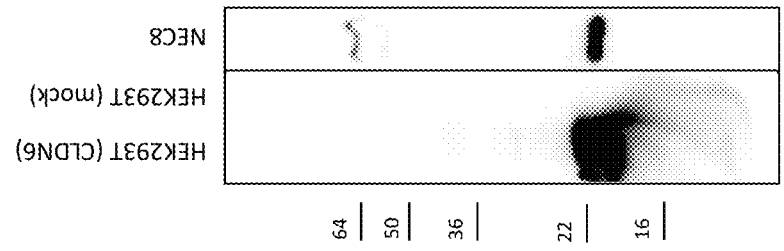

FIG. 15:
Immunoblot analysis of human CLDN3, 4, 6 and 9 expression in NEC8 cells.
The testicular germ cell tumor cell line NEC8 only shows expression of CLDN6 (left panel) but not of CLDN3, 4 or 9, respectively (right panels).

Figure 16:
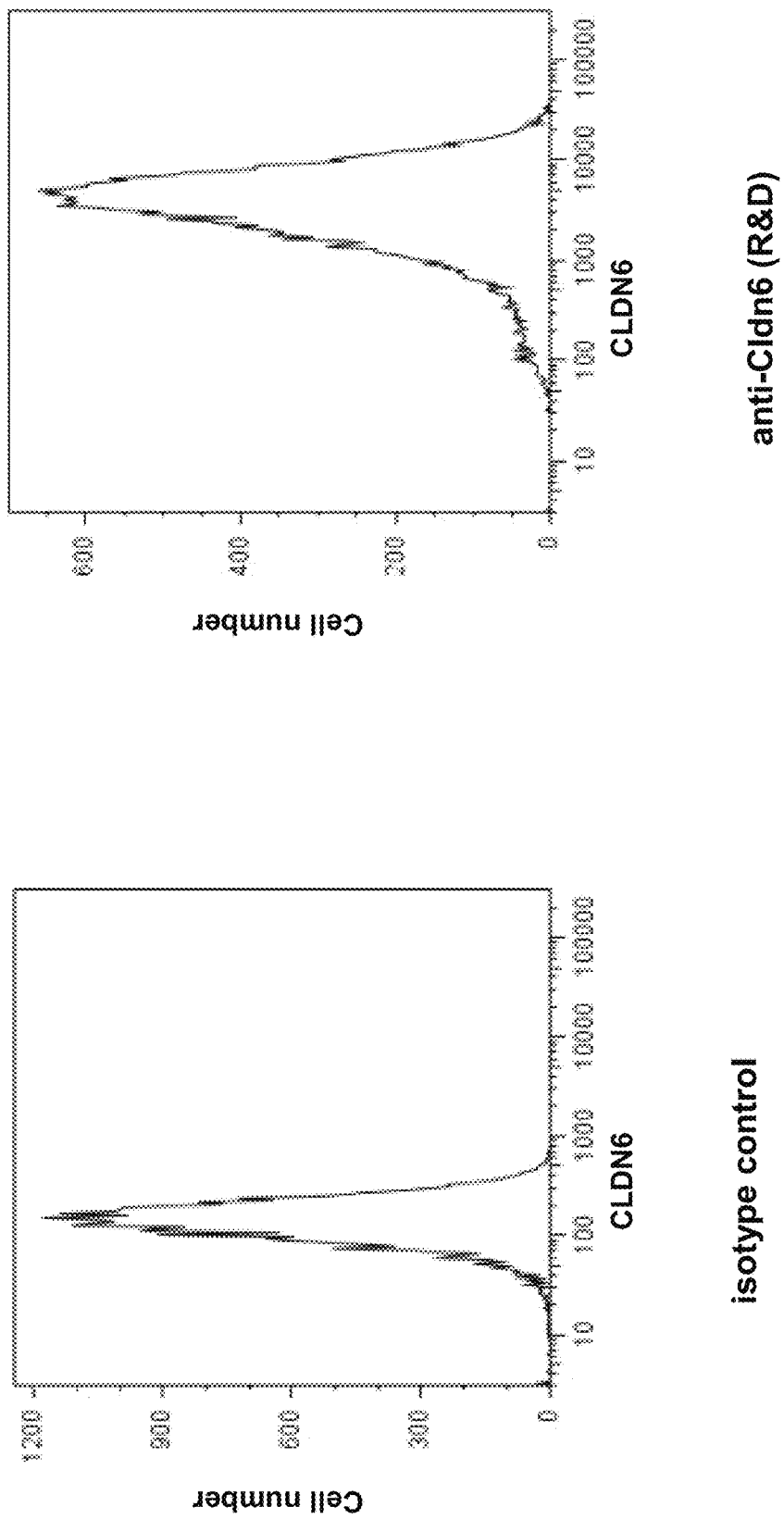

FIG. 16:
Analysis of CLDN6 surface expression on NEC8 cells using flow cytometry.
CLDN6 is expressed on NEC8 cells.

Figure 17:
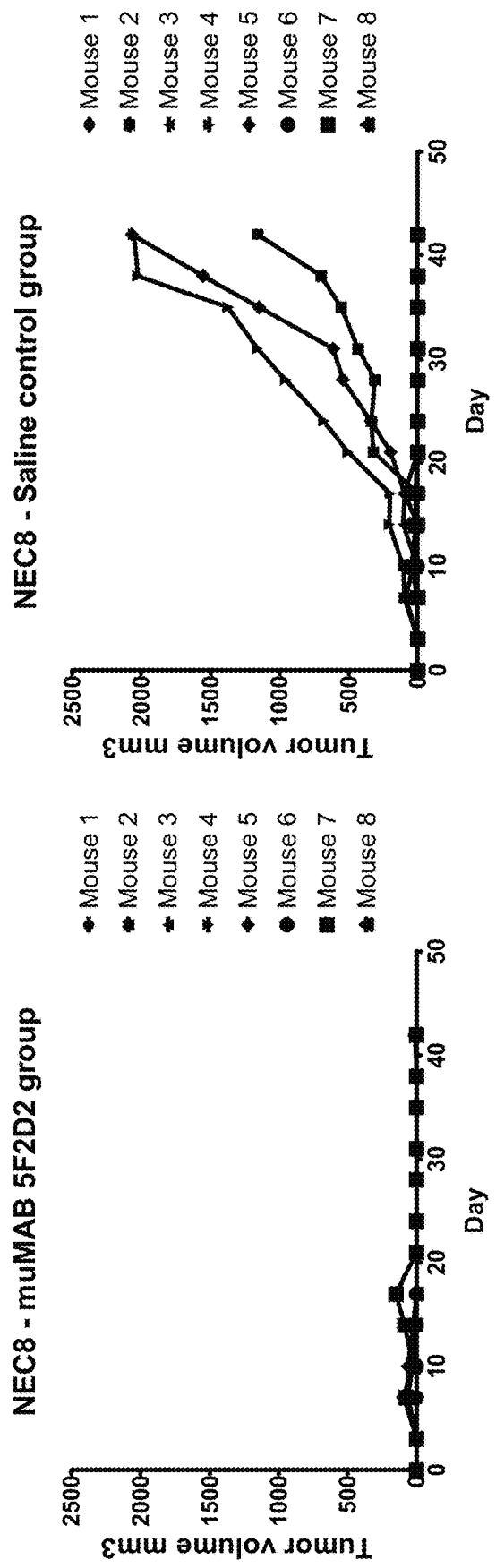

FIG. 17:
Therapeutic effect of muMAB 5F2D2 in an early treatment xenograft model using mice engrafted with the tumor cell line NEC8.

Compared to the saline control group muMAB 5F2D2 showed specific and strong tumor growth inhibition in mice engrafted with NEC8 cells that endogenously express human CLDN6.

FIG. 18:

Therapeutic effect of muMAB 5F2D2 in an early treatment xenograft model using mice engrafted with the tumor cell line NEC8.

The Kruskal-Wallis test shows that tumor volumes are reduced at day 21 and 42 after treatment with muMAB 5F2D2.

DETAILED DESCRIPTION OF THE INVENTION

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps although in some embodiments such other member, integer or step or group of members, integers or steps may be excluded, i.e. the subject-matter consists in the inclusion of a stated member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Claudins are a family of proteins that are the most important components of tight junctions, where they establish the paracellular barrier that controls the flow of molecules in the intercellular space between cells of an epithelium. Claudins are transmembrane proteins spanning the membrane 4 times with the N-terminal and the C-terminal end both located in the cytoplasm. The first extracellular loop consists on average of 53 amino acids and the second one of around 24 amino acids. CLDN6 and CLDN9 are the most similar members of the CLDN family.

The term "CLDN" as used herein means claudin and includes CLDN6, CLDN9, CLDN4 and CLDN3. Preferably, a CLDN is a human CLDN.

The term "CLDN6" preferably relates to human CLDN6, and, in particular, to a protein comprising (i) an amino acid sequence encoded by a nucleic acid which comprises the nucleic acid sequence according to SEQ ID NO: 1 of the sequence listing or a variant of said nucleic acid sequence, and/or (ii) the amino acid sequence according to SEQ ID NO: 2 or SEQ ID NO: 6 of the sequence listing or a variant of said amino acid sequence. The first extracellular loop of CLDN6 preferably comprises amino acids 28 to 80, more preferably amino acids 28 to 76 of the amino acid sequence shown in SEQ ID NO: 2 or the amino acid sequence shown in SEQ ID NO: 6, such as the amino acid sequence shown in SEQ ID NO: 3. The second extracellular loop of CLDN6 preferably comprises amino acids 138 to 160, preferably amino acids 141 to 159, more preferably amino acids 145 to 157 of the amino acid sequence shown in SEQ ID NO: 2 or the amino acid sequence shown in SEQ ID NO: 6, such as the amino acid sequence shown in SEQ ID NO: 5. Said first and/or second extracellular loops preferably form the extracellular portion of CLDN6.

The term "CLDN9" preferably relates to human CLDN9, and, in particular, to a protein comprising the amino acid sequence according to SEQ ID NO: 7 of the sequence listing or a variant of said amino acid sequence. The first extracellular loop of CLDN9 preferably comprises amino acids 28 to 76 of the amino acid sequence shown in SEQ ID NO: 7. The second extracellular loop of CLDN9 preferably comprises amino acids 141 to 159 of the amino acid sequence shown in SEQ ID NO: 7. Said first and/or second extracellular loops preferably form the extracellular portion of CLDN9.

The term "CLDN4" preferably relates to human CLDN4, and, in particular, to a protein comprising the amino acid sequence according to SEQ ID NO: 8 of the sequence listing or a variant of said amino acid sequence. The first extracellular loop of CLDN4 preferably comprises amino acids 28 to 76 of the amino acid sequence shown in SEQ ID NO: 8. The second extracellular loop of CLDN4 preferably comprises amino acids 141 to 159 of the amino acid sequence shown in SEQ ID NO: 8. Said first and/or second extracellular loops preferably form the extracellular portion of CLDN4.

The term "CLDN3" preferably relates to human CLDN3, and, in particular, to a protein comprising the amino acid sequence according to SEQ ID NO: 9 of the sequence listing or a variant of said amino acid sequence. The first extracellular loop of CLDN3 preferably comprises amino acids 27 to 75 of the amino acid sequence shown in SEQ ID NO: 9. The second extracellular loop of CLDN3 preferably comprises amino acids 140 to 158 of the amino acid sequence shown in SEQ ID NO: 9. Said first and/or second extracellular loops preferably form the extracellular portion of CLDN3.

The above described CLDN sequences include any variants of said sequences, in particular mutants, splice variants, conformations, isoforms, allelic variants, species variants and species homologs, in particular those which are naturally present. An allelic variant relates to an alteration in the normal sequence of a gene, the significance of which is often unclear. Complete gene sequencing often identifies numerous allelic variants for a given gene. A species homolog is a nucleic acid or amino acid sequence with a different species of origin from that of a given nucleic acid or amino acid sequence. The term "CLDN" shall encompass (i) CLDN splice variants, (ii) CLDN-posttranslationally modified variants, particularly including variants with different glycosylation such as N-glycosylation status, (iii) CLDN conformation variants, (iv) CLDN cancer related and CLDN non-cancer related variants. Preferably, a CLDN is present in its native conformation.

The term "portion" refers to a fraction. With respect to a particular structure such as an amino acid sequence or protein the term "portion" thereof may designate a continuous or a discontinuous fraction of said structure. Preferably, a portion of an amino acid sequence comprises at least 1%, at least 5%, at least 10%, at least 20%, at least 30%, preferably at least 40%, preferably at least 50%, more preferably at least 60%, more preferably at least 70%, even more preferably at least 80%, and most preferably at least 90% of the amino acids of said amino acid sequence. Preferably, if the portion is a discontinuous fraction said discontinuous fraction is composed of 2, 3, 4, 5, 6, 7, 8, or more parts of a structure, each part being a continuous element of the structure. For example, a discontinuous fraction of an amino acid sequence may be composed of 2, 3, 4, 5, 6, 7, 8, or more, preferably not more than 4 parts of said amino acid sequence, wherein each part preferably comprises at least 5 continuous amino acids, at least 10 continuous amino acids, preferably at least 20 continuous amino acids, preferably at least 30 continuous amino acids of the amino acid sequence.

The terms "part" and "fragment" are used interchangeably herein and refer to a continuous element. For example, a part of a structure such as an amino acid sequence or protein refers to a continuous element of said structure. A portion, a part or a fragment of a structure preferably comprises one or more functional properties of said structure. For example, a portion, a part or a fragment of an epitope or peptide is preferably immunologically equivalent to the epitope or peptide it is derived from.

The term "an extracellular portion of a CLDN" in the context of the present invention refers to a part of a CLDN facing the extracellular space of a cell and preferably being accessible from the outside of said cell, e.g., by antibodies located outside the cell. Preferably, the term refers to one or more extracellular loops or a part thereof or any other extracellular part of a CLDN which is preferably specific for said CLDN. Preferably, said part comprises at least 5, at least 8, at least 10, at least 15, at least 20, at least 30, or at least 50 amino acids or more.

According to the invention, a CLDN expressed by a cell is preferably associated with the surface of said cell. The term "CLDN associated with the surface of a cell" means that the CLDN is associated with and located at the plasma membrane of said cell, wherein at least a part of the CLDN, preferably the extracellular portion, faces the extracellular space of said cell and is accessible from the outside of said cell, e.g., by antibodies located outside the cell. The association may be direct or indirect. For example, the association may be by one or more transmembrane domains, one or more lipid anchors, and/or by the interaction with any other protein, lipid, saccharide, or other structure that can be found on the outer leaflet of the plasma membrane of a cell. For example, a CLDN associated with the surface of a cell may be a transmembrane protein, i.e. an integral membrane protein, having an extracellular portion or may be a protein associated with the surface of a cell by interacting with another protein that is a transmembrane protein.

CLDN6 is associated with the surface of a cell if it is located at the surface of said cell and is accessible to binding by CLDN6-specific antibodies added to the cell. It is to be understood that in the case where CLDN6 is expressed by cells, the CLDN6 associated with the surface of said cells may only be a portion of the expressed CLDN6.

The term "a cell carrying a CLDN" preferably means that said cell carries a CLDN on its surface, i.e., that the CLDN is associated with the surface of said cell.

"Cell surface" or "surface of a cell" is used in accordance with its normal meaning in the art, and thus includes the outside of the cell which is accessible to binding by proteins and other molecules.

The expression "CLDN expressed on the surface of a cell" means that the CLDN expressed by a cell is found in association with the surface of said cell.

According to the invention CLDN6 is not substantially expressed in a cell and is not substantially associated with a cell surface if the level of expression and association is lower compared to expression and association in placenta cells or placenta tissue. Preferably, the level of expression and association is less than 10%, preferably less than 5%, 3%, 2%, 1%, 0.5%, 0.1% or 0.05% of the expression and association in placenta cells or placenta tissue or even lower. Preferably, CLDN6 is not substantially expressed in a cell and is not substantially associated with a cell surface if the level of expression and association exceeds the level of expression and association in non-tumorigenic, non-cancerous tissue other than placenta tissue by no more than 2-fold, preferably 1,5-fold, and preferably does not exceed the level of expression and association in said non-tumorigenic, non-cancerous tissue. Preferably, CLDN6 is not substantially expressed in a cell and is not substantially associated with a cell surface if the level of expression or association is below the detection limit and/or if the level of expression or association is too low to allow binding by CLDN6-specific antibodies added to the cells.

According to the invention CLDN6 is expressed in a cell and is associated with a cell surface if the level of expression and association exceeds the level of expression and association in non-tumorigenic, non-cancerous tissue other than placenta tissue, preferably by more than 2-fold, preferably 10-fold, 100-fold, 1000-fold, or 10000-fold. Preferably, CLDN6 is expressed in a cell and is associated with a cell surface if the level of expression and association is above the detection limit and/or if the level of expression and association is high enough to allow binding by CLDN6-specific antibodies added to the cells. Preferably, CLDN6 expressed in a cell is expressed or exposed on the surface of said cell.

The term "raft" refers to the sphingolipid- and cholesterol-rich membrane microdomains located in the outer leaflet area of the plasma membrane of a cell. The ability of certain proteins to associate within such domains and their ability of forming "aggregates" or "focal aggregates" can effect the protein's function. For example, the translocation of CLDN6 molecules into such structures, after being bound by antibodies of the present invention, creates a high density of CLDN6 antigen-antibody complexes in the plasma membranes. Such a high density of CLDN6 antigen-antibody complexes can enable efficient activation of the complement system during CDC.

The term "antibody" refers to a glycoprotein comprising at least two heavy (H) chains and two light (L) chains inter-connected by disulfide bonds, and includes any molecule comprising an antigen binding portion thereof. The term "antibody" includes monoclonal antibodies and fragments or derivatives thereof, including, without limitation, human monoclonal antibodies, humanized monoclonal antibodies, chimeric monoclonal antibodies, single chain antibodies, e.g., scFv's and antigen-binding antibody fragments such as Fab and Fab' fragments and also includes all recombinant forms of antibodies, e.g., antibodies expressed in prokaryotes, unglycosylated antibodies, and any antigen-binding antibody fragments and derivatives as described herein. Each heavy chain is comprised of a heavy chain variable region (abbreviated herein as VH) and a heavy chain constant region. Each light chain is comprised of a light chain variable region (abbreviated herein as VL) and a light chain constant region. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "humanized antibody" refers to a molecule having an antigen binding site that is substantially derived from an immunoglobulin from a non-human species, wherein the remaining immunoglobulin structure of the molecule is based upon the structure and/or sequence of a human immunoglobulin. The antigen binding site may either comprise complete variable domains fused onto constant domains or only the complementarity determining regions (CDR) grafted onto appropriate framework regions in the variable domains. Antigen binding sites may be wild-type or modified by one or more amino acid substitutions, e.g. modified to resemble human immunoglobulins more closely. Some forms of humanized antibodies preserve all CDR sequences (for example a humanized mouse antibody which contains all six CDRs from the mouse antibody). Other forms have one or more CDRs which are altered with respect to the original antibody.

The term "chimeric antibody" refers to those antibodies wherein one portion of each of the amino acid sequences of heavy and light chains is homologous to corresponding sequences in antibodies derived from a particular species or belonging to a particular class, while the remaining segment of the chain is homologous to corresponding sequences in another. Typically, the variable region of both light and heavy chains mimics the variable regions of antibodies derived from one species of mammals, while the constant portions are homologous to sequences of antibodies derived from another. One clear advantage to such chimeric forms is that the variable region can conveniently be derived from presently known sources using readily available B-cells or hybridomas from non-human host organisms in combination with constant regions derived from, for example, human cell preparations. While the variable region has the advantage of ease of preparation and the specificity is not affected by the source, the constant region being human, is less likely to elicit an immune response from a human subject when the antibodies are injected than would the constant region from a non human source. However the definition is not limited to this particular example.

The term "antigen-binding portion" of an antibody (or simply "binding portion") refers to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) Fab fragments, monovalent fragments consisting of the VL, VH, CL and CH domains; (ii) F(ab')$_2$ fragments, bivalent fragments comprising two Fab fragments linked by a disulfide bridge at the hinge region; (iii) Fd fragments consisting of the VH and CH domains; (iv) Fv fragments consisting of the VL and VH domains of a single arm of an antibody, (v) dAb fragments (Ward et al., (1989) Nature 341: 544-546), which consist of a VH domain; (vi) isolated complementarity determining regions (CDR), and (vii) combinations of two or more isolated CDRs which may optionally be joined by a synthetic linker. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242: 423-426; and Huston et al. (1988) Proc. Natl. Acad. Sci. USA 85: 5879-5883). Such single chain antibodies are also intended to be encompassed within the term "antigen-binding portion" of an antibody. A further example is binding-domain immunoglobulin fusion proteins comprising (i) a binding domain polypeptide that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. The binding domain polypeptide can be a heavy chain variable region or a light chain variable region. The binding-domain immunoglobulin fusion proteins are further disclosed in US 2003/0118592 and US 2003/0133939. These antibody fragments are obtained using conventional techniques known to those with skill in the art, and the fragments are screened for utility in the same manner as are intact antibodies.

The antibodies described herein are useful for passive anti-tumor immunotherapy, and may or may not be attached to therapeutic effector moieties, e.g., radiolabels, chemotherapeutics such as cisplatin, methotrexate, adriamycin, and the like suitable for cancer therapy, cytotoxins, therapeutic enzymes, agents that induce apoptosis, and the like in order to provide for targeted cytotoxicity, i.e., killing of tumor cells.

Preferably the antibodies described herein mediate killing of cells by inducing complement dependent cytotoxicity (CDC) mediated lysis, antibody dependent cellular cytotoxicity (ADCC) mediated lysis, apoptosis, homotypic adhesion, and/or phagocytosis, preferably by inducing CDC mediated lysis and/or ADCC mediated lysis. The antibodies described herein preferably interact with components of the immune system, preferably through ADCC or CDC. However, antibodies of the invention may also exert an effect simply by binding to tumor antigens on the cell surface, thus, e.g. blocking proliferation of the cells.

ADCC describes the cell-killing ability of effector cells as described herein, in particular lymphocytes, which preferably requires the target cell being marked by an antibody.

ADCC preferably occurs when antibodies bind to antigens on tumor cells and the antibody Fc domains engage Fc receptors (FcR) on the surface of immune effector cells. Several families of Fc receptors have been identified, and specific cell populations characteristically express defined Fc receptors. ADCC can be viewed as a mechanism to directly induce a variable degree of immediate tumor destruction that also leads to antigen presentation and the induction of tumor-directed T-cell responses. Preferably, in vivo induction of ADCC will lead to tumor-directed T-cell responses and host-derived antibody responses.

CDC is another cell-killing method that can be directed by antibodies. IgM is the most effective isotype for complement activation. IgG1 and IgG3 are also both very effective at directing CDC via the classical complement-activation pathway. Preferably, in this cascade, the formation of antigen-antibody complexes results in the uncloaking of multiple C1q binding sites in close proximity on the $C_H2$ domains of participating antibody molecules such as IgG molecules (C1q is one of three subcomponents of complement C1). Preferably these uncloaked C1q binding sites convert the previously low-affinity C1q-IgG interaction to one of high avidity, which triggers a cascade of events involving a series of other complement proteins and leads to the proteolytic release of the effector-cell chemotactic/activating agents C3a and C5a. Preferably, the complement cascade ends in the formation of a membrane attack complex, which creates pores in the cell membrane that facilitate free passage of water and solutes into and out of the cell and may lead to apoptosis.

The term "antibody" includes "bispecific molecules", i.e. molecules which have two different binding specificities. For example, the molecule may bind to, or interact with (a) a cell surface antigen, and (b) an Fc receptor on the surface of an effector cell. The term "antibody" also includes "multispecific molecules" or "heterospecific molecules", i.e. molecules which have more than two different binding specificities. For example, the molecule may bind to, or interact with (a) a cell surface antigen, (b) an Fc receptor on the surface of an effector cell, and (c) at least one other component. Accordingly, the invention includes, but is not limited to, bispecific, trispecific, tetraspecific, and other multispecific molecules which are directed to CLDN6, and to other targets, such as Fc receptors on effector cells. The term "antibody" also includes "bispecific antibodies" which also include diabodies. Diabodies are bivalent, bispecific antibodies in which the VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90: 6444-6448; Poljak, R. J., et al. (1994) Structure 2: 1121-1123).

The term "antibody" also includes "heteroantibodies" which term refers to two or more antibodies, derivatives thereof, or antigen binding regions linked together, at least two of which have different specificities. These different specificities include a binding specificity for an Fc receptor on an effector cell, and a binding specificity for an antigen or epitope on a target cell, e.g., a tumor cell.

"Target cell" shall mean any undesirable cell in a subject (e.g., a human or animal) that can be targeted by an antibody of the invention. In preferred embodiments, the target cell is a cell expressing CLDN6. Cells expressing CLDN6 typically include tumor cells.

As used herein, the term "effector cell" refers to an immune cell which is involved in the effector phase of an immune response, as opposed to the cognitive and activation phases of an immune response. Exemplary immune cells include cells of myeloid or lymphoid origin, e.g, lymphocytes (e.g., B cells and T cells including cytolytic T cells (cytotoxic T lymphocytes; CTLs), killer cells, natural killer cells, macrophages, monocytes, eosinophils, neutrophils, polymorphonuclear cells, granulocytes, mast cells, and basophils. Some effector cells express specific Fc receptors and carry out specific immune functions. In preferred embodiments, an effector cell is capable of inducing antibody-dependent cellular cytotoxicity (ADCC), e.g., a neutrophil capable of inducing ADCC. For example, monocytes, macrophages, which express FcR are involved in specific killing of target cells and presenting antigens to other components of the immune system, or binding to cells that present antigens. In other embodiments, an effector cell can phagocytose a target antigen, target cell, or microorganism. The expression of a particular FcR on an effector cell can be regulated by humoral factors such as cytokines. For example, expression of Fc-gammaRI has been found to be up-regulated by interferon gamma (IFN-γ). This enhanced expression increases the cytotoxic activity of Fc-gammaRI-bearing cells against targets. An effector cell can phagocytose or lyse a target antigen or a target cell.

The antibodies described herein may be human antibodies. The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo).

The antibodies described herein may be monoclonal antibodies. The term "monoclonal antibody" as used herein refers to a preparation of antibody molecules of single molecular composition. A monoclonal antibody displays a single binding specificity and affinity for a particular epitope. In one embodiment, the monoclonal antibodies are produced by a hybridoma which includes a B cell obtained from a non-human animal, e.g., mouse, fused to an immortalized cell.

The antibodies described herein may be recombinant antibodies. The term "recombinant antibody", as used herein, includes all antibodies that are prepared, expressed, created or isolated by recombinant means, such as (a) antibodies isolated from an animal (e.g., a mouse) that is transgenic or transchromosomal with respect to the immunoglobulin genes or a hybridoma prepared therefrom, (b) antibodies isolated from a host cell transformed to express the antibody, e.g., from a transfectoma, (c) antibodies isolated from a recombinant, combinatorial antibody library, and (d) antibodies prepared, expressed, created or isolated by any other means that involve splicing of immunoglobulin gene sequences to other DNA sequences.

The term "transfectoma", as used herein, includes recombinant eukaryotic host cells expressing an antibody, such as CHO cells, NS/0 cells, HEK293 cells, HEK293T cells, plant cells, or fungi, including yeast cells.

As used herein, a "heterologous antibody" is defined in relation to a transgenic organism producing such an antibody. This term refers to an antibody having an amino acid sequence or an encoding nucleic acid sequence corresponding to that found in an organism not consisting of the transgenic organism, and being generally derived from a species other than the transgenic organism.

As used herein, a "heterohybrid antibody" refers to an antibody having light and heavy chains of different organismal origins. For example, an antibody having a human heavy chain associated with a murine light chain is a heterohybrid antibody.

The invention includes all antibodies and derivatives of antibodies as described herein which for the purposes of the invention are encompassed by the term "antibody". The term "antibody derivatives" refers to any modified form of an antibody, e.g., a conjugate of the antibody and another agent or antibody, or an antibody fragment.

The antibodies described herein are preferably isolated. An "isolated antibody" as used herein, is intended to refer to an antibody which is substantially free of other antibodies having different antigenic specificities (e.g., an isolated antibody that specifically binds to CLDN6 is substantially free of antibodies that specifically bind antigens other than CLDN6). An isolated antibody that specifically binds to an epitope, isoform or variant of human CLDN6 may, however, have cross-reactivity to other related antigens, e.g., from other species (e.g., CLDN6 species homologs). Moreover, an isolated antibody may be substantially free of other cellular material and/or chemicals. In one embodiment of the invention, a combination of "isolated" monoclonal antibodies relates to antibodies having different specificities and being combined in a well defined composition.

According to the present invention, an antibody is capable of binding to a predetermined target if it has a significant affinity for said predetermined target and binds to said predetermined target in standard assays. "Affinity" or "binding affinity" is often measured by equilibrium dissociation constant ($K_D$). Preferably, the term "significant affinity" refers to the binding to a predetermined target with a dissociation constant ($K_D$) of $10^{-5}$ M or lower, $10^{-6}$ M or lower, $10^{-7}$ M or lower, $10^{-8}$ M or lower, $10^{-9}$ M or lower, $10^{-10}$ M or lower, $10^{-11}$ M or lower, or $10^{-12}$ M or lower.

An antibody is not (substantially) capable of binding to a target if it has no significant affinity for said target and does not bind significantly to said target in standard assays. Preferably, an antibody is not (substantially) capable of binding to a target if it does not detectably bind to said target in a flow cytometry analysis (FACS analysis) wherein binding of said antibody to said target expressed on the surface of intact cells is determined. Preferably, the antibody does not detectably bind to said target if present in a concentration of up to 2, preferably 10, more preferably 20, in particular 50 or 100 μg/ml or higher. Preferably, an antibody has no significant affinity for a target if it binds to said target with a $K_D$ that is at least 10-fold, 100-fold, $10^3$-fold, $10^4$-fold, $10^5$-fold, or $10^6$-fold higher than the $K_D$ for binding to the predetermined target to which the antibody is capable of binding. For example, if the $K_D$ for binding of an antibody to the target to which the antibody is capable of binding is $10^{-7}$ M, the $K_D$ for binding to a target for which the antibody has no significant affinity would be is at least $10^{-6}$ M, $10^{-5}$ M, $10^{-4}$ M, $10^{-3}$ M, $10^{-2}$ M, or $10^{-1}$M.

An antibody according to the present invention is preferably capable of binding specifically to a predetermined target, in particular CLDN6.

An antibody is specific for a predetermined target if it is capable of binding to said predetermined target while it is not capable of binding to other targets, i.e. has no significant affinity for other targets and does not significantly bind to other targets in standard assays. According to the invention, an antibody is specific for CLDN6 if it is capable of binding to CLDN6 but is not (substantially) capable of binding to other targets, in particular claudin proteins other than CLDN6 such as CLDN9, CLDN4, CLDN3 and CLDN1. Preferably, an antibody is specific for CLDN6 if the affinity for and the binding to a claudin protein other than CLDN6 such as CLDN9, CLDN4, CLDN3 and CLDN1 does not significantly exceed the affinity for or binding to claudin-unrelated proteins such as bovine serum albumin (BSA), casein, human serum albumin (HSA) or non-claudin transmembrane proteins such as MHC molecules or transferrin receptor or any other specified polypeptide. Preferably, an antibody is specific for a predetermined target if it binds to said target with a $K_D$ that is at least 10-fold, 100-fold, $10^3$-fold, $10^4$-fold, $10^5$-fold, or $10^6$-fold lower than the $K_D$ for binding to a target for which it is not specific. For example, if the $K_D$ for binding of an antibody to the target for which it is specific is $10^{-7}$ M, the $K_D$ for binding to a target for which it is not specific would be at least $10^{-6}$ M, $10^{-5}$ M, $10^{-4}$ M, $10^{-3}$ M, $10^{-2}$ M, or $10^{-1}$M.

Binding of an antibody to a target can be determined experimentally using any suitable method; see, for example, Berzofsky et al., "Antibody-Antigen Interactions" In Fundamental Immunology, Paul, W. E., Ed., Raven Press New York, N Y (1984), Kuby, Janis Immunology, W. H. Freeman and Company New York, N Y (1992), and methods described herein. Affinities may be readily determined using conventional techniques, such as by equilibrium dialysis; by using the BIAcore 2000 instrument, using general procedures outlined by the manufacturer; by radioimmunoassay using radiolabeled target antigen; or by another method known to the skilled artisan. The affinity data may be analyzed, for example, by the method of Scatchard et al., Ann N.Y. Acad. ScL, 51:660 (1949). The measured affinity of a particular antibody-antigen interaction can vary if measured under different conditions, e.g., salt concentration, pH. Thus, measurements of affinity and other antigen-binding parameters, e.g., $K_D$, $IC_{50}$, are preferably made with standardized solutions of antibody and antigen, and a standardized buffer.

As used herein, "isotype" refers to the antibody class (e.g., IgM or IgG1) that is encoded by heavy chain constant region genes. Antibodies according to the invention include polyclonal and monoclonal antibodies and include IgG2a (e.g. IgG2a, κ, λ), IgG2b (e.g. IgG2b, κ, λ), IgG3 (e.g. IgG3, κ, λ) and IgM antibodies. However, other antibody isotypes are also encompassed by the invention, including IgG1, IgA1, IgA2, secretory IgA, IgD, and IgE antibodies.

As used herein, "isotype switching" refers to the phenomenon by which the class, or isotype, of an antibody changes from one Ig class to one of the other Ig classes.

The term "naturally occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally occurring.

The term "rearranged" as used herein refers to a configuration of a heavy chain or light chain immunoglobulin locus wherein a V segment is positioned immediately adjacent to a D-J or J segment in a conformation encoding essentially a complete VH or VL domain, respectively. A rearranged immunoglobulin (antibody) gene locus can be identified by comparison to germline DNA; a rearranged locus will have at least one recombined heptamer/nonamer homology element.

The term "unrearranged" or "germline configuration" as used herein in reference to a V segment refers to the configuration wherein the V segment is not recombined so as to be immediately adjacent to a D or J segment.

According to the invention, antibodies may be derived from different species, including but not limited to mouse, rat, rabbit, guinea pig and human. Antibodies also include chimeric molecules in which an antibody constant region derived from one species, preferably human, is combined with the antigen binding site derived from another species. Moreover, antibodies include humanized molecules in which the antigen binding sites of an antibody derived from a non-human species are combined with constant and framework regions of human origin.

Antibodies can be produced by a variety of techniques, including conventional monoclonal antibody methodology, e.g., the standard somatic cell hybridization technique of Kohler and Milstein, Nature 256: 495 (1975). Although somatic cell hybridization procedures are preferred, in principle, other techniques for producing monoclonal antibodies can be employed, e.g., viral or oncogenic transformation of B-lymphocytes or phage display techniques using libraries of antibody genes.

The preferred animal system for preparing hybridomas that secrete monoclonal antibodies is the murine system. Hybridoma production in the mouse is a very well established procedure. Immunization protocols and techniques for isolation of immunized splenocytes for fusion are known in the art. Fusion partners (e.g., murine myeloma cells) and fusion procedures are also known.

Other preferred animal systems for preparing hybridomas that secrete monoclonal antibodies are the rat and the rabbit system (e.g. described in Spieker-Polet et al., Proc. Natl. Acad. Sci. U.S.A. 92:9348 (1995), see also Rossi et al., Am. J. Clin. Pathol. 124: 295 (2005)).

In yet another preferred embodiment, human monoclonal antibodies directed against CLDN6 can be generated using transgenic or transchromosomal mice carrying parts of the human immune system rather than the mouse system. These transgenic and transchromosomic mice include mice known as HuMAb mice and KM mice, respectively, and are collectively referred to herein as "transgenic mice." The production of human antibodies in such transgenic mice can be performed as described in detail for CD20 in WO2004 035607

Yet another strategy for generating monoclonal antibodies is to directly isolate genes encoding antibodies from lymphocytes producing antibodies of defined strategy e.g. see Babcock et al., 1996; A novel strategy for generating monoclonal antibodies from single, isolated lymphocytes producing antibodies of defined strategy. For details of recombinant antibody engineering see also Welschof and Kraus, Recombinant antibodes for cancer therapy ISBN-0-89603-918-8 and Benny K. C. Lo Antibody Engineering ISBN 1-58829-092-1.

To generate antibodies to CLDN6, mice can be immunized with carrier-conjugated peptides derived from the CLDN6 sequence, an enriched preparation of recombinantly expressed CLDN6 antigen or fragments thereof and/or cells expressing CLDN6 or fragments thereof, as described. Alternatively, mice can be immunized with DNA encoding full length human CLDN6 or fragments thereof. In the event that immunizations using a purified or enriched preparation of the CLDN6 antigen do not result in antibodies, mice can also be immunized with cells expressing CLDN6, e.g., a cell line, to promote immune responses.

The immune response can be monitored over the course of the immunization protocol with plasma and serum samples being obtained by tail vein or retroorbital bleeds. Mice with sufficient titers of anti-CLDN6 immunoglobulin can be used for fusions. Mice can be boosted intraperitonealy or intravenously with CLDN6 expressing cells 3-5 days before sacrifice and removal of the spleen to increase the rate of specific antibody secreting hybridomas.

To generate hybridomas producing monoclonal antibodies to CLDN6, cells from lymph nodes, spleens or bone marrow obtained from immunized mice can be isolated and fused to an appropriate immortalized cell line, such as a mouse myeloma cell line. The resulting hybridomas can then be screened for the production of antigen-specific antibodies. Individual wells can then be screened by ELISA for antibody secreting hybridomas. By Immunofluorescence and FACS analysis using CLDN6 expressing cells, antibodies with specificity for CLDN6 can be identified. The antibody secreting hybridomas can be replated, screened again, and if still positive for anti-CLDN6 monoclonal antibodies can be subcloned by limiting dilution. The stable subclones can then be cultured in vitro to generate antibody in tissue culture medium for characterization.

Antibodies of the invention can also be produced in a host cell transfectoma using, for example, a combination of recombinant DNA techniques and gene transfection methods as are well known in the art (Morrison, S. (1985) Science 229: 1202).

For example, in one embodiment, the gene(s) of interest, e.g., antibody genes, can be ligated into an expression vector such as a eukaryotic expression plasmid such as used by the GS gene expression system disclosed in WO 87/04462, WO 89/01036 and EP 338 841 or other expression systems well known in the art. The purified plasmid with the cloned antibody genes can be introduced in eukaryotic host cells such as CHO cells, NS/0 cells, HEK293T cells or HEK293 cells or alternatively other eukaryotic cells like plant derived cells, fungal or yeast cells. The method used to introduce these genes can be methods described in the art such as electroporation, lipofectine, lipofectamine or others. After introduction of these antibody genes in the host cells, cells expressing the antibody can be identified and selected. These cells represent the transfectomas which can then be amplified for their expression level and upscaled to produce antibodies. Recombinant antibodies can be isolated and purified from these culture supernatants and/or cells.

Alternatively, the cloned antibody genes can be expressed in other expression systems, including prokaryotic cells, such as microorganisms, e.g. *E. coli*. Furthermore, the antibodies can be produced in transgenic non-human animals, such as in milk from sheep and rabbits or in eggs from hens, or in transgenic plants; see e.g. Verma, R., et al. (1998) J. Immunol. Meth. 216: 165-181; Pollock, et al. (1999) J. Immunol. Meth. 231: 147-157; and Fischer, R., et al. (1999) Biol. Chem. 380: 825-839.

Murine monoclonal antibodies can be used as therapeutic antibodies in humans when labeled with toxins or radioactive isotopes. Nonlabeled murine antibodies are highly immunogenic in man when repetitively applied leading to reduction of the therapeutic effect. The main immunogenicity is mediated by the heavy chain constant regions. The immunogenicity of murine antibodies in man can be reduced or completely avoided if respective antibodies are chimerized or humanized. Chimeric antibodies are antibodies, the different portions of which are derived from different animal species, such as those having a variable region derived from a murine antibody and a human immunoglobulin constant region. Chimerisation of antibodies is achieved by joining of the variable regions of the murine antibody heavy and light chain with the constant region of human heavy and light chain (e.g. as described by Kraus et al., in Methods in Molecular Biology series, Recombinant antibodies for cancer therapy ISBN-0-89603-918-8). In a preferred embodiment, chimeric antibodies are generated by joining human kappa-light chain constant region to murine light chain variable region. In an also preferred embodiment, chimeric antibodies can be generated by joining human lambda-light chain constant region to murine light chain variable region. The preferred heavy chain constant regions for generation of chimeric antibodies are IgG1, IgG3 and IgG4. Other preferred heavy chain constant regions for generation of chimeric antibodies are IgG2, IgA, IgD and IgM.

Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) Nature 332: 323-327; Jones, P. et al. (1986) Nature 321: 522-525; and Queen, C. et al. (1989) Proc. Natl. Acad. Sci. U.S.A 86: 10029-10033). Such framework sequences can be obtained from public DNA databases that include germline antibody gene sequences. These germline sequences will differ from mature antibody gene sequences because they will not include completely assembled variable genes, which are formed by V (D) J joining during B cell maturation. Germline gene sequences will also differ from the sequences of a high affinity secondary repertoire antibody at individual positions evenly across the variable region. For example, somatic mutations are relatively infrequent in the amino terminal portion of framework region 1 and in the carboxy-terminal portion of framework region 4. Furthermore, many somatic mutations do not significantly alter the binding properties of the antibody. For this reason, it is not necessary to obtain the entire DNA sequence of a particular antibody in order to recreate an intact recombinant antibody having binding properties similar to those of the original antibody (see WO 99/45962). Partial heavy and light chain sequences spanning the CDR regions are typically sufficient for this purpose. The partial sequence is used to determine which germline variable and joining gene segments contributed to the recombined antibody variable genes. The germline sequence is then used to fill in missing portions of the variable regions. Heavy and light chain leader sequences are cleaved during protein maturation and do not contribute to the properties of the final antibody. To add missing sequences, cloned cDNA sequences can be combined with synthetic oligonucleotides by ligation or PCR amplification. Alternatively, the entire variable region can be synthesized as a set of short, overlapping, oligonucleotides and combined by PCR amplification to create an entirely synthetic variable region clone. This process has certain advantages such as elimination or inclusion or particular restriction sites, or optimization of particular codons.

The nucleotide sequences of heavy and light chain transcripts from hybridomas are used to design an overlapping set of synthetic oligonucleotides to create synthetic V sequences with identical amino acid coding capacities as the natural sequences. The synthetic heavy and kappa chain sequences can differ from the natural sequences in three ways: strings of repeated nucleotide bases are interrupted to facilitate oligonucleotide synthesis and PCR amplification; optimal translation initiation sites are incorporated according to Kozak's rules (Kozak, 1991, J. Biol. Chem. 266: 19867-19870); and HindIII sites are engineered upstream of the translation initiation sites.

For both the heavy and light chain variable regions, the optimized coding and corresponding non-coding, strand sequences are broken down into 30-50 nucleotides approximately at the midpoint of the corresponding non-coding oligonucleotide. Thus, for each chain, the oligonucleotides can be assembled into overlapping double stranded sets that span segments of 150-400 nucleotides. The pools are then used as templates to produce PCR amplification products of 150-400 nucleotides. Typically, a single variable region oligonucleotide set will be broken down into two pools which are separately amplified to generate two overlapping PCR products. These overlapping products are then combined by PCR amplification to form the complete variable region. It may also be desirable to include an overlapping fragment of the heavy or light chain constant region in the PCR amplification to generate fragments that can easily be cloned into the expression vector constructs.

The reconstructed chimerized or humanized heavy and light chain variable regions are then combined with cloned promoter, leader, translation initiation, constant region, 3' untranslated, polyadenylation, and transcription termination sequences to form expression vector constructs. The heavy and light chain expression constructs can be combined into a single vector, co-transfected, serially transfected, or separately transfected into host cells which are then fused to form a host cell expressing both chains. Plasmids for use in construction of expression vectors for human IgGκ are described. The plasmids can be constructed so that PCR amplified V heavy and V kappa light chain cDNA sequences can be used to reconstruct complete heavy and light chain minigenes. These plasmids can be used to express completely human, or chimeric IgG1, Kappa or IgG4, Kappa antibodies. Similar plasmids can be constructed for expression of other heavy chain isotypes, or for expression of antibodies comprising lambda light chains.

Thus, in another aspect of the invention, the structural features of the anti-CLDN6 antibodies described herein, are used to create structurally related humanized anti-CLDN6 antibodies that retain at least one functional property of the antibodies of the invention, such as binding to CLDN6. More specifically, one or more CDR regions of mouse monoclonal antibodies can be combined recombinantly with known human framework regions and CDRs to create additional, recombinantly-engineered, humanized anti-CLDN6 antibodies.

The ability of an antibody to bind CLDN6 can be determined using standard binding assays, such as those set forth in the examples (e.g., ELISA, Western Blot, Immunofluorescence and flow cytometric analysis)

The term "epitope" refers to an antigenic determinant in a molecule, i.e., to the part in a molecule that is recognized by the immune system, for example, that is recognized by an antibody. For example, epitopes are the discrete, three-dimensional sites on an antigen, which are recognized by the immune system. In the context of the present invention, the epitope is preferably derived from a CLDN protein. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents. An epitope of a protein such as a CLDN preferably comprises a continuous or discontinuous portion of said protein and is preferably between 5 and 100, preferably between 5 and 50, more preferably between 8 and 30, most preferably between 10 and 25 amino acids in length, for example, the epitope may be preferably 8, 9, 10, 11, 12, 13, 14, 15, 16, 17, 18, 19, 20, 21, 22, 23, 24, or 25 amino acids in length.

The term "discontinuous epitope" as used herein, means a conformational epitope on a protein antigen which is formed from at least two separate regions in the primary sequence of the protein.

According to the invention, the term "binding" preferably relates to a specific binding. "Specific binding" means that an agent such as an antibody binds stronger to a target such as an epitope for which it is specific compared to the binding to another target. An agent binds stronger to a first target compared to a second target if it binds to the first target with a dissociation constant ($K_D$) which is lower than the dissociation constant for the second target. Preferably the dissociation constant ($K_D$) for the target to which the agent binds specifically is more than $10^2$-fold, $10^3$-fold, $10^4$-fold, $10^5$-fold, $10^6$-fold, $10^7$-fold, $10^8$-fold, $10^9$-fold, or $10^{10}$-fold lower than the dissociation constant ($K_D$) for the target to which the agent does not bind specifically.

The term "nucleic acid", as used herein, is intended to include deoxyribonucleic acid (DNA) and ribonucleic acid (RNA). Nucleic acids comprise according to the invention genomic DNA, cDNA, mRNA, recombinantly produced and chemically synthesized molecules. According to the invention, a nucleic acid may be present as a single-stranded or double-stranded and linear or covalently circularly closed molecule.

The nucleic acids described according to the invention have preferably been isolated. The term "isolated nucleic acid" means according to the invention that the nucleic acid was (i) amplified in vitro, for example by polymerase chain reaction (PCR), (ii) recombinantly produced by cloning, (iii) purified, for example by cleavage and gel-electrophoretic fractionation, or (iv) synthesized, for example by chemical synthesis. An isolated nucleic acid is a nucleic acid which is available for manipulation by recombinant DNA techniques.

Nucleic acids may, according to the invention, be present alone or in combination with other nucleic acids, which may be homologous or heterologous. In preferred embodiments, a nucleic acid is functionally linked to expression control sequences which may be homologous or heterologous with respect to said nucleic acid wherein the term "homologous" means that the nucleic acid is also functionally linked to the expression control sequence naturally and the term "heterologous" means that the nucleic acid is not functionally linked to the expression control sequence naturally.

A nucleic acid, such as a nucleic acid expressing RNA and/or protein or peptide, and an expression control sequence are "functionally" linked to one another, if they are covalently linked to one another in such a way that expression or transcription of said nucleic acid is under the control or under the influence of said expression control sequence. If the nucleic acid is to be translated into a functional protein, then, with an expression control sequence functionally linked to a coding sequence, induction of said expression control sequence results in transcription of said nucleic acid, without causing a frame shift in the coding sequence or said coding sequence not being capable of being translated into the desired protein or peptide.

The term "expression control sequence" or "expression control element" comprises according to the invention promoters, ribosome binding sites, enhancers and other control elements which regulate transcription of a gene or translation of a mRNA. In particular embodiments of the invention, the expression control sequences can be regulated. The exact structure of expression control sequences may vary as a function of the species or cell type, but generally comprises 5'-untranscribed and 5'- and 3'-untranslated sequences which are involved in initiation of transcription and translation, respectively, such as TATA box, capping sequence, CAAT sequence, and the like. More specifically, 5'-untranscribed expression control sequences comprise a promoter region which includes a promoter sequence for transcriptional control of the functionally linked nucleic acid. Expression control sequences may also comprise enhancer sequences or upstream activator sequences.

According to the invention the term "promoter" or "promoter region" relates to a nucleic acid sequence which is located upstream (5') to the nucleic acid sequence being expressed and controls expression of the sequence by providing a recognition and binding site for RNA-polymerase. The "promoter region" may include further recognition and binding sites for further factors which are involved in the regulation of transcription of a gene. A promoter may control the transcription of a prokaryotic or eukaryotic gene. Furthermore, a promoter may be "inducible" and may initiate transcription in response to an inducing agent or may be "constitutive" if transcription is not controlled by an inducing agent. A gene which is under the control of an inducible promoter is not expressed or only expressed to a small extent if an inducing agent is absent. In the presence of the inducing agent the gene is switched on or the level of transcription is increased. This is mediated, in general, by binding of a specific transcription factor.

Promoters which are preferred according to the invention include promoters for SP6, T3 and T7 polymerase, human U6 RNA promoter, CMV promoter, and artificial hybrid promoters thereof (e.g. CMV) where a part or parts are fused to a part or parts of promoters of genes of other cellular proteins such as e.g. human GAPDH (glyceraldehyde-3-phosphate dehydrogenase), and including or not including (an) additional intron(s).

According to the invention, the term "expression" is used in its most general meaning and comprises the production of RNA or of RNA and protein/peptide. It also comprises partial expression of nucleic acids. Furthermore, expression may be carried out transiently or stably. According to the invention, the term expression also includes an "aberrant expression" or "abnormal expression".

"Aberrant expression" or "abnormal expression" means according to the invention that expression is altered, preferably increased, compared to a reference, preferably compared to the state in a non-tumorigenic normal cell or a healthy individual. An increase in expression refers to an increase by at least 10%, in particular at least 20%, at least 50%, at least 100%, at least 200%, at least 500%, at least 1000%, at least 10000% or even more. In one embodiment, expression is only found in a diseased tissue, while expression in a healthy tissue is repressed.

In a preferred embodiment, a nucleic acid molecule is according to the invention present in a vector, where appropriate with a promoter, which controls expression of the nucleic acid. The term "vector" is used here in its most general meaning and comprises any intermediary vehicle for a nucleic acid which enables said nucleic acid, for example, to be introduced into prokaryotic and/or eukaryotic cells and, where appropriate, to be integrated into a genome. Vectors of this kind are preferably replicated and/or expressed in the cells. Vectors comprise plasmids, phagemids, bacteriophages or viral genomes. The term "plasmid" as used herein generally relates to a construct of extrachromosomal genetic material, usually a circular DNA duplex, which can replicate independently of chromosomal DNA.

As the vector for expression of an antibody, either of a vector type in which the antibody heavy chain and light chain are present in different vectors or a vector type in which the heavy chain and light chain are present in the same vector can be used.

The teaching given herein with respect to specific nucleic acid and amino acid sequences, e.g. those shown in the sequence listing, is to be construed so as to also relate to modifications of said specific sequences resulting in sequences which are functionally equivalent to said specific sequences, e.g. amino acid sequences exhibiting properties identical or similar to those of the specific amino acid sequences and nucleic acid sequences encoding amino acid sequences exhibiting properties identical or similar to those of the amino acid sequences encoded by the specific nucleic acid sequences.

Similarly, the teaching given herein with respect to specific antibodies or hybridomas producing specific antibodies is to be construed so as to also relate to antibodies characterized by an amino acid sequence and/or nucleic acid sequence which is modified compared to the amino acid sequence and/or nucleic acid sequence of the specific antibodies but being functionally equivalent. One important property is to retain binding of an antibody to its target or to sustain effector functions of an antibody. Preferably, a sequence modified with respect to a specific sequence, when it replaces the specific sequence in an antibody retains binding of said antibody to the target and preferably functions of said antibody as described herein, e.g. CDC mediated lysis or ADCC mediated lysis.

It will be appreciated by those skilled in the art that in particular the sequences of the CDR, hypervariable and variable regions can be modified without losing the ability to bind to a target. For example, CDR regions will be either identical or highly homologous to the regions of antibodies specified herein. By "highly homologous" it is contemplated that from 1 to 5, preferably from 1 to 4, such as 1 to 3 or 1 or 2 substitutions may be made in the CDRs. In addition, the hypervariable and variable regions may be modified so that they show substantial homology with the regions of antibodies specifically disclosed herein.

It is to be understood that the specific nucleic acids described herein also include nucleic acids modified for the sake of optimizing the codon usage in a particular host cell or organism. Differences in codon usage among organisms can lead to a variety of problems concerning heterologous gene expression. Codon optimization by changing one or more nucleotides of the original sequence can result in an optimization of the expression of a nucleic acid, in particular in optimization of translation efficacy, in a homologous or heterologous host in which said nucleic acid is to be expressed. For example, if nucleic acids derived from human and encoding constant regions and/or framework regions of antibodies are to be used according to the present invention, e.g. for preparing chimeric or humanized antibodies, it may be preferred to modify said nucleic acids for the sake of optimization of codon usage, in particular if said nucleic acids, optionally fused to heterologous nucleic acids such as nucleic acids derived from other organisms as described herein, are to be expressed in cells from an organism different from human such as mouse or hamster. For example, the nucleic acid sequences encoding human light and heavy chain constant regions can be modified to include one or more, preferably, at least 1, 2, 3, 4, 5, 10, 15, 20 and preferably up to 10, 15, 20, 25, 30, 50, 70 or 100 or more nucleotide replacements resulting in an optimized codon usage. Such nucleotide replacements preferably relate to replacements of nucleotides not resulting in a change in the encoded amino acid sequence or relate to corresponding replacements at corresponding positions in other nucleic acid sequences encoding human light and heavy chain constant regions, respectively.

Preferably the degree of identity between a specific nucleic acid sequence and a nucleic acid sequence which is modified with respect to or which is a variant of said specific nucleic acid sequence will be at least 70%, preferably at least 75%, more preferably at least 80%, even more preferably at least 90% or most preferably at least 95%, 96%, 97%, 98% or 99%. Regarding CLDN6 nucleic acid variants, the degree of identity is preferably given for a region of at least about 300, at least about 400, at least about 450, at least about 500, at least about 550, at least about 600 or at least about 630 nucleotides. In preferred embodiments, the degree of identity is given for the entire length of the reference nucleic acid sequence, such as the nucleic acid sequences given in the sequence listing. Preferably, the two sequences are capable of hybridizing and forming a stable duplex with one another, with hybridization preferably being carried out under conditions which allow specific hybridization between polynucleotides (stringent conditions). Stringent conditions are described, for example, in Molecular Cloning: A Laboratory Manual, J. Sambrook et al., Editors, 2nd Edition, Cold Spring Harbor Laboratory press, Cold Spring Harbor, N.Y., 1989 or Current Protocols in Molecular Biology, F. M. Ausubel et al., Editors, John Wiley & Sons, Inc., New York and refer, for example, to hybridization at 65° C. in hybridization buffer (3.5×SSC, 0.02% Ficoll, 0.02% polyvinylpyrrolidone, 0.02% bovine serum albumin, 2.5 mM $NaH_2PO_4$ (pH 7), 0.5% SDS, 2 mM EDTA). SSC is 0.15 M sodium chloride/0.15 M sodium citrate, pH 7. After hybridization, the membrane to which the DNA has been transferred is washed, for example, in 2×SSC at room temperature and then in 0.1-0.5×SSC/0.1×SDS at temperatures of up to 68° C.

The term "variant" with respect to, for example, nucleic acid and amino acid sequences, according to the invention includes any variants, in particular mutants, splice variants, conformations, isoforms, allelic variants, species variants and species homologs, in particular those which are naturally present. An allelic variant relates to an alteration in the normal sequence of a gene, the significance of which is often unclear. Complete gene sequencing often identifies numerous allelic variants for a given gene. A species homolog is a nucleic acid or amino acid sequence with a different species of origin from that of a given nucleic acid or amino acid sequence.

With respect to nucleic acid molecules, the term "variant" includes degenerate nucleic acid sequences, wherein a degenerate nucleic acid according to the invention is a nucleic acid that differs from a reference nucleic acid in codon sequence due to the degeneracy of the genetic code.

Furthermore, a "variant" of a specific nucleic acid sequence according to the invention includes nucleic acid sequences comprising single or multiple such as at least 2, at least 4, or at least 6 and preferably up to 3, up to 4, up to 5, up to 6, up to 10, up to 15, or up to 20 nucleotide substitutions, deletions and/or additions.

For the purposes of the present invention, "variants" of an amino acid sequence comprise amino acid insertion variants, amino acid deletion variants and/or amino acid substitution variants.

In the case of amino acid sequence variants having an insertion, one or more amino acid residues are inserted into a particular site in an amino acid sequence, although random insertion with appropriate screening of the resulting product is also possible.

Amino acid deletion variants are characterized by the removal of one or more amino acids from the sequence.

Amino acid substitution variants are characterized by at least one residue in the sequence being removed and another residue being inserted in its place. Preference is given to the modifications being in positions in the amino acid sequence which are not conserved between homologous proteins or peptides and/or to replacing amino acids with other ones having similar properties.

Preferably, amino acid changes in protein variants are conservative amino acid changes, i.e., substitutions of similarly charged or uncharged amino acids.

Preferably the degree of similarity, preferably identity between a specific amino acid sequence and an amino acid sequence which is modified with respect to or which is a variant of said specific amino acid sequence such as between amino acid sequences showing substantial homology will be at least 70%, preferably at least 80%, even more preferably at least 90% or most preferably at least 95%, 96%, 97%, 98% or 99%. Regarding CLDN6 polypeptide variants, the degree of similarity or identity is given preferably for a region of at least about 100, at least about 120, at least about 140, at least about 160, at least about 180, at least about 200, at least about 210 amino acids. In preferred embodiments, the degree of similarity or identity is given for the entire length of the reference amino acid sequence such as the amino acid sequences given in the sequence listing.

"Sequence similarity" indicates the percentage of amino acids that either are identical or that represent conservative amino acid substitutions. "Sequence identity" between two polypeptide or nucleic acid sequences indicates the percentage of amino acids or nucleotides that are identical between the sequences.

The term "percentage identity" is intended to denote a percentage of nucleotides or of amino acid residues which are identical between the two sequences to be compared, obtained after the best alignment, this percentage being purely statistical and the differences between the two sequences being distributed randomly and over their entire length. Sequence comparisons between two nucleotide or amino acid sequences are conventionally carried out by comparing these sequences after having aligned them optimally, said comparison being carried out by segment or by "window of comparison" in order to identify and compare local regions of sequence similarity. The optimal alignment of the sequences for comparison may be produced, besides manually, by means of the local homology algorithm of Smith and Waterman, 1981, Ads App. Math. 2, 482, by means of the local homology algorithm of Neddleman and Wunsch, 1970, J. Mol. Biol. 48, 443, by means of the similarity search method of Pearson and Lipman, 1988, Proc. Natl Acad. Sci. USA 85, 2444, or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.).

The percentage identity is calculated by determining the number of identical positions between the two sequences being compared, dividing this number by the number of positions compared and multiplying the result obtained by 100 so as to obtain the percentage identity between these two sequences.

"Conservative substitutions," may be made, for instance, on the basis of similarity in polarity, charge, solubility, hydrophobicity, hydrophilicity, and/or the amphipathic nature of the residues involved. For example: (a) nonpolar (hydrophobic) amino acids include alanine, leucine, isoleucine, valine, proline, phenylalanine, tryptophan, and methionine; (b) polar neutral amino acids include glycine, serine, threonine, cysteine, tyrosine, asparagine, and glutamine; (c) positively charged (basic) amino acids include arginine, lysine, and histidine; and (d) negatively charged (acidic) amino acids include aspartic acid and glutamic acid. Substitutions typically may be made within groups (a)-(d). In addition, glycine and proline may be substituted for one another based on their ability to disrupt α-helices. Some preferred substitutions may be made among the following groups: (i) S and T; (ii) P and G; and (iii) A, V, L and I. Given the known genetic code, and recombinant and synthetic DNA techniques, the skilled scientist readily can construct DNAs encoding the conservative amino acid variants.

The invention includes derivatives of the nucleic acid sequences, amino acid sequences, peptides or proteins, in particular antibodies, described herein.

The term "derivative" comprises any chemical derivatization of a nucleic acid on a nucleotide base, on the sugar or on the phosphate. The term "derivative" also comprises nucleic acids which contain nucleotides and nucleotide analogs not occurring naturally. Preferably, a derivatization of a nucleic acid increases its stability.

According to the invention, "derivatives" of proteins and peptides are modified forms of proteins and peptides. Such modifications include any chemical modification and comprise single or multiple substitutions, deletions and/or additions of any molecules associated with the protein or peptide, such as carbohydrates, lipids and/or proteins or peptides. The term "derivative" also extends to all functional chemical equivalents of said proteins and peptides. Preferably, a modified peptide has increased stability and/or increased immunogenicity.

According to the invention, a variant, derivative, modified form, fragment, part or portion of a nucleic acid sequence, amino acid sequence, peptide or protein preferably has a functional property of the nucleic acid sequence, amino acid sequence, peptide or protein, respectively, from which it has been derived. Such functional properties comprise the interaction with peptides or proteins such as antibodies or antibody targets, in particular CLDN6, the selective binding of nucleic acids and an enzymatic activity. In one embodiment, a variant, derivative, modified form, fragment, part or portion of a nucleic acid sequence, amino acid sequence, peptide or protein is immunologically equivalent to the nucleic acid sequence, amino acid sequence, peptide or protein, respectively, from which it has been derived. In one embodiment, the functional property is an immunological property.

According to the invention a cell preferably is an intact cell, i.e. a cell with an intact membrane that has not released its normal intracellular components such as enzymes, organelles, or genetic material. An intact cell preferably is a viable cell, i.e. a living cell capable of carrying out its normal metabolic functions. Preferably, a cell is a human cell.

A "cell" may be a "host cell" which, as used herein, is intended to refer to a cell into which a recombinant nucleic acid has been introduced.

The terms "transgenic animal" refers to an animal having a genome comprising one or more transgenes, preferably heavy and/or light chain transgenes, or transchromosomes (either integrated or non-integrated into the animal's natural genomic DNA) and which is preferably capable of expressing the transgenes. For example, a transgenic mouse can have a human light chain transgene and either a human heavy chain transgene or human heavy chain transchromosome, such that the mouse produces human anti-CLDN6 antibodies when immunized with CLDN6 antigen and/or cells expressing CLDN6. The human heavy chain transgene can be integrated into the chromosomal DNA of the mouse, as is the case for transgenic mice, e.g., HuMAb mice, such as HCo7 or HCo12 mice, or the human heavy chain transgene can be maintained extrachromosomally, as is the case for transchromosomal (e.g., KM) mice as described in WO 02/43478. Such transgenic and transchromosomal mice may be capable of producing multiple isotypes of human monoclonal antibodies to CLDN6 (e.g., IgG, IgA and/or IgE) by undergoing V-D-J recombination and isotype switching.

According to the invention, the term "therapeutic effector moiety" means any molecule which may exert a therapeutic effect. According to the invention, a therapeutic effector molecule is preferably selectively guided to a cell which expresses CLDN6 and includes anticancer agents, radioisotopes, toxins, cytostatic or cytolytic drugs, etc. Anticancer agents comprise, for example, aminoglutethimide, azathioprine, bleomycin sulfate, busulfan, carmustine, chlorambucil, cisplatin, cyclophosphamide, cyclosporine, cytarabidine, dacarbazine, dactinomycin, daunorubin, doxorubicin, taxol, etoposide, fluorouracil, interferon-$\alpha$, lomustine, mercaptopurine, methotrexate, mitotane, procarbazine HCl, thioguanine, vinblastine sulfate and vincristine sulfate. Other anticancer agents are described, for example, in Goodman and Gilman, "The Pharmacological Basis of Therapeutics", 8th Edition, 1990, McGraw-Hill, Inc., in particular Chapter 52 (Antineoplastic Agents (Paul Calabresi and Bruce A. Chabner). Toxins may be proteins such as pokeweed antiviral protein, cholera toxin, pertussis toxin, ricin, gelonin, abrin, diphtheria exotoxin or *Pseudomonas* exotoxin. Toxin residues may also be high energy-emitting radionuclides such as cobalt-60.

"Reduce" or "inhibit" as used herein means the ability to cause an overall decrease, preferably of 5% or greater, 10% or greater, 20% or greater, more preferably of 50% or greater, and most preferably of 75% or greater, in the level, e.g. in the level of proliferation of cells. The term "inhibit" or similar phrases includes a complete or essentially complete inhibition, i.e. a reduction to zero or essentially to zero.

Terms such as "increase" or "enhance" preferably relate to an increase or enhancement by about at least 10%, preferably at least 20%, preferably at least 30%, more preferably at least 40%, more preferably at least 50%, even more preferably at least 80%, and most preferably at least 100%.

The term "immunologically equivalent" means that the immunologically equivalent molecule such as the immunologically equivalent amino acid sequence exhibits the same or essentially the same immunological properties and/or exerts the same or essentially the same immunological effects, e.g., with respect to the type of the immunological effect such as induction of a humoral and/or cellular immune response, the strength and/or duration of the induced immune reaction, or the specificity of the induced immune reaction. In the context of the present invention, the term "immunologically equivalent" is preferably used with respect to the immunological effects or properties of a peptide or peptide variant used for immunization or an antibody. A particular immunological property is the ability to bind to antibodies and, where appropriate, generate an immune response, preferably by stimulating the generation of antibodies. For example, an amino acid sequence is immunologically equivalent to a reference amino acid sequence if said amino acid sequence when exposed to the immune system of a subject induces an immune reaction, preferably antibodies, having a specificity of reacting with the reference amino acid sequence, such as the reference amino acid sequence forming part of CLDN6.

The term "immune effector functions" in the context of the present invention includes any functions mediated by components of the immune system that result in the inhibition of tumor growth and/or inhibition of tumor development, including inhibition of tumor dissemination and metastasis. Preferably, immune effector functions result in killing of tumor cells. Preferably, the immune effector functions in the context of the present invention are antibody-mediated effector functions. Such functions comprise complement dependent cytotoxicity (CDC), antibody-dependent cell-mediated cytotoxicity (ADCC), induction of apoptosis in the cells carrying the tumor-associated antigen, e.g. CLDN6, for example, by binding of the antibody to a surface antigen, and/or inhibition of proliferation of the cells carrying the tumor-associated antigen, preferably ADCC and/or CDC. Thus, antibodies that are capable of mediating one or more immune effector functions are preferably able to mediate killing of cells by inducing CDC-mediated lysis, ADCC-mediated lysis, apoptosis, homotypic adhesion, and/or phagocytosis, preferably by inducing CDC-mediated lysis and/or ADCC-mediated lysis. Antibodies may also exert an effect simply by binding to tumor-associated antigens on the surface of a tumor cell. For example, antibodies may block the function of the tumor-associated antigen or induce apoptosis just by binding to the tumor-associated antigen on the surface of a tumor cell.

The antibodies, compositions and methods described herein can be used to treat a subject with a tumor disease, e.g., a disease characterized by the presence of tumor cells expressing CLDN6. Examples of tumor diseases which can be treated and/or prevented encompass all CLDN6 expressing cancers and tumor entities including those described herein.

The antibodies, compositions and methods described herein may also be used for immunization or vaccination to prevent a disease described herein.

According to the invention, the term "disease" refers to any pathological state, including cancer, in particular those forms of cancer described herein.

"Diseases involving cells expressing CLDN6" means according to the invention that expression of CLDN6 in cells of a diseased tissue or organ is preferably increased compared to the state in a healthy tissue or organ. An increase refers to an increase by at least 10%, in particular at least 20%, at least 50%, at least 100%, at least 200%, at least 500%, at least 1000%, at least 10000% or even more. In one embodiment, expression is only found in a diseased tissue, while expression in a healthy tissue is repressed. According to the invention, diseases involving or being associated with cells expressing CLDN6 include tumor diseases such as cancer diseases. Furthermore, according to the invention, tumor diseases such as cancer diseases preferably are those wherein the tumor cells or cancer cells express CLDN6.

According to the invention, the term "tumor" or "tumor disease" refers to a swelling or lesion formed by an abnormal growth of cells (called neoplastic cells or tumor cells). By "tumor cell" is meant an abnormal cell that grows by a rapid, uncontrolled cellular proliferation and continues to grow after the stimuli that initiated the new growth cease. Tumors show partial or complete lack of structural organization and functional coordination with the normal tissue, and usually form a distinct mass of tissue, which may be either benign, pre-malignant or malignant.

A benign tumor is a tumor that lacks all three of the malignant properties of a cancer. Thus, by definition, a benign tumor does not grow in an unlimited, aggressive manner, does not invade surrounding tissues, and does not spread to non-adjacent tissues (metastasize). Common examples of benign tumors include moles and uterine fibroids.

The term "benign" implies a mild and nonprogressive disease, and indeed, many kinds of benign tumors are harmless to the health. However, some neoplasms which are defined as "benign tumors" because they lack the invasive properties of a cancer, may still produce negative health effects. Examples of this include tumors which produce a "mass effect" (compression of vital organs such as blood vessels), or "functional" tumors of endocrine tissues, which may overproduce certain hormones (examples include thyroid adenomas, adrenocortical adenomas, and pituitary adenomas).

Benign tumors typically are surrounded by an outer surface that inhibits their ability to behave in a malignant manner. In some cases, certain "benign" tumors may later give rise to malignant cancers, which result from additional genetic changes in a subpopulation of the tumor's neoplastic cells. A prominent example of this phenomenon is the tubular adenoma, a common type of colon polyp which is an important precursor to colon cancer. The cells in tubular adenomas, like most tumors which frequently progress to cancer, show certain abnormalities of cell maturation and appearance collectively known as dysplasia. These cellular abnormalities are not seen in benign tumors that rarely or never turn cancerous, but are seen in other pre-cancerous tissue abnormalities which do not form discrete masses, such as pre-cancerous lesions of the uterine cervix. Some authorities prefer to refer to dysplastic tumors as "pre-malignant", and reserve the term "benign" for tumors which rarely or never give rise to cancer.

Neoplasm is an abnormal mass of tissue as a result of neoplasia. Neoplasia (new growth in Greek) is the abnormal proliferation of cells. The growth of the cells exceeds, and is uncoordinated with that of the normal tissues around it. The growth persists in the same excessive manner even after cessation of the stimuli. It usually causes a lump or tumor. Neoplasms may be benign, pre-malignant or malignant.

"Growth of a tumor" or "tumor growth" according to the invention relates to the tendency of a tumor to increase its size and/or to the tendency of tumor cells to proliferate.

Preferably, a "tumor disease" according to the invention is a cancer disease, i.e. a malignant disease, and a tumor cell is a cancer cell. Preferably, a "tumor disease" is characterized by cells expressing CLDN6 and a tumor cell expresses CLDN6.

Cancer (medical term: malignant neoplasm) is a class of diseases in which a group of cells display uncontrolled growth (division beyond the normal limits), invasion (intrusion on and destruction of adjacent tissues), and sometimes metastasis (spread to other locations in the body via lymph or blood). These three malignant properties of cancers differentiate them from benign tumors, which are self-limited, and do not invade or metastasize. Most cancers form a tumor but some, like leukemia, do not.

A cell expressing CLDN6 preferably is a tumor cell or cancer cell, preferably of the tumors and cancers described herein. Preferably, such cell is a cell other than a placental cell.

Cancers are classified by the type of cell that resembles the tumor and, therefore, the tissue presumed to be the origin of the tumor. These are the histology and the location, respectively.

The term "cancer" according to the invention comprises leukemias, seminomas, melanomas, teratomas, lymphomas, neuroblastomas, gliomas, rectal cancer, endometrial cancer, kidney cancer, adrenal cancer, thyroid cancer, blood cancer, skin cancer, cancer of the brain, cervical cancer, intestinal cancer, liver cancer, colon cancer, stomach cancer, intestine cancer, head and neck cancer, gastrointestinal cancer, lymph node cancer, esophagus cancer, colorectal cancer, pancreas cancer, ear, nose and throat (ENT) cancer, breast cancer, prostate cancer, cancer of the uterus, ovarian cancer and lung cancer and the metastases thereof. Examples thereof are lung carcinomas, mamma carcinomas, prostate carcinomas, colon carcinomas, renal cell carcinomas, cervical carcinomas, or metastases of the cancer types or tumors described above. The term cancer according to the invention also comprises cancer metastases.

Preferred tumor diseases or cancers according to the invention are selected from the group consisting of ovarian cancer, in particular ovarian adenocarcinoma and ovarian teratocarcinoma, lung cancer, including small cell lung cancer (SCLC) and non-small cell lung cancer (NSCLC), in particular squamous cell lung carcinoma and adenocarcinoma, gastric cancer, breast cancer, hepatic cancer, pancreatic cancer, skin cancer, in particular basal cell carcinoma and squamous cell carcinoma, malignant melanoma, head and neck cancer, in particular malignant pleomorphic adenoma, sarcoma, in particular synovial sarcoma and carcinosarcoma, bile duct cancer, cancer of the urinary bladder, in particular transitional cell carcinoma and papillary carcinoma, kidney cancer, in particular renal cell carcinoma including clear cell renal cell carcinoma and papillary renal cell carcinoma, colon cancer, small bowel cancer, including cancer of the ileum, in particular small bowel adenocarcinoma and adenocarcinoma of the ileum, testicular embryonal carcinoma, placental choriocarcinoma, cervical cancer, testicular cancer, in particular testicular seminoma, testicular teratoma and embryonic testicular cancer, and uterine cancer, and the metastatic forms thereof.

Particularly preferred tumor diseases or cancers according to the invention are selected from the group consisting of ovarian cancer, lung cancer, metastatic ovarian cancer and metastatic lung cancer. Preferably, the ovarian cancer is an ovarian carcinoma or an ovarian adenocarcinoma. Preferably, the lung cancer is a carcinoma or an adenocarcinoma, and preferably is bronchiolar cancer such as a bronchiolar carcinoma or bronchiolar adenocarcinoma. In one embodiment, the tumor cell is a cell of such a cancer. Metastatic ovarian cancers include metastatic ovarian carcinomas and metastatic ovarian adenocarcinomas, and metastatic lung cancers include metastatic lung carcinomas, metastatic lung adenocarcinomas, metastatic bronchiolar carcinomas, and metastatic bronchiolar adenocarcinomas.

The main types of lung cancer are small cell lung carcinoma (SCLC) and non-small cell lung carcinoma (NSCLC). There are three main sub-types of the non-small cell lung carcinomas: squamous cell lung carcinoma, adenocarcinoma, and large cell lung carcinoma. Adenocarcinomas account for approximately 10% of lung cancers. This cancer usually is seen peripherally in the lungs, as opposed to small cell lung cancer and squamous cell lung cancer, which both tend to be more centrally located.

Skin cancer is a malignant growth on the skin. The most common skin cancers are basal cell cancer, squamous cell cancer, and melanoma. Malignant melanoma is a serious type of skin cancer. It is due to uncontrolled growth of pigment cells, called melanocytes.

According to the invention, a "carcinoma" is a malignant tumor derived from epithelial cells. This group represents the most common cancers, including the common forms of breast, prostate, lung and colon cancer.

"Bronchiolar carcinoma" is a carcinoma of the lung, thought to be derived from epithelium of terminal bronchioles, in which the neoplastic tissue extends along the alveolar walls and grows in small masses within the alveoli. Mucin may be demonstrated in some of the cells and in the material in the alveoli, which also includes denuded cells.

"Adenocarcinoma" is a cancer that originates in glandular tissue. This tissue is also part of a larger tissue category known as epithelial tissue. Epithelial tissue includes skin, glands and a variety of other tissue that lines the cavities and organs of the body. Epithelium is derived embryologically from ectoderm, endoderm and mesoderm. To be classified as adenocarcinoma, the cells do not necessarily need to be part of a gland, as long as they have secretory properties. This form of carcinoma can occur in some higher mammals, including humans. Well differentiated adenocarcinomas tend to resemble the glandular tissue that they are derived from, while poorly differentiated may not. By staining the cells from a biopsy, a pathologist will determine whether the tumor is an adenocarcinoma or some other type of cancer. Adenocarcinomas can arise in many tissues of the body due to the ubiquitous nature of glands within the body. While each gland may not be secreting the same substance, as long as there is an exocrine function to the cell, it is considered glandular and its malignant form is therefore named adenocarcinoma. Malignant adenocarcinomas invade other tissues and often metastasize given enough time to do so. Ovarian adenocarcinoma is the most common type of ovarian carcinoma. It includes the serous and mucinous adenocarcinomas, the clear cell adenocarcinoma and the endometrioid adenocarcinoma.

"Cystadenocarcinoma" is a malignant form of a surface epithelial-stromal tumor, a type of ovarian cancer.

Surface epithelial-stromal tumors are a class of ovarian neoplasms that are thought to be derived from the ovarian surface epithelium (modified peritoneum) or from ectopic endometrial or Fallopian tube (tubal) tissue. This group of tumors accounts for the majority of all ovarian tumors.

"Choriocarcinoma" is a malignant, trophoblastic and aggressive cancer, usually of the placenta. It is characterized by early hematogenous spread to the lungs.

Renal cell carcinoma also known as renal cell cancer or renal cell adenocarcinoma is a kidney cancer that originates in the lining of the proximal convoluted tubule, the very small tubes in the kidney that filter the blood and remove waste products. Renal cell carcinoma is by far the most common type of kidney cancer in adults and the most lethal of all the genitorurinary tumors. Distinct subtypes of renal cell carcinoma are clear cell renal cell carcinoma and papillary renal cell carcinoma. Clear cell renal cell carcinoma is the most common form of renal cell carcinoma. When seen under a microscope, the cells that make up clear cell renal cell carcinoma appear very pale or clear. Papillary renal cell carcinoma is the second most common subtype. These cancers form little finger-like projections (called papillae) in some, if not most, of the tumors.

A sarcoma is a malignant tumor derived from connective tissue, or mesenchymal cells. This is in contrast to carcinomas, which are of epithelial origin. A synovial sarcoma is a rare form of cancer which usually occurs near to the joints of the arm or leg. It is one of the soft tissue sarcomas.

A germ cell tumor is a neoplasm derived from germ cells. Germ cell tumors can be cancerous or non-cancerous tumors. Germ cells normally occur inside the gonads (ovary and testis). Germ cell tumors that originate outside the gonads (e.g. in head, inside the mouth, neck, pelvis; in fetuses, babies, and young children most often found on the body midline, particularly at the tip of the tailbone) may be birth defects resulting from errors during development of the embryo.

The two major classes of germ cell tumors are the seminomas and non-seminomas, wherein non-seminomas include: teratocarcinoma, embryonal carcinoma, yolk sac tumors, choriocarcinoma and differentiated teratoma. Most cell lines from non-seminomas are equivalent to embryonal carcinomas, that is, they are composed almost entirely of stem cells which do not differentiate under basal conditions, though some may respond to inducers of differentiation such as retinoic acid.

Teratocarcinoma refers to a germ cell tumor that is a mixture of teratoma with embryonal carcinoma, or with choriocarcinoma, or with both. This kind of mixed germ cell tumor may be known simply as a teratoma with elements of embryonal carcinoma or choriocarcinoma, or simply by ignoring the teratoma component and referring only to its malignant component: embryonal carcinoma and/or choriocarcinoma.

Lymphoma and leukemia are malignancies derived from hematopoietic (blood-forming) cells.

Blastic tumor or blastoma is a tumor (usually malignant) which resembles an immature or embryonic tissue. Many of these tumors are most common in children.

By "metastasis" is meant the spread of cancer cells from its original site to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor, i.e. a secondary tumor or metastatic tumor, at the target site depends on angiogenesis. Tumor metastasis often occurs even after the removal of the primary tumor because tumor cells or components may remain and develop metastatic potential. In one embodiment, the term "metastasis" according to the invention relates to "distant metastasis" which relates to a metastasis which is remote from the primary tumor and the regional lymph node system.

The cells of a secondary or metastatic tumor are like those in the original tumor. This means, for example, that, if ovarian cancer metastasizes to the liver, the secondary tumor is made up of abnormal ovarian cells, not of abnormal liver cells. The tumor in the liver is then called metastatic ovarian cancer, not liver cancer.

In ovarian cancer, metastasis can occur in the following ways: by direct contact or extension, it can invade nearby tissue or organs located near or around the ovary, such as the fallopian tubes, uterus, bladder, rectum, etc.; by seeding or shedding into the abdominal cavity, which is the most common way ovarian cancer spreads. Cancer cells break off the surface of the ovarian mass and "drop" to other structures in the abdomen such as the liver, stomach, colon or diaphragm; by breaking loose from the ovarian mass, invading the lymphatic vessels and then traveling to other areas of the body or distant organs such as the lung or liver; by breaking loose from the ovarian mass, invading the blood system and traveling to other areas of the body or distant organs.

According to the invention, metastatic ovarian cancer includes cancer in the fallopian tubes, cancer in organs of the abdomen such as cancer in the bowel, cancer in the uterus, cancer in the bladder, cancer in the rectum, cancer in the liver, cancer in the stomach, cancer in the colon, cancer in the diaphragm, cancer in the lungs, cancer in the lining of the abdomen or pelvis (peritoneum), and cancer in the brain. Similarly, metastatic lung cancer refers to cancer that has spread from the lungs to distant and/or several sites in the body and includes cancer in the liver, cancer in the adrenal glands, cancer in the bones, and cancer in the brain.

A relapse or recurrence occurs when a person is affected again by a condition that affected them in the past. For example, if a patient has suffered from a tumor disease, has received a successful treatment of said disease and again develops said disease said newly developed disease may be considered as relapse or recurrence. However, according to the invention, a relapse or recurrence of a tumor disease may but does not necessarily occur at the site of the original tumor disease. Thus, for example, if a patient has suffered from ovarian tumor and has received a successful treatment a relapse or recurrence may be the occurrence of an ovarian tumor or the occurrence of a tumor at a site different to ovary. A relapse or recurrence of a tumor also includes situations wherein a tumor occurs at a site different to the site of the original tumor as well as at the site of the original tumor. Preferably, the original tumor for which the patient has received a treatment is a primary tumor and the tumor at a site different to the site of the original tumor is a secondary or metastatic tumor.

By "treat" is meant to administer a compound or composition as described herein to a subject in order to: prevent or eliminate a tumor or reduce the size of a tumor or the number of tumors in a subject; arrest or slow the growth of a tumor in a subject; inhibit or slow the development of a new tumor or tumor metastasis in a subject; decrease the frequency or severity of symptoms and/or recurrences in a subject who currently has or who previously has had cancer; and/or prolong, i.e. increase the lifespan of the subject.

In particular, the term "treatment of a disease" includes curing, shortening the duration, ameliorating, preventing, slowing down or inhibiting progression or worsening, or preventing or delaying the onset of a disease or the symptoms thereof.

By "being at risk" is meant a subject, i.e. a patient, that is identified as having a higher than normal chance of developing a tumor disease, in particular cancer, compared to the general population. In addition, a subject who has had, or who currently has, a tumor disease, in particular cancer is a subject who has an increased risk for developing cancer, as such a subject may continue to develop cancer. Subjects who currently have, or who have had, a tumor also have an increased risk for tumor metastases.

The term "immunotherapy" relates to a treatment involving a specific immune reaction. In the context of the present invention, terms such as "protect", "prevent", "prophylactic", "preventive", or "protective" relate to the prevention or treatment or both of the occurrence and/or the propagation of a tumor in an individual and, in particular, to minimizing the chance that a subject will develop a tumor or to delaying the development of a tumor. For example, a person at risk for a tumor, as described above, would be a candidate for therapy to prevent a tumor.

A prophylactic administration of an immunotherapy, for example, a prophylactic administration of the composition of the invention, preferably protects the recipient from the development of tumor growth. A therapeutic administration of an immunotherapy, for example, a therapeutic administration of the composition of the invention, may lead to the inhibition of the progress/growth of the tumor. This comprises the deceleration of the progress/growth of the tumor, in particular a disruption of the progression of the tumor, which preferably leads to elimination of the tumor.

The term "in vivo" relates to the situation in a subject.

The terms "subject", "individual" or "patient" are used interchangeably and relate to vertebrates, preferably mammals. For example, mammals in the context of the present invention are humans, non-human primates, domesticated animals such as dogs, cats, sheep, cattle, goats, pigs, horses etc., laboratory animals such as mice, rats, rabbits, guinea pigs, etc. as well as animals in captivity such as animals of zoos. The term "animal" as used herein also includes humans. The term "subject" may also include a patient, i.e., an animal, preferably a human having a disease, preferably a disease associated with expression of CLDN6, preferably a tumor disease such as a cancer.

As part of the composition for an immunization or a vaccination, preferably one or more agents as described herein are administered together with one or more adjuvants for inducing an immune response or for increasing an immune response. The term "adjuvant" relates to compounds which prolongs or enhances or accelerates an immune response. The composition of the present invention preferably exerts its effect without addition of adjuvants. Still, the composition of the present application may contain any known adjuvant. Adjuvants comprise a heterogeneous group of compounds such as oil emulsions (e.g., Freund's adjuvants), mineral compounds (such as alum), bacterial products (such as *Bordetella pertussis* toxin), liposomes, and immune-stimulating complexes. Examples for adjuvants are monophosphoryl-lipid-A (MPL SmithKline Beecham). Saponins such as QS21 (SmithKline Beecham), DQS21 (SmithKline Beecham; WO 96/33739), QS7, QS17, QS18, and QS-L1 (So et al., 1997, Mol. Cells 7: 178-186), incomplete Freund's adjuvants, complete Freund's adjuvants, vitamin E, montanid, alum, CpG oligonucleotides (Krieg et al., 1995, Nature 374: 546-549), and various water-in-oil emulsions which are prepared from biologically degradable oils such as squalene and/or tocopherol.

According to the invention, a "sample" may be any sample useful according to the present invention, in particular a biological sample such a tissue sample, including bodily fluids, and/or a cellular sample and may be obtained in the conventional manner such as by tissue biopsy, including punch biopsy, and by taking blood, bronchial aspirate, sputum, urine, feces or other body fluids. According to the invention, the term "sample" also includes processed samples such as fractions or isolates of biological samples, e.g. nucleic acid and peptide/protein isolates.

Other substances which stimulate an immune response of the patient may also be administered. It is possible, for example, to use cytokines in a vaccination, owing to their regulatory properties on lymphocytes. Such cytokines comprise, for example, interleukin-12 (IL-12) which was shown to increase the protective actions of vaccines (Hall (1995) Science 268: 1432-1434), GM-CSF and IL-18.

There are a number of compounds which enhance an immune response and which therefore may be used in a vaccination. Said compounds comprise costimulating molecules provided in the form of proteins or nucleic acids such as B7-1 and B7-2 (CD80 and CD86, respectively).

The therapeutically active compounds of the invention may be administered via any conventional route, including by injection or infusion. The administration may be carried out, for example, orally, intravenously, intraperitonealy, intramuscularly, subcutaneously or transdermally. Preferably, antibodies are therapeutically administered by way of a lung aerosol.

In a further embodiment, antibodies of the invention can be formulated to prevent or reduce their transport across the placenta. This can be done by methods known in the art, e.g., by PEGylation of the antibodies or by use of F(ab)2' fragments. Further references can be made to "Cunningham-Rundles C, Zhuo Z, Griffith B, Keenan J. (1992) Biological activities of polyethylene-glycol immunoglobulin conjugates. Resistance to enzymatic degradation. J. Immunol. Methods, 152: 177-190; and to "Landor M. (1995) Maternal-fetal transfer of immunoglobulins, Ann. Allergy Asthma Immunol. 74: 279-283.

The compositions of the invention are administered in effective amounts. An "effective amount" refers to the amount which achieves a desired reaction or a desired effect alone or together with further doses. In the case of treatment of a particular disease or of a particular condition, the desired reaction preferably relates to inhibition of the course of the disease. This comprises slowing down the progress of the disease and, in particular, interrupting or reversing the progress of the disease. The desired reaction in a treatment of a disease or of a condition may also be delay of the onset or a prevention of the onset of said disease or said condition.

An effective amount of a composition of the invention will depend on the condition to be treated, the severeness of the disease, the individual parameters of the patient, including age, physiological condition, size and weight, the duration of treatment, the type of an accompanying therapy (if present), the specific route of administration and similar factors. Accordingly, the doses of the compositions of the invention administered may depend on various of such parameters. In the case that a reaction in a patient is insufficient with an initial dose, higher doses (or effectively higher doses achieved by a different, more localized route of administration) may be used.

The pharmaceutical compositions of the invention are preferably sterile and contain an effective amount of the therapeutically active substance to generate the desired reaction or the desired effect.

The pharmaceutical compositions of the invention are generally administered in pharmaceutically compatible amounts and in pharmaceutically compatible preparation. The term "pharmaceutically compatible" refers to a nontoxic material which does not interact with the action of the active component of the pharmaceutical composition. Preparations of this kind may usually contain salts, buffer substances, preservatives, carriers, supplementing immunity-enhancing substances such as adjuvants, e.g. CpG oligonucleotides, cytokines, chemokines, saponin, GM-CSF and/or RNA and, where appropriate, other therapeutically active compounds. When used in medicine, the salts should be pharmaceutically compatible. However, salts which are not pharmaceutically compatible may used for preparing pharmaceutically compatible salts and are included in the invention. Pharmacologically and pharmaceutically compatible salts of this kind comprise in a nonlimiting way those prepared from the following acids: hydrochloric, hydrobromic, sulfuric, nitric, phosphoric, maleic, acetic, salicylic, citric, formic, malonic, succinic acids, and the like. Pharmaceutically compatible salts may also be prepared as alkali metal salts or alkaline earth metal salts, such as sodium salts, potassium salts or calcium salts.

A pharmaceutical composition of the invention may comprise a pharmaceutically compatible carrier. The term "carrier" refers to an organic or inorganic component, of a natural or synthetic nature, in which the active component is combined in order to facilitate application. According to the invention, the term "pharmaceutically compatible carrier" includes one or more compatible solid or liquid fillers, diluents or encapsulating substances, which are suitable for administration to a patient. The components of the pharmaceutical composition of the invention are usually such that no interaction occurs which substantially impairs the desired pharmaceutical efficacy.

The pharmaceutical compositions of the invention may contain suitable buffer substances such as acetic acid in a salt, citric acid in a salt, boric acid in a salt and phosphoric acid in a salt.

The pharmaceutical compositions may, where appropriate, also contain suitable preservatives such as benzalkonium chloride, chlorobutanol, paraben and thimerosal.

The pharmaceutical compositions are usually provided in a uniform dosage form and may be prepared in a manner known per se. Pharmaceutical compositions of the invention may be in the form of capsules, tablets, lozenges, solutions, suspensions, syrups, elixirs or in the form of an emulsion, for example.

Compositions suitable for parenteral administration usually comprise a sterile aqueous or nonaqueous preparation of the active compound, which is preferably isotonic to the blood of the recipient. Examples of compatible carriers and solvents are Ringer solution and isotonic sodium chloride solution. In addition, usually sterile, fixed oils are used as solution or suspension medium.

The present invention is described in detail by the figures and examples below, which are used only for illustration purposes and are not meant to be limiting. Owing to the description and the examples, further embodiments which are likewise included in the invention are accessible to the skilled worker.

EXAMPLES

The techniques and methods used herein are described herein or carried out in a manner known per se and as described, for example, in Sambrook et al., Molecular Cloning: A Laboratory Manual, 2nd Edition (1989) Cold Spring Harbor Laboratory Press, Cold Spring Harbor, N.Y. All methods including the use of kits and reagents are carried out according to the manufacturers' information unless specifically indicated.

Example 1: Materials and Methods

A. Generation of Murine Antibodies Against CLDN6 a. Generation of Expression Vectors Encoding Full Length CLDN6 and CLDN6 Fragments A non-natural, codon-optimized DNA sequence (SEQ ID NO: 10) encoding full length CLDN6 (SEQ ID NO: 2) was prepared by chemical synthesis (GENEART AG, Germany) and cloned into the pcDNA3.1/myc-His vector (Invitrogen, USA) yielding the vector p3953. Insertion of a stop codon allowed the expression of CLDN6 protein without being fused to the vector encoded myc-His tag. Expression of CLDN6 was tested by Western blot, flow cytometry and immunofluorescence analyses using commercially available anti-CLDN6 antibodies (ARP, 01-8865; R&D Systems, MAB3656).

In addition, a codon-optimized DNA sequence (SEQ ID NO: 11) coding for the putative extracellular domain 2 (EC2) fragment of CLDN6 (SEQ ID NO: 5) as a fusion with an N-terminal Ig kappa leader derived signal peptide followed by 4 additional amino acids to ensure a correct signal peptidase cleavage site (SEQ ID NO: 12) was prepared and cloned into the pcDNA3.1/myc-His vector yielding the vector p3974. Prior to immunization, expression of the EC2 fragment was confirmed by immunofluorescence microscopy on transiently transfected and paraformaldehyde (PFA)-fixed CHO-K1 cells using a commercially available anti-myc antibody (Cell Signaling, MAB 2276).

b. Generation of Cell Lines Stably Expressing CLDN6

HEK293 and P3X63Ag8U.1 cell lines stably expressing CLDN6 were generated by standard techniques using the vector p3953.

c. Immunizations

MuMAB 5F2D2: Balb/c mice were immunized with 25 µg of p3974 plasmid DNA together with 4 µl PEI-mannose (PEI-Man; in vivo-jetPEI™-Man from PolyPlus Transfection) (150 mM PEI-Man in $H_2O$ with 5% Glucose) by intraperitoneal injection on days 0, 16 and 36. On days 48 and 62 mice were immunized by intraperitoneal injection with $2 \times 10^7$ P3X63Ag8U.1 myeloma cells transfected with p3953 vector to stably express CLDN6. The cells administered on day 62 had been irradiated with 3000 rad prior to injection.

MuMAB 27A: Balb/c mice were immunized by intraperitonal injection with $2 \times 10^7$ P3X63Ag8U.1 myeloma cells transfected with p3953 vector to stably express CLDN6 on day 0 and 13. Mice developing tumors were boosted by intraperitonal injection with $2 \times 10^7$ HEK293 cells stably transfected with p3953 vector on day 21. After three days, mice were sacrificed and splenocytes were prepared. $5 \times 10^7$ splenocytes were transplanted into another Balb/c mouse by intravenous injection. On day 35, 49, 67 and 104 the transplanted mice were immunized by intraperitoneal injection with $2 \times 10^7$ P3X63Ag8U.1 myeloma cells stably transfected with p3953 vector together with HPLC-purified phosphorothioate-modified CpG oligodeoxynucleotides (PTO-CpG-ODN) (50 µg; 5'-TCCATGACGTTCCTGACGTT; Eurofins MWG Operon, Germany). Prior administration, the cells were treated with mitomycin-C (5 µg/ml, Sigma-Aldrich, M4287).

MuMAB 36A: C57BL/6 mice were immunized with 25 µg of p3974 plasmid DNA together with 4 µl PEI-mannose (PEI-Man; in vivo-jetPEI™-Man from PolyPlus Transfection) (150 mM PEI-Man in $H_2O$ with 5% Glucose) by intraperitoneal injection on days 0, 16 and 36. On days 55, 69 and 85 mice were immunized by intraperitoneal injection with $2 \times 10^7$ P3X63Ag8U.1 myeloma cells transfected with p3953 vector to stably express CLDN6. On day 85 cells were administered together with HPLC-purified PTO-CpG-ODN (50 µg in PBS; 5'-TCCATGACGTTCCTGACGTT; Eurofins MWG Operon, Germany).

The presence of antibodies directed against CLDN6 in sera of mice was monitored by immunofluorescence microscopy using CHO-K1 cells co-transfected with nucleic acids encoding CLDN6 and GFP. To this end, 24 h following transfection, PFA-fixed or non-fixed cells were incubated with a 1:100 dilution of sera from immunized mice for 45 min at room temperature (RT). Cells were washed, incubated with an Alexa555-labeled anti-mouse Ig antibody (Molecular Probes) and subjected to fluorescence microscopy.

For generation of monoclonal antibodies, mice with detectable anti-CLDN6 immune responses were boosted four days prior to splenectomy by intraperitonal injection of $2 \times 10^7$ HEK293 cells stably transfected with p3953 vector.

d. Generation of Hybridomas Producing Murine Monoclonal Antibodies Against CLDN6

$6 \times 10^7$ splenocytes isolated from an immunized mouse were fused with $3 \times 10^7$ cells of the mouse myeloma cell line P3X63Ag8.653 (ATCC, CRL 1580) using PEG 1500 (Roche, CRL 10783641001). Cells were seeded at approximately $5 \times 10^4$ cells per well in flat bottom microtiter plates and cultivated for about two weeks in RPMI selective medium containing 10% heat inactivated fetal bovine serum, 1% hybridoma fusion and cloning supplement (HFCS, Roche, CRL 11363735), 10 mM HEPES, 1 mM sodium pyruvate, 4.5% glucose, 0.1 mM 2-mercaptoethanol, 1×penicillin/streptomycin and 1×HAT supplement (Invitrogen, CRL 21060). After 10 to 14 days, individual wells were screened by flow cytometry for anti-CLDN6 monoclonal antibodies. Antibody secreting hybridomas were subcloned by limiting dilution and again tested for anti-CLDN6 monoclonal antibodies. The stable subclones were cultured to generate small amounts of antibody in tissue culture medium for characterization. At least one clone from each hybridoma which retained the reactivity of the parent cells (tested by flow cytometry) was selected. Nine-vial-cell banks were generated for each clone and stored in liquid nitrogen.

B. Flow Cytometry

To test the binding of monoclonal antibodies to CLDN6 and other claudins HEK293T cells were transiently transfected with the corresponding claudin-coding plasmid and the expression was analyzed by flow cytometry. In order to differentiate between transfected and non-transfected cells, HEK293T cells were co-transfected with a fluorescence marker as a reporter. 24 h post transfection cells were harvested with 0.05% Trypsin/EDTA, washed with FACS buffer (PBS containing 2% FCS and 0.1% sodium azide) and resuspended in FACS buffer at a concentration of $2 \times 10^6$ cells/ml. 100 µl of the cell suspension were incubated with the appropriate antibody at indicated concentrations for 30 min at 4° C. The commercially available mouse anti-claudin antibodies anti-CLDN6 (R&D, CRL MAB3656), anti-CLDN3 (R&D, MAB4620) and anti-CLDN4 (R&D, MAB4219) served as positive controls, whereas mouse IgG2b (Sigma, CRL M8894) served as isotype control. The cells were washed three times with FACS buffer and incubated with an allophycocyanin (APC)-conjugated anti-mouse IgG 1+2a+2b+3a specific secondary antibody (Dianova, CRL 115-135-164) for 30 min at 4° C. The cells were washed twice and resuspended in FACS buffer. The binding was analyzed by flow cytometry using a BD FACSArray. The expression of the fluorescence marker was plotted on the horizontal axis against the antibody binding on the vertical axis.

The binding of monoclonal antibodies to cell lines that endogenously express CLDN6 was analyzed in a similar manner.

C. Immunoblot Analysis

NEC8 cells were analyzed for CLDN6, 3, 4 and 9 expression by immunoblot analysis. As positive control HEK293T cells were transiently transfected with either CLDN6, 3, 4, 9 or a mock plasmid as negative control. Cells were harvested in Laemmli buffer, lysed and subjected to SDS-PAGE. The gel was blotted and stained with an anti-CLDN3 (Invitrogen, 34-1700), anti-CLDN4 (Invitrogen, 32-9400), anti-CDLN6 (ARP, 01-8865) or anti-CLDN9 (Santa Cruz, sc-17672) antibody, respectively. After incubation with a peroxidase labelled secondary antibody the blot was developed with ECL reagent and visualized using a LAS-3000 imager (Fuji).

D. CDC Analysis

Complement dependent cytotoxicity (CDC) was determined by measuring the content of intracellular ATP in non-lysed cells after the addition of human complement to the target cells incubated with anti-CLDN6 antibodies. As a very sensitive analytical method the bioluminescent reaction of luciferase was used for measuring ATP.

CHO-K1 cells stably transfected with CLDN6 (CHO-K1-CLDN6) were harvested with 0.05% Trypsin/EDTA, washed twice with X-Vivo 15 medium (Lonza, BE04-418Q) and suspended at a concentration of 1×10⁷ cells/ml in X-Vivo 15 medium. 250 µl of the cell suspension were transferred into a 0.4 cm electroporation cuvette and mixed with 7 µg of in vitro transcribed RNA encoding for luciferase (luciferase IVT RNA). The cells were electroporated at 200 V and 300 µF using a Gene Pulser Xcell (Bio Rad). After electroporation, the cells were suspended in 2.4 ml pre-warmed D-MEM/F12 (1:1) with GlutaMax-I medium (Invitrogen, 31331-093) containing 10% (v/v) FCS, 1% (v/v) penicillin/streptomycin and 1.5 mg/ml G418. 50 µl of the cell suspension per well were seeded into a white 96-well PP-plate and incubated at 37° C. and 7.5% $CO_2$. 24 h post electroporation 50 µl monoclonal murine anti-CLDN6 antibodies in 60% RPMI (containing 20 mM HEPES) and 40% human serum (serum pool obtained from six healthy donors) were added to the cells at indicated concentrations. 10 µl 8% (v/v) Triton X-100 in PBS per well were added to total lysis controls, whereas 10 µl PBS per well were added to max viable cells controls and to the actual samples. After an incubation of 80 min at 37° C. and 7.5% $CO_2$ 50 luciferin mix (3.84 mg/ml D-luciferin, 0.64 U/ml ATPase and 160 mM HEPES in $ddH_2O$) were added per well. The plate was incubated in the dark for 45 min at RT. The bioluminescence was measured using a luminometer (Infinite M200, TECAN). Results are given as integrated digital relative light units (RLU).

The specific lysis is calculated as follows:

$$\text{specific lysis } [\%] = 100 - \left[\frac{(\text{sample} - \text{total lysis})}{(\text{max}[\text{viable cells} - \text{total lysis}])} \times 100\right]$$

max viable cells: 10 µl PBS, without antibody total lysis: 10 µl 8% (v/v) Triron X – 100 in PBS, without antibody E. ADCC Analysis Chimerized monoclonal anti-CLDN6 antibodies were analysed for their capability to induce antibody-dependent cellular cytotoxicity (ADCC) against endogenously CLDN6 expressing NEC8 cells and NEC8 cells with CLDN6 knockdown (NEC8 LVTS2 54) in a luciferase-based assay system.

NEC8 or NEC8 LVTS2 54 target cells were harvested with 0.05% Trypsin/EDTA, washed twice with X-Vivo 15 medium and 2.5×10⁶ cells were electroporated with 7 µg luciferase IVT RNA (200 V, 400 µF) using a Gene Pulser Xcell (Bio Rad). After electroporation, the cells were suspended in 2.4 ml pre-warmed RPMI containing 10% FCS. 50 µl of the cell suspension (5×10⁴ cells) per well were seeded into a white 96-well PP-plate and incubated at 37° C., 5% $CO_2$ for 6 h. Human peripheral blood mononuclear cells (PBMCs) were enriched from the blood of healthy donors using Ficoll (Ficoll-Paque™ Plus, GE Healthcare, 17-1440-03). The PBMCs were suspended in X-Vivo 15 (Lonza, BE04-418Q) supplemented with 5% heat-inactivated human serum and incubated at 37° C. and 5% $CO_2$. After incubation for 2-4 h the supernatant was enriched in natural killer (NK) cells. 25 µl antibodies diluted in PBS at indicated concentrations were added to NEC8 cells. Enriched NK cells were added at a ratio of 20:1 (effector to target cells) and the samples were incubated for 24 h at 37° C. and 5% $CO_2$. Lysis of cells was determined by measuring the content of intracellular ATP with luciferase as described in "CDC".

F. Early Treatment Assay

For early antibody treatments 5×10⁶ HEK293-CLDN6 cells (HEK293 cells stably expressing CLDN6) in 200 µl PBS were subcutaneously inoculated into the flank of athymic Nude-Foxn1$^{nu}$ mice. HEK293-mock cells were used as negative controls. Each experimental group consisted of eight 6-8 week-old female mice. (In case of mice engrafted with HEK293-CLDN6 or -mock cells, respectively, the saline control groups consisted of ten mice.) Three days after inoculation 200 µg of purified murine monoclonal antibodies muMAB 5F2D2, 27A and 36A were applied for 46 days by alternating intravenous and intraperitoneal injections twice a week. Experimental groups treated with PBS served as a negative controls. The tumor volume (TV=(length×width²)/2) was monitored bi-weekly. TV is expressed in mm³, allowing construction of tumor growth curves over time. When the tumor reached a volume greater than 1500 mm³ mice were killed.

Example 2: Binding of Antibodies Obtained According to the Invention to Claudins The binding of the murine monoclonlal antibodies muMAB 5F2D2, 27A and 36A to human CLDN6, 3, 4 and 9 was analyzed by flow cytometry using HEK293T cells transiently expressing the corresponding human claudin. HEK293T were co-transfected with a fluorescence marker to distinguish between non-transfected (Q3 population) and transfected (Q4 population) cells. The antibody concentration used was the concentration that saturated binding to CLDN6 (25 µg/ml). The expression of human CLDN6, 3, 4 and 9 was confirmed with commercially available monoclonal antibodies against human Claudin-6 (R&D Systems, MAB3656), human Claudin-3 (R&D Systems, MAB4620) and human Claudin-4 (R&D Systems, MAB 4219).

Figure 1:
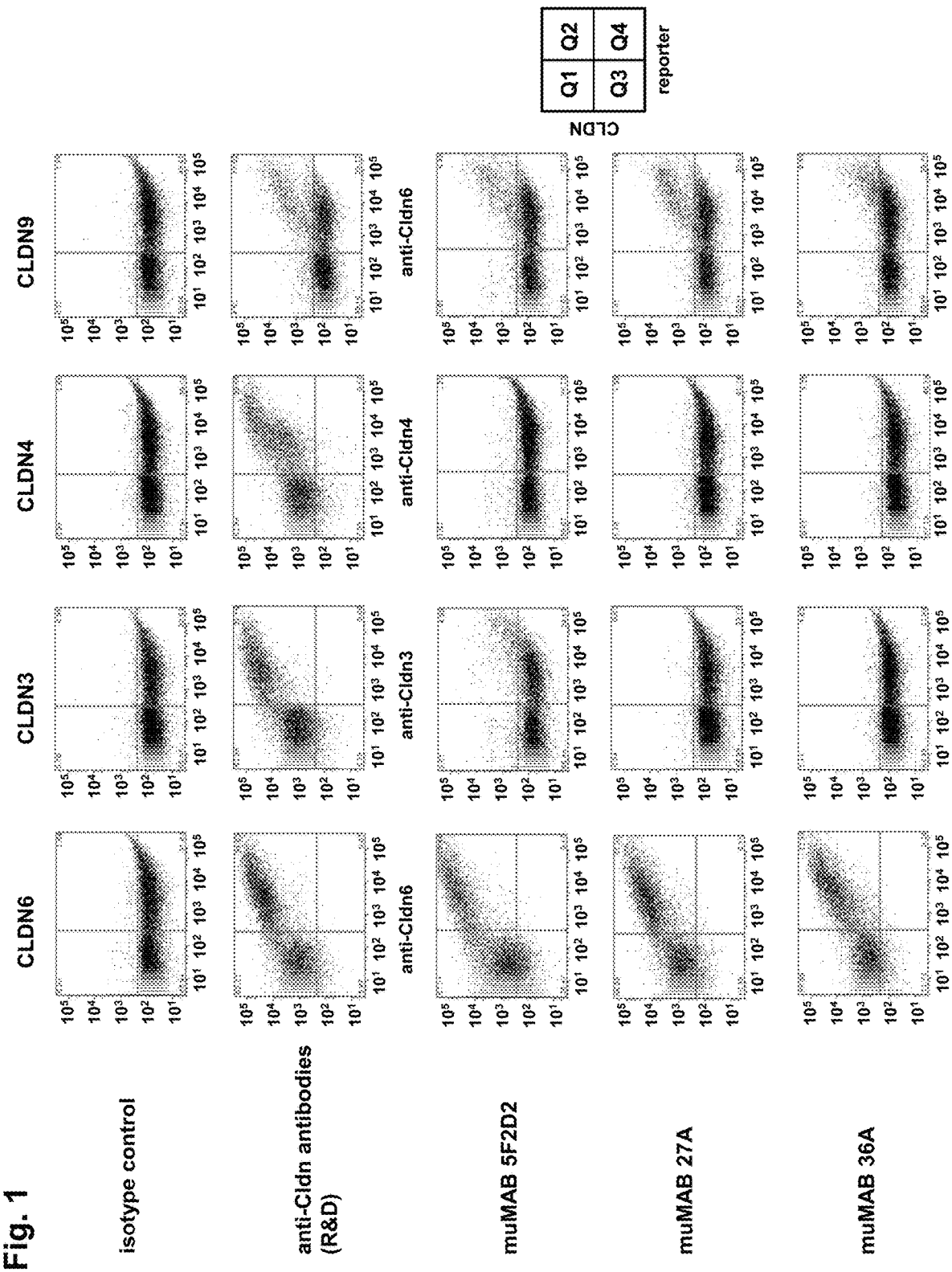
FIG. 1:
Binding specificity of anti-CLDN6 murine monoclonal antibodies muMAB 5F2D2, 27A and 36A.
MuMAB 5F2D2, 27A and 36A antibodies strongly bind to cells expressing CLDN6, while they do not bind to cells expressing CLDN3 or CLDN4.

MuMAB 5F2D2, 27A and 36A antibodies showed strong binding to cells expressing CLDN6, while they did not bind to cells expressing CLDN3 or CLDN4; see FIG. 1.

Figure 2:
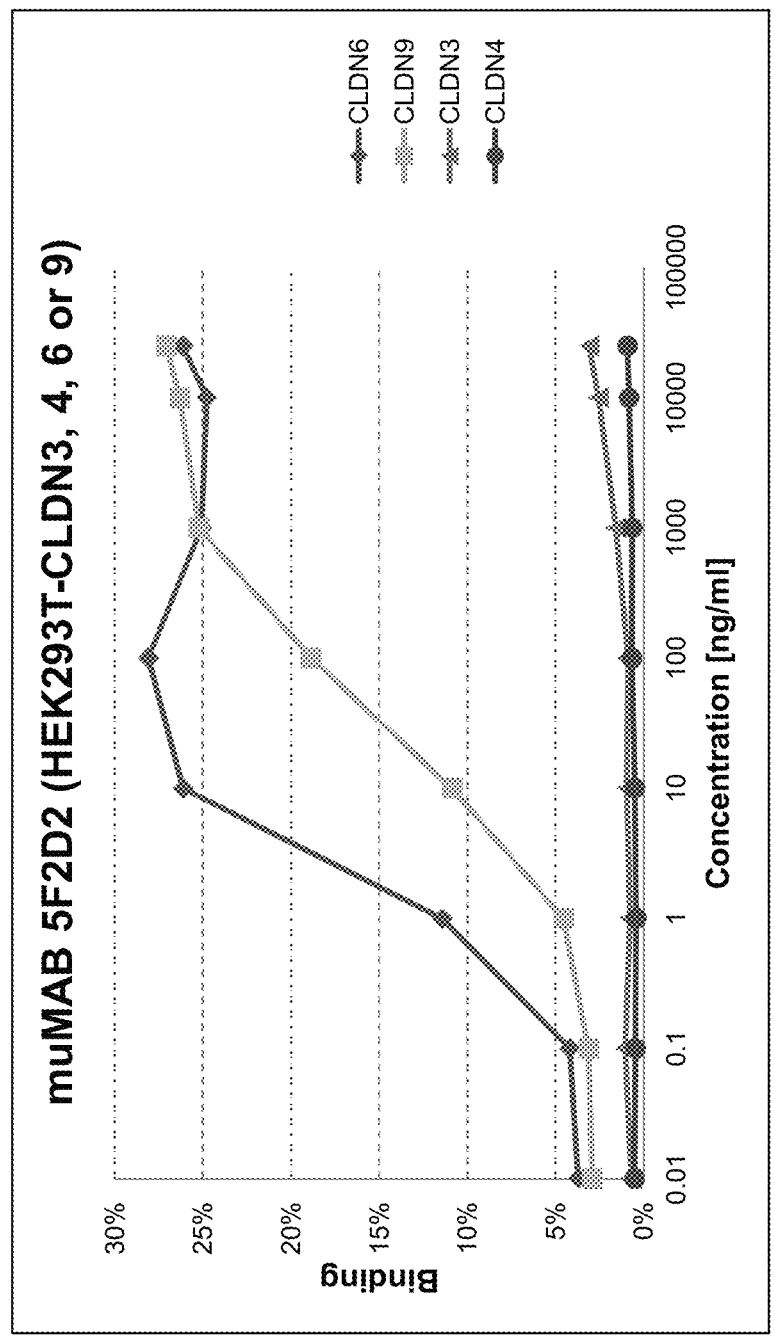
FIG. 2:
Titration of muMAB 5F2D2 binding to HEK293T cells transiently transfected with CLDN6, 3, 4 or 9, respectively.
MuMAB 5F2D2 shows strong binding to human CLDN6 and weak binding to human CLDN9. The antibody does not interact with either human CLDN3 or 4.
Figure 3:
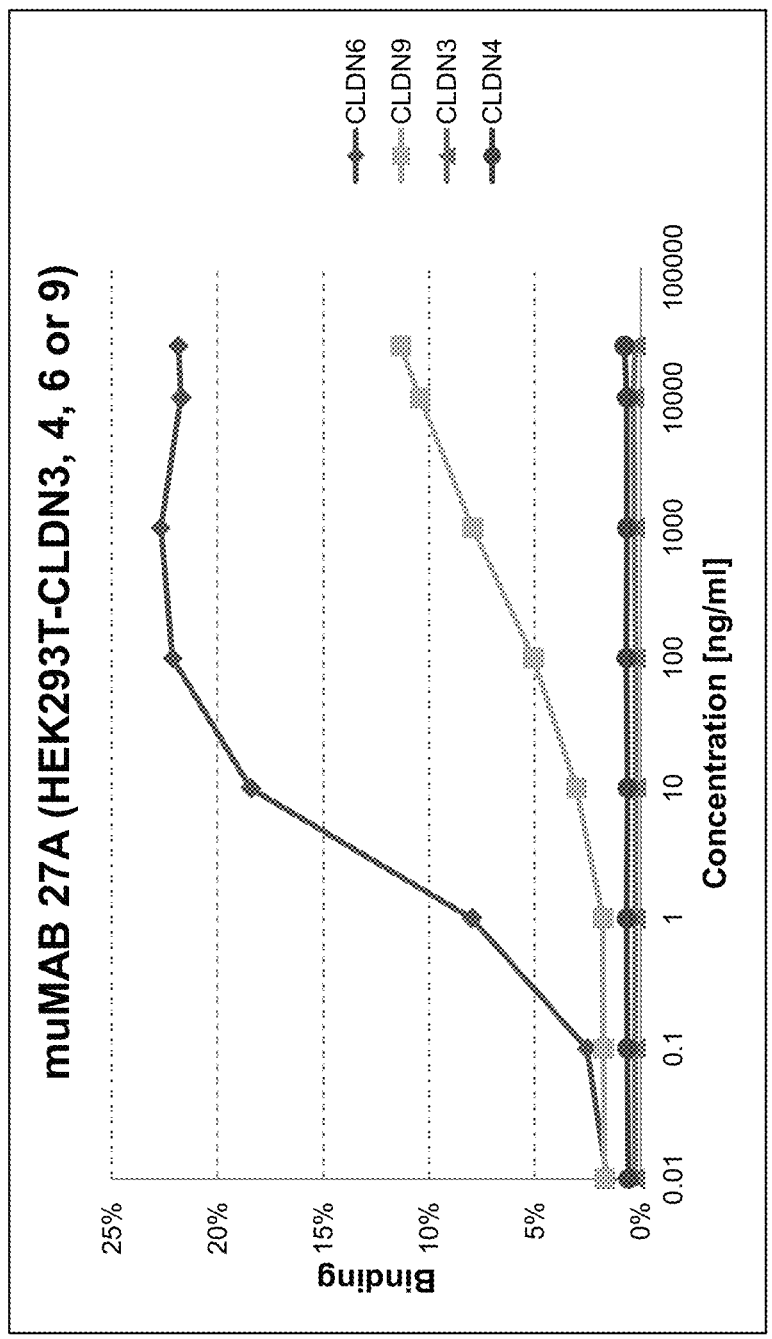
FIG. 3:
Titration of muMAB 27A binding to HEK293T cells transiently transfected with CLDN6, 3, 4 or 9, respectively.
MuMAB 27A shows strong binding to human CLDN6 and very weak binding to human CLDN9. The antibody does not interact with either human CLDN3 or 4.
Figure 4:
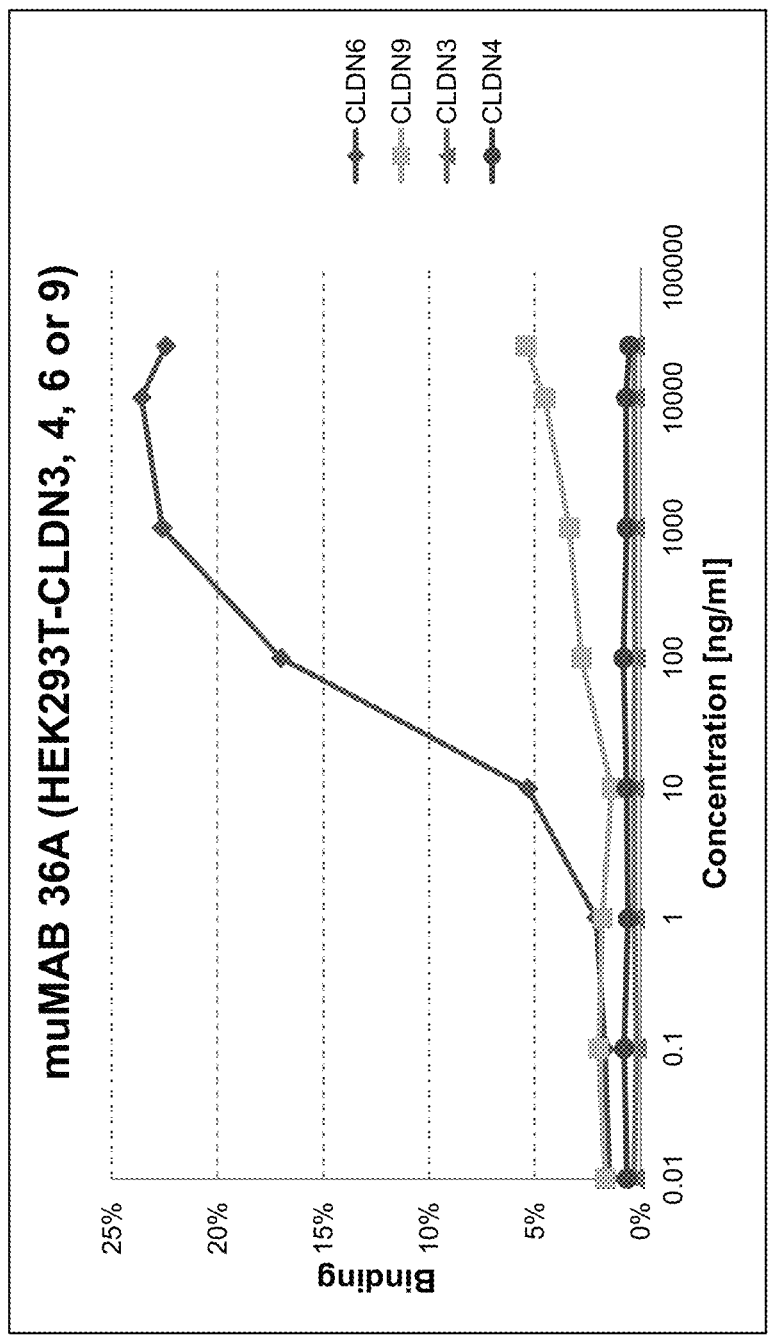
FIG. 4:
Titration of muMAB 36A binding to HEK293T cells transiently transfected with CLDN6, 3, 4 or 9, respectively.
MuMAB 36A shows strong binding to human CLDN6 and virtually no binding to human CLDN9. The antibody does not interact with either human CLDN3 or 4.

MuMAB 5F2D2, 27A and 36A antibodies were incubated at different concentrations (0.01, 0.1, 1, 10, 100, 1000, 10000 and 25000 ng/ml) with HEK293T cells transiently expressing human CLDN6, CLDN3, CLDN4 or CLDN9. Binding was detected by flow cytometry; see FIGS. 2, 3 and 4. The y-axis represents the percentage of cells bound by antibody (Q2 population) while the x-axis represents the concentration of antibody used.

MuMAB 5F2D2 showed strong binding to human CLDN6 and weak binding to human CLDN9. MuMAB 27A showed strong binding to human CLDN6 and very weak binding to human CLDN9. MuMAB 36A showed strong binding to human CLDN6 and virtually no binding to human CLDN9. None of the antibodies interacted with either human CLDN3 or 4.

Figure 5:
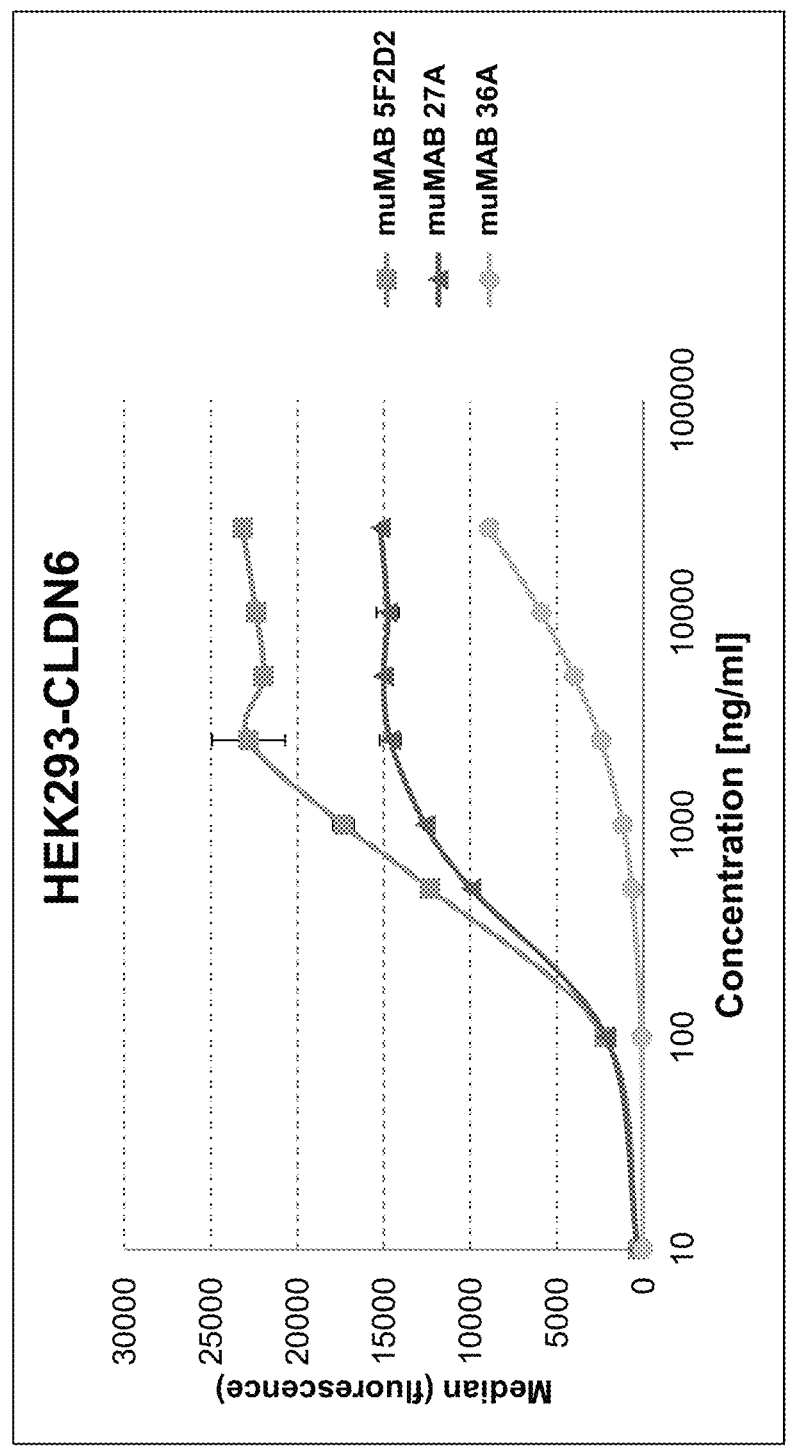
FIG. 5:
Relative affinities of anti-CLDN6 murine monoclonal antibodies muMAB 5F2D2, 27A and 36A.
MuMAB 5F2D2 and 27A exhibit EC50 values of 350-450 ng/ml and saturation of binding is achieved at low concentrations whereas muMAB 36A does not show saturation of binding even at the highest concentration.

For determining relative affinities, the binding of anti-CLDN6 antibodies to human CLDN6 stably expressed on the surface of HEK293 cells was analysed by flow cytometry. In the saturation binding experiment the concentration of the antibodies was plotted against the FACS signals (median of fluorescence intensity); see FIG. 5. The EC50 (antibody concentration that binds to half the binding sites at equilibrium) was calculated by nonlinear regression. The results show that the antibodies have characteristic binding patterns. MuMAB 5F2D2 and 27A exhibited low EC50 values (EC50 350-450 ng/ml) and saturation of binding was achieved at low concentrations whereas muMAB 36A did not show saturation of binding even at the highest concentration.

Example 3: Effector Functions of Antibodies Obtained According to the Invention

The CDC activity of anti-CLDN6 antibodies was analysed using a luciferase-dependent assay to detect endogenous ATP within non-lysed cells. To this end, CHO-K1 cells stably expressing human CLDN6 were treated with different concentrations of MuMAB 5F2D2, 27A or 36A or anti-CLDN6 (R&D Systems, MAB3656) as an internal control.

Figure 6:
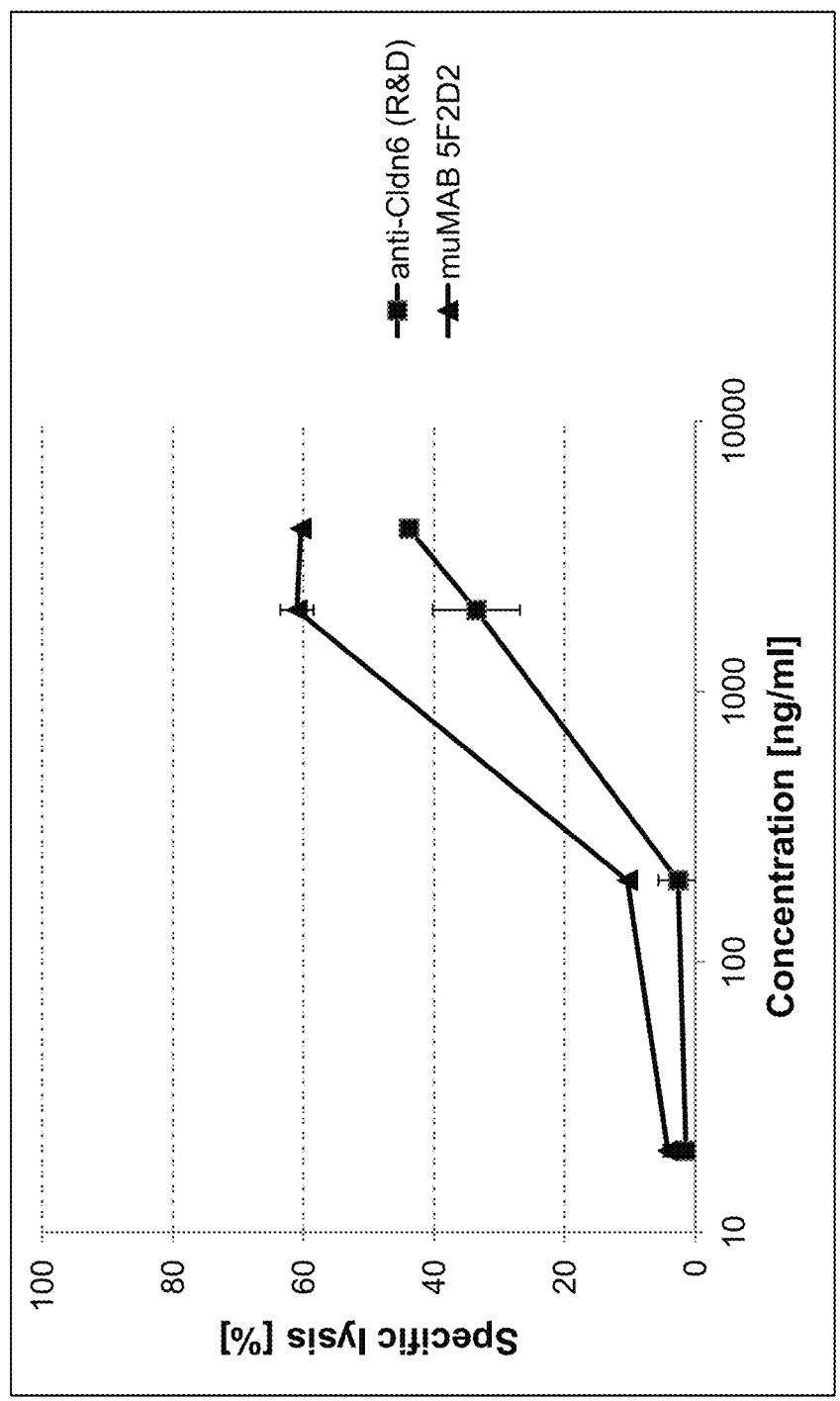
FIG. 6:
Complement-dependent cytotoxicity (CDC) activity of anti-CLDN6 murine monoclonal antibody muMAB 5F2D2.
MuMAB 5F2D2 shows CDC activity in a dose-dependent manner.
Figure 7:
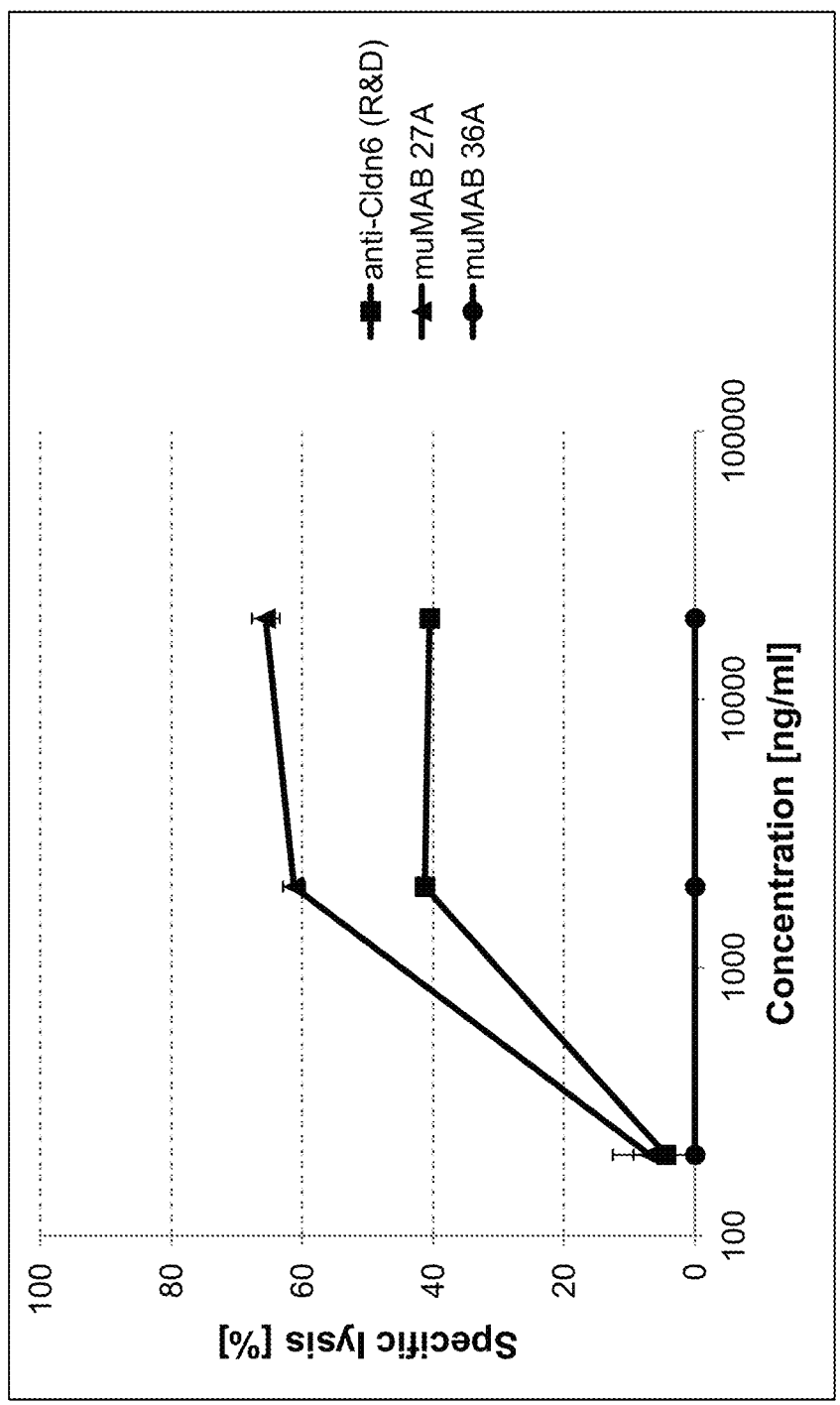
FIG. 7:
Complement-dependent cytotoxicity (CDC) activity of anti-CLDN6 murine monoclonal antibodies muMAB 27A and 36A.

MuMAB 5F2D2 showed CDC activity in a dose-dependent manner; see FIG. 6. MuMAB 27A exhibited dose-dependent CDC activity whereas muMAB 36A was not able to induce CDC in vitro; see FIG. 7.

The ability of the chimeric anti-CLDN6 antibody chimAB 5F2D2 to induce antibody-dependent cell-mediated cytotoxicity (ADCC) on endogenously CLDN6 expressing NEC8 and NEC8 LVTS2 54 (CLDN6 knock-down) cells was determined; see FIG. 8. The chimeric anti-CLDN6 antibody chimAB 5F2D2 and the positive control Herceptin induced ADCC on NEC8 cells with effector cells of two different donors in a dose dependent manner. The efficiency to induce ADCC on NEC8 LVTS2 54 cells (CLDN6 knock-down) was strongly decreased with chimAB 5F2D2 compared to NEC8 parental cells, proving the target specificity of chimAB 5F2D2.

Example 4: Therapeutic Efficacy of Antibodies Obtained According to the Invention The therapeutic effect of muMAB 5F2D2 was tested in an early treatment xenograft model wherein stably transfected HEK293-CLDN6 and HEK293-mock xenografts were engrafted into athymic Nude-Foxn1$^{nu}$ mice.

MuMAB 5F2D2 showed specific and strong tumor growth inhibition in mice engrafted with HEK293 cells stably expressing human CLDN6; see FIG. 9. MuMAB 5F2D2 had no effect on the tumor growth in mice engrafted with mock control cells. Separate saline control groups of mice received PBS as vehicle at injection volumes equivalent to the applied antibodies.

In addition, a Kruskal-Wallis test showed that tumor volumes were significantly reduced at day 28 (and thereafter) after treatment with muMAB 5F2D2; see FIG. 10. Furthermore, mice treated with the monoclonal murine anti-CLDN6 antibody muMAB 5F2D2 showed prolonged survival compared to PBS control groups. The antibody-dependent effect was not observed in mice engrafted with HEK293-mock cells as a control group; see FIG. 11.

Similarly, testing of muMAB 27A and muMAB 36A in an early treatment xenograft model showed specific and strong tumor growth inhibition in mice engrafted with HEK293 cells stably expressing human CLDN6; see FIGS. 12 and 13. Furthermore, muMAB 27A and 36A were effective in prolonging the survival of engrafted mice; see FIG. 14.

Example 5: CLDN6 as a Cancer Target in Germ Cell Tumors

CLDN3, 4, 6 and 9 expression was tested by immunoblot analysis in NEC8 cells. The testicular germ cell tumor cell line NEC8 only showed expression of CLDN6 (left panel) but not of CLDN3, 4 or 9, respectively (right panels); see FIG. 15. The specificities of the anti-CLDN3, 4 and 9 antibodies used were tested by Western blot using HEK293T cells transiently transfected with expression vectors encoding for the corresponding human claudin.

CLDN6 surface expression on NEC8 cells was analyzed using flow cytometry. The commercially available anti-CLDN6 antibody (R&D Systems, MAB3656) detected expression of CLDN6 on NEC8 cells; see FIG. 16. Mouse IgG2b (Sigma, CRL M8894) was used as an isotype control.

Figure 18:
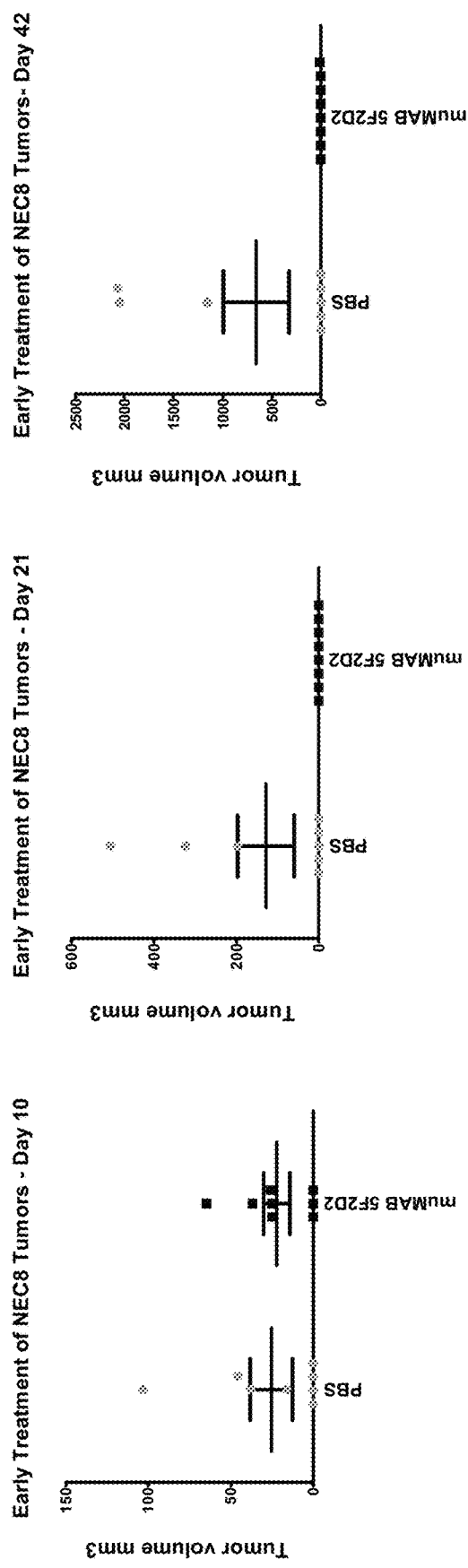

The therapeutic effect of muMAB 5F2D2 in an early treatment xenograft model using mice engrafted with the tumor cell line NEC8 was tested. Compared to the saline control group muMAB 5F2D2 showed specific and strong tumor growth inhibition in mice engrafted with NEC8 cells that endogenously express human CLDN6; see FIG. 17. The Kruskal-Wallis test shows that tumor volumes were reduced at day 21 and 42 after treatment with muMAB 5F2D2; see FIG. 18.

The invention claimed is:

1. A bispecific antibody comprising a first antigen binding site having a binding specificity for CLDN6 and a second antigen binding site having a binding specificity for a second antigen,
   wherein the first antigen binding site comprises a heavy chain CDR1 (HCDR1), a HCDR2, a HCDR3, a light chain CDR1 (LCDR1), a LCDR2, and a LCDR3 of an antibody produced by or obtainable from a hybridoma selected from the group consisting of:
   a. a hybridoma deposited under accession no. DSM ACC3059 (GT512muMAB 36A),
   b. a hybridoma deposited under accession no. DSM ACC3058 (GT512muMAB 27A), and
   c. a hybridoma deposited under accession no. DSM ACC3057 (GT512muMAB 5F2D2).

2. The bispecific antibody of claim 1, wherein the bispecific antibody is a single chain antibody.

3. The bispecific antibody of claim 1, wherein the first antigen binding site is not capable of detectably binding to at least one of (i) CLDN3 associated with the surface of a cell that expresses CLDN3, (ii) CLDN4 associated with the surface of a cell that expresses CLDN4, or (iii) CLDN9 associated with the surface of a cell that expresses CLDN9.

4. The bispecific antibody of claim 1, wherein CLDN6 has the amino acid sequence of SEQ ID NO: 2 or the amino acid sequence of SEQ ID NO: 6.

5. The bispecific antibody of claim 1, wherein the hybridoma is the hybridoma deposited under accession no. DSM ACC3059 (GT512muMAB 36A).

6. The bispecific antibody of claim 5, wherein the bispecific antibody is a single chain antibody.

7. The bispecific antibody of claim 5, wherein the first antigen binding site is not capable of detectably binding to at least one of (i) CLDN3 associated with the surface of a cell that expresses CLDN3, (ii) CLDN4 associated with the surface of a cell that expresses CLDN4, or (iii) CLDN9 associated with the surface of a cell that expresses CLDN9.

8. The bispecific antibody of claim 5, wherein CLDN6 has the amino acid sequence of SEQ ID NO: 2 or the amino acid sequence of SEQ ID NO: 6.

9. The bispecific antibody of claim 1, wherein the hybridoma is the hybridoma deposited under accession no. DSM ACC3058 (GT512muMAB 27A).

10. The bispecific antibody of claim 9, wherein the bispecific antibody is a single chain antibody.

11. The bispecific antibody of claim 9, wherein the first antigen binding site is not capable of detectably binding to at least one of (i) CLDN3 associated with the surface of a cell that expresses CLDN3, (ii) CLDN4 associated with the surface of a cell that expresses CLDN4, or (iii) CLDN9 associated with the surface of a cell that expresses CLDN9.

12. The bispecific antibody of claim 9, wherein CLDN6 has the amino acid sequence of SEQ ID NO: 2 or the amino acid sequence of SEQ ID NO: 6.

13. The bispecific antibody of claim 1, wherein the hybridoma is the hybridoma deposited under accession no. DSM ACC3057 (GT512muMAB 5F2D2).

14. The bispecific antibody of claim 13, wherein the bispecific antibody is a single chain antibody.

15. The bispecific antibody of claim 13, wherein the first antigen binding site is not capable of detectably binding to at least one of (i) CLDN3 associated with the surface of a cell that expresses CLDN3, (ii) CLDN4 associated with the surface of a cell that expresses CLDN4, or (iii) CLDN9 associated with the surface of a cell that expresses CLDN9.

16. The bispecific antibody of claim 13, wherein CLDN6 has the amino acid sequence of SEQ ID NO: 2 or the amino acid sequence of SEQ ID NO: 6.

17. A pharmaceutical composition comprising the bispecific antibody of claim 1.

18. A pharmaceutical composition comprising the bispecific antibody of claim 5.

19. A pharmaceutical composition comprising the bispecific antibody of claim 9.

20. A pharmaceutical composition comprising the bispecific antibody of claim 13.

* * * * *